United States Patent
Coull et al.

(10) Patent No.: US 6,949,343 B2
(45) Date of Patent: *Sep. 27, 2005

(54) METHODS, KITS AND COMPOSITIONS PERTAINING TO PNA MOLECULAR BEACONS

(75) Inventors: James M. Coull, Westford, MA (US); Brian D. Gildea, Billercia, MA (US); Jens J. Hyldig-Nielsen, Holliston, MA (US)

(73) Assignee: Boston Probes, Inc., Bedford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/376,559

(22) Filed: Feb. 28, 2003

(65) Prior Publication Data

US 2003/0232327 A1 Dec. 18, 2003

Related U.S. Application Data

(63) Continuation of application No. 09/888,341, filed on Jun. 22, 2001, now Pat. No. 6,528,267, which is a division of application No. 09/179,298, filed on Oct. 27, 1998, now Pat. No. 6,355,421, which is a continuation-in-part of application No. 08/958,532, filed on Oct. 27, 1997, now abandoned.

(51) Int. Cl.[7] .............................................. C12Q 1/68
(52) U.S. Cl. ......................................................... 435/6
(58) Field of Search ........................................ 435/5, 6

(56) References Cited

U.S. PATENT DOCUMENTS

| | | |
|---|---|---|
| 4,174,384 A | 11/1979 | Ullman |
| 4,261,968 A | 4/1981 | Ullman |
| 4,542,104 A | 9/1985 | Stryer |

(Continued)

FOREIGN PATENT DOCUMENTS

| | | |
|---|---|---|
| EP | 0853129 A2 | 7/1998 |
| WO | WO95/13399 | 5/1995 |
| WO | WO96/02558 | 2/1996 |
| WO | WO97/14026 | 4/1997 |
| WO | WO97/18325 | 5/1997 |
| WO | WO97/39008 | 10/1997 |
| WO | WO97/46711 | 12/1997 |
| WO | WO97/46714 | 12/1997 |
| WO | WO98/10096 | 3/1998 |
| WO | WO98/14612 | 4/1998 |
| WO | WO98/18965 | 5/1998 |
| WO | WO98/24933 | 6/1998 |
| WO | WO98/26093 | 6/1998 |
| WO | WO98/29568 | 7/1998 |
| WO | WO98/30883 | 7/1998 |
| WO | WO98/37232 | 8/1998 |

OTHER PUBLICATIONS

Armitage, B. et al, Hairpin–forming peptide nucleic acid oligomers. Biochem. 37, 9417–9425 (1998).
Bagwell, C.B. et al, A new homogeneous assay system for specific nucleic acid sequences: poly–dA and poly–A detection. Nucleic Acids Res. 22, 2424–2425 (1994).

(Continued)

Primary Examiner—Kenneth R. Horlick
(74) Attorney, Agent, or Firm—Brian D. Gildea

(57) ABSTRACT

This invention is directed to methods, kits and compositions pertaining to PNA Molecular Beacons. PNA Molecular Beacons comprise self-complementary arm segments and flexible linkages that promote intramolecular or intermolecular interactions. In the absence of a target sequence, PNA Molecular Beacons facilitate efficient energy transfer between the linked donor and acceptor moieties of the probe. Upon hybridization of the probe to a target sequence, there is a measurable change in at least one property of at least one donor or acceptor moiety of the probe which can be used to detect, identify or quantitate the target sequence in a sample.

7 Claims, 18 Drawing Sheets

U.S. PATENT DOCUMENTS

| | | |
|---|---|---|
| 4,666,862 A | 5/1987 | Chan |
| 4,725,536 A | 2/1988 | Fritsch |
| 4,725,537 A | 2/1988 | Fritsch |
| 4,766,062 A | 8/1988 | Diamond |
| 4,822,733 A | 4/1989 | Morrison |
| 4,868,103 A | 9/1989 | Stavrianopoulos |
| 4,996,143 A | 2/1991 | Heller |
| 5,118,801 A | 6/1992 | Lizardi |
| 5,210,015 A | 5/1993 | Gelfand |
| 5,237,515 A | 8/1993 | Herron |
| 5,288,611 A | 2/1994 | Kohne |
| 5,312,728 A | 5/1994 | Lizardi |
| 5,439,793 A | 8/1995 | Rose |
| 5,439,797 A | 8/1995 | Tsien |
| 5,491,063 A | 2/1996 | Fisher |
| 5,514,546 A | 5/1996 | Kool |
| 5,527,675 A | 6/1996 | Coull |
| 5,538,848 A | 7/1996 | Livak |
| 5,539,082 A | 7/1996 | Nielsen |
| 5,573,906 A | 11/1996 | Bannwarth |
| 5,601,984 A | 2/1997 | Kohne |
| 5,607,834 A | 3/1997 | Bagwell |
| 5,612,183 A | 3/1997 | Kohne |
| 5,623,049 A | 4/1997 | Lobberding |
| 5,631,169 A | 5/1997 | Lakowicz |
| 5,641,631 A | 6/1997 | Kohne |
| 5,643,762 A | 7/1997 | Ohshima |
| 5,675,517 A | 10/1997 | Stokdijk |
| 5,691,145 A | 11/1997 | Pitner |
| 5,691,146 A | 11/1997 | Mayrand |
| 5,705,346 A | 1/1998 | Okamoto |
| 5,707,804 A | 1/1998 | Mathies |
| 5,714,331 A | 2/1998 | Buchardt |
| 5,723,294 A | 3/1998 | Glass |
| 5,736,336 A | 4/1998 | Buchardt |
| 5,763,167 A | 6/1998 | Conrad |
| 5,770,365 A | 6/1998 | Lane |
| 5,773,571 A | 6/1998 | Nielsen |
| 5,780,233 A | 7/1998 | Guo |
| 5,786,461 A | 7/1998 | Buchardt |
| 5,786,571 A | 7/1998 | Bethel |
| 5,787,032 A | 7/1998 | Heller |
| 5,800,996 A | 9/1998 | Lee |
| 5,804,386 A | 9/1998 | Ju |
| 5,827,660 A | 10/1998 | Singer |
| 5,831,014 A | 11/1998 | Cook |
| 5,846,729 A | 12/1998 | Wu |
| 5,866,336 A | 2/1999 | Nazarenko |
| 5,879,885 A | 3/1999 | Becker |
| 5,925,517 A | 7/1999 | Tyagi |
| 5,985,563 A | 11/1999 | Hyldig-Nielsen |

OTHER PUBLICATIONS

Blok, H.J. et al, Amplifiable hybridization probes containing a molecular switch. Molecular and Cellular Probes 11, 187–194 (1997).

Cardullo, R.A. et al, Detection of nucleic acid hybridization by nonradiative fluorescence resonance energy transfer. Proc. Natl. Acad. Sci. USA 85, 8790–8794 (1988).

Carmel, A. et al, Intramolecularly–quenched fluorescent peptides as fluorogenic substrates of leucine aminopeptidase and inhibitors of clostridial aminopeptidase. Eur. J. Biochem. 73, 617–625 (1977).

Chen, X. et al, A homogeneous, ligase–mediated DNA diagnostic test. Genome Res. 8, 549–556 (1998).

Clegg, R.M., Fluorescence Resonance Energy Transfer and Nucleic Acids. Meth ds in Enzym 1 gy 211, 353–388 (1992).

Corey, D.R. 48000–fold Acceleration of Hyridization by Chemically Modified Oligonucleotides. J. Am. Chem. Soc. 117, 9373–9374 (1995).

Diederichsen, U. et al, Self–Pairing PNA with alternating alanyl/homoalanyl backbone. Tett. Lett. 37, 475–478 (1996).

Dueholm, K.L. et al, Chemistry, properties and applications of PNA (Peptide Nucleic Acid). New J. Chem. 21, 19–31 (1977).

Egholm, M. et al, PNA hybidizes to complementary oligonucletoides obeying the Watson–Crick hydrogen–bonding rules. Nature 365, 566–568 (1993).

Ferguson, J.A. et al, A fiber–optic DNA biosensor microarray for the analysis of gene expression. Nature Biotech. 14, 1681–1684 (1996).

Fujii, M. et al, Nucleic acid analog peptide (NAAP)2, syntheses and properties of novel DNA analog peptides containing nucleobase linked β–aminoalanine. Biorg. & Med. Chem. Lett. 7, 637–640 (Mar. 1997).

Guo, Z. et al, Direct fluorescence analysis of genetic polymorphisms by hybridization with oligonucleotide arrays on glass supports. Nucleic Acids Res. 22, 5456–5465 (1994).

Guo, Z. et al, Enhanced discriminaton of single nucleotide polymorphisms by artificial mismatch hybridization. Nature Biotech. 15, 331–335 (1997).

Haasnoot, C.A.G. et al, Structure, kinetics and thermodynamics of DNA hairpin fragments in solution. J. Biomolecules Structure and Dynamics 1, 115–129 (1983).

Holland, P.M. et al, Detection of specific polymerase chain reaction product by utilizing the 5'→3' exonuclease activity of *Thermus aquaticus* DNA polymerase. Proc. Natl. Acad. Sci. USA 88, 7276–7280 (1991).

Hung, S.–C. et al, Comparison of fluorescence energy transfer primers with different donor–acceptor dye combinations. Analy. Biochem. 255, 32–38 (1998).

Hyldig–Nielsen, J.J. et al, Advances in the use of PNA probes for diagnostic testing. IBC's 3rd Annual International Symposium on Diagnostic Gene Detection and Quantification Technologies for Infectious Agents and Human Genetic Diseases. Feb. 25–27, 1998, Lake Tahoe, NV.

Hyrup, B. et al, Peptide Nucleic Acids (PNA): Synthesis, Properties and Potential Applications. Bioorg. & Med. Chem. 4, 5–23 (1996).

Iyer, M. et al, Accelerated Hybridization of Oligonucleotides to Duplex DNA. The J. of Biol. Chem. 270 14712–14717 (1995).

Jordan, S. et al, New hetero–oligomeric peptide nucleic acids with improved binding properties to complementary DNA. Bioorg. & Med. Chem. Lett. 7, 687–690 (1997).

Jordan, S. et al, Synthesis of new building blocks for peptide nucleic acids containing monomers with variations in the backbone. Bioorg. & Med. Chem. Lett. 7, 781–686 (1997).

Ju, J. et al, Fluorescence energy transfer dye–labeled primers for DNA sequencing and analysis. Proc. Natl. Acad. Sci. USA 92, 4347–4351 (1995).

Kostrikis, L.G. et al, Spectral genotyping of human alleles. Science 279, 1228–1229 (1998).

Krotz, A.H. et al, Synthesis of ÓRetro–inversoÓ Peptide Nucleic Acids: 2. Oligomerization and stability, Tett. Lett. 36, 6941–6944 (1995).

Lagriffoul, P.–H. et al, The synthesis, co–oligomerization and hybridization of a thymine–thymine heterodimer containing PNA. Bioorg. & Med. Chem. Lett. 4, 1081–1082 (1994).

Larin, Z. et al, Fluorescence in situ hybridisation of multiple probes on a single microscope slide. Nucleic Acids Res. 22, 3689–3692 (1994).

Lee, L.G. et al, Allelic discrimination by nick–translation PCR with fluorogenic probes. Nucleic Acids Res. 21, 3761–3766 (1993).

Leone, G. et al, Molecular beacon probes combined with amplification by NASBA enable homogeneous, real–time detection of RNA. Nucl. Acids Res. 26, 2150–2155 (1998).

Lester, A. et al, PNA array technology. Presented at Biochip Technologies Conference in Annapolis (Oct. 1997).

Lewis, R. Oncor and Chiron Offer Improvements & Alternatives in Gene Amplification. Gen. Eng. News. 17, 3 & 36 (Jun. 1, 1997).

Livak, K.J. et al., Oligonucleotides with Fluorescent Dyes at Opposite Ends Provide a Quenched Probe System useful for Detecting PCR Product and Nucleic Acid Hybridization. PCR Methods and Applic. 4, 357–362 (1995).

Lowe, G. et al, Amino acids bearing nucleobases for the synthesis of novel peptide nucleic acids. J. Chem. S c., Perkin Trans. 1, 4, 539–546 (1997).

Lowe, G. et al, Dipeptides bearing nucleobases for the synthesis of novel peptide nucleic acids. J. Chem. Soc., Perkin Trans. 1, 4, 547–554 (1997).

Lowe, G. et al, Solid–phase synthesis of novel peptide nucleic acids. J. Chem. Soc., Perkin Trans. 1, 4 555–560 (1997).

Lutz, M.J. et al, Recognition of Uncharged Polyamide–Linked Nucleic Acid Analogs by DNA Polymerases and Reverse Transcriptases. J. Am. Chem. Soc. 119, 3177–3178 (1997).

Lyamichev, V. et al. Structure–Specific Endonucleolytic Cleavage of Nucleic Acids by Eubacterial DNA Polymerases. Science 260, 778–783 (1993).

Matray, T.J. et al, Selective and stable DNA base pairing without hydrogen bonds. J. Am. Chem. Soc. 120, 6191–6192 (1998).

Meldal, M. et al, Anthranilamide and Nitrotyrosine as a Donor–Acceptor Pair in Internally Quenched Fluorescent Substrates for Endopeptidases: Multicolumn Peptide Synthesis of Enzyme Substrates for Subtilisin Carlsberg and Pepsin. Anal. Biochem. 195, 141–147 (1991).

Mergny, J.–L. et al, Fluorescence Energy Transfer between Two Triple Helix–Forming Oligonucleotides Bound to Duples DNA. Biochem. 33, 15321–15328 (1994).

Nazarenko, I.A. et al, A closed tube format for amplification and detection of DNA based on energy transfer. Nucleic Acids Res. 25, 2516–2521 (1997).

Nazarenko, I.A., A Closed–Tube Format for Amplification and Detection of Nucleic Acids Based on Energy Transfer, Fifth Annual Advances in Nucleic Acid Amplification and Detection, San Francisco, CA (Jun. 16–17, 1997).

Ng, M. et al, A Fluorescent Oligopeptide Energy Transfer Assay with Broad Applications for Neutral Proteases. Anal. Biochem. 183, 50–56 (1989).

Nielsen, P.E. et al, Peptide Nucleic Acid (PNA). A DNA Mimic with a Peptide Backbone. Biocon. Chem. 5, 3–7 (1994).

Nielsen, P.E. et al, Peptide nucleic acids (PNAs): Potential Antisense and Anti–gene Agents. Anti–Cancer Drug Design 8, 53–63 (1993).

Oncor, Inc. Press Release Apr. 14, 1997.

Paris, P.L. et al, Probing DNA sequences in solution with a monomer–excimer fluorescence color change Nucl. Acids Res. 26, 3789–3793 (1998).

Parkhurst, K.M. et al, Kinetic Studies by Fluorescence Resonance Energy Transfer Employing a Double–Labeled Oligonucleotide: Hybridization to the Oligonucleotide Complement and to Single–Stranded DNA. Biochem. 34, 285–292 (1995).

PerSeptive Promotional Literature. Bio ConSepts: PNA and its use as an analytical molecular biology tool. 1996.

PerSeptive Promotional Literature. Peptide Nucleic Acids (PNA): Expanding the role of synthetic DNA analogs. 1995.

PerSeptive Promotional Literature. Peptide Nucleic Acids (PNA): Probing the improbable. 1997.

PerSeptive Promotional Literature. PNA Oligomers as hybridization probes. 1995.

Peterson, K.H. et al, Synthesis and oligomerization of $N^5$–Boc–$N^\alpha$–(thymin–1–ylacetyl)ornithine. Bio rg. & Med. Chem. Lett. 6, 793–796 (1996).

Piatek, A.S. et al, Molecular beacon sequence analysis for detecting drug resistance in mycobacterium tuberculosis. Nature Biotech. 16, 359–363 (1996).

Promisel Cooper, J. et al, Analysis of Fluorescence Energy Transfer in Duplex and Branched DNA Molecules. Biochem. 29, 9261–9268 (1990).

Ratilainen, T. et al, Hybridization of peptide nucleic acid. Biochem. 37, 12331–12342 (1998).

Rye, H.S. et al, Stable fluorescent complexes of double–stranded DNA with bis–intercalating asymmetric cyanine dyes: properties and applications. Nucleic Acids Res. 20, 2803–2812 (1992).

Scheffler, I.E. et al, Helix formation by dAT oligomers. I. Hairpin and straight–chain helices. J. M I. Bi 1. 36, 291–304 (1968).

Selvin, P.R., Fluorescence Resonance Energy Transfer. Methods in Enzym logy 246, 300–334 (1995).

Singh, D. et al, Oligonucleotides, part 5+: synthesis and fluorescence studies of DNA oligomers $d(AT)_5$ containing adenines covalently linked at C–8 with dansyl fluorophore. Nucleic Acids Res. 18, 3339–3345 (1990).

Sixou, S. et al, Intracellular oligonucleotide hybridization detected by fluorescence resonance energy transfer (FRET). Nucleic Acids Res. 22, 662–668 (1994).

Sosnowski, R.G. et al, Rapid determination of single base mismatch mutations in DNA hybrids by direct electric field control. Proc. Natl. Acad. Sci. USA 94, 1119–1123 (1997).

Thisted, M. et al, Detection of immunoglobulin kappa light chain mRNA in paraffin sections by in situ: hybridization using peptide nucleic acid probes. Cell Vision 3, 358–363 (1996).

Thornton, N.B. et al, Chromophore–quencher probes for DNA. New J. Chem. 20, 791–800 (1996).

Tomac, S. et al, Ionic effects on the stability and conformation of Peptide Nucleic Acid Complexes, J. Am. Chem. Soc. 118, 5544–5552 (1996).

Tyagi, S. et al, Molecular Beacons: Probes that Fluoresce upon Hybridization. Nature Biotech. 14, 303–308 (1996).

Tygai, S. et al, Multicolor molecular beacons for allele discrimination. Nature Biotech. 16, 49–53 (1998).

van Gemen, B. et al, Qualitative and quantitative detection of HIV–1 RNA by nucleic acid sequence–based amplification. AIDS 7, S107–S110 (1993).

Vaughan, W.M. et al, Oxygen quenching of pyrenebutyric acid fluorescence in water. A dynamic probe of the microenvironment. Biochem. 9, 464–473 (1970).

Wang, G.T. et al, Design and Synthesis of New Fluorogenic HIV Protease Substrates Based on Resonance Energy Transfer. Tett. Lett. 31, 6493–6496 (1990).

Weber, P.J.A. et al, A fast and inexpensive method for N–terminal fluoresein–labeling of peptides. Bioorg. & Med. Chem. Lett. 8, 597–600 (1998).

Weiler, J. et al, Hybridisation based DNA screening on peptide nucleic acid (PNA) oligomer arrays. Nucl Acids Res. 25, 2792–2799 (1997).

Wittung, P. et al, Induced Chirality in PNA–DNA Duplexes. J. Am. Chem. Soc. 117, 10167–10173 (1995).

Yamamoto, N. et al, A rapid detection of PCR amplification product using a new fluorescent intercalator the pyrylium dye, P2. Nucleic Acids Res. 23, 1445–1446 (1995).

Yang, M. et al, A DNA assay based on fluorescence resonance energy transfer and DNA triplex formation. Analy. Biochem. 259, 272–274 (1998).

Yaron, A. et al, Intramolecularly quenched fluorogenic substrates for hydrolytic enzymes. Analy. Biochem. 95, 228–235 (1979).

Zimmerman, M. et al, A New Fluorogenic Substrate for Chymotrypsin. Anal. Biochem. 70, 258–62 (1976).

Wang, J. et al, Peptide Nucleic Acid Probes for Sequence Specific DNA Biosensors. J. AM. Chem. Soc. 118, 7667–7670 (1996).

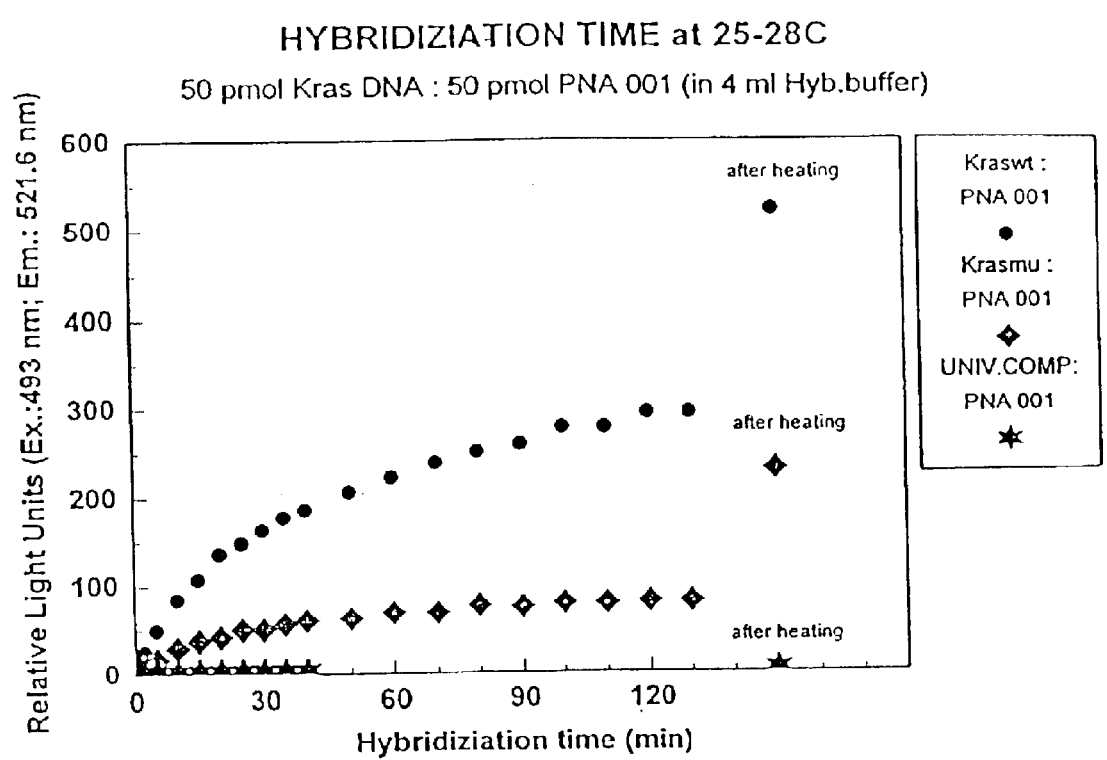

P1/P2

P3

P4

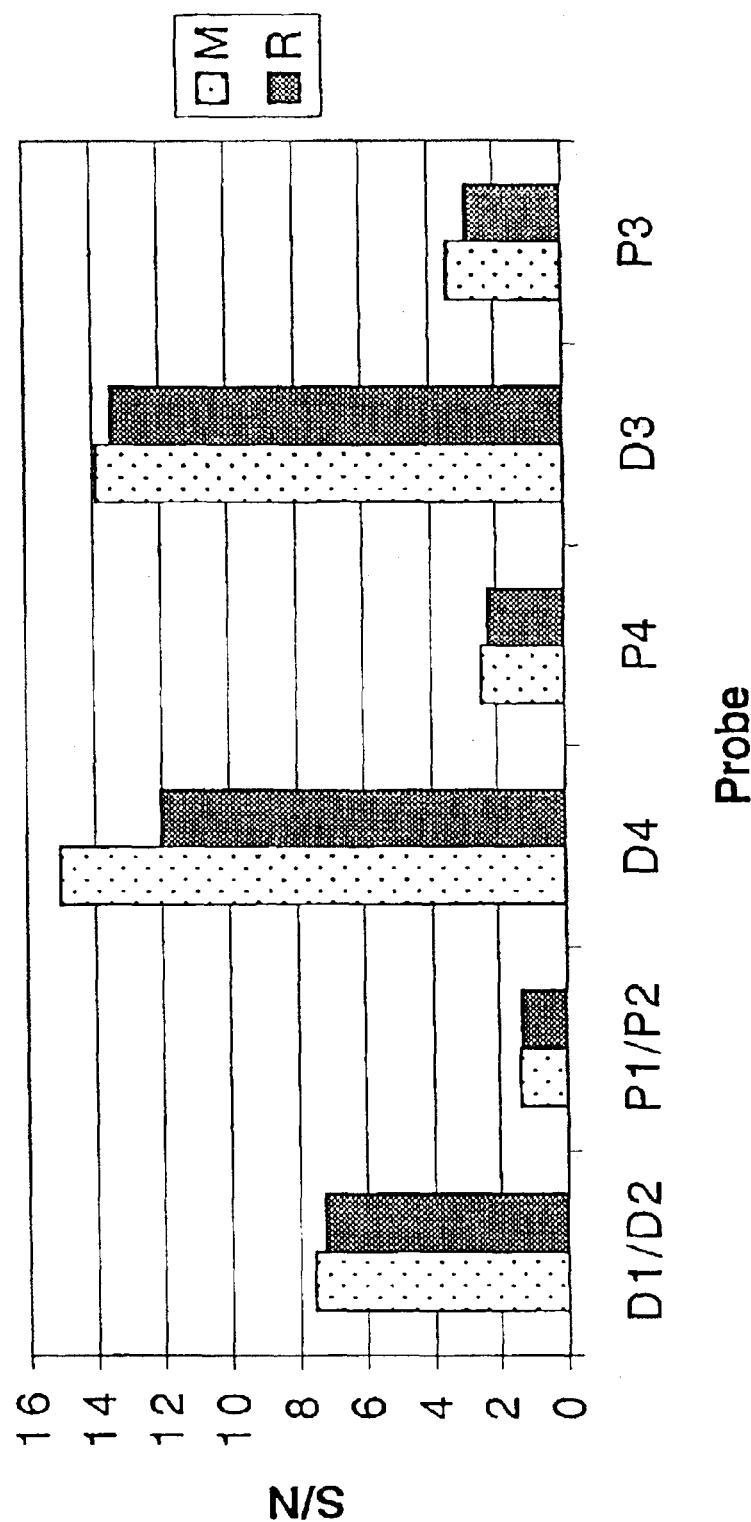

UV Tm Data

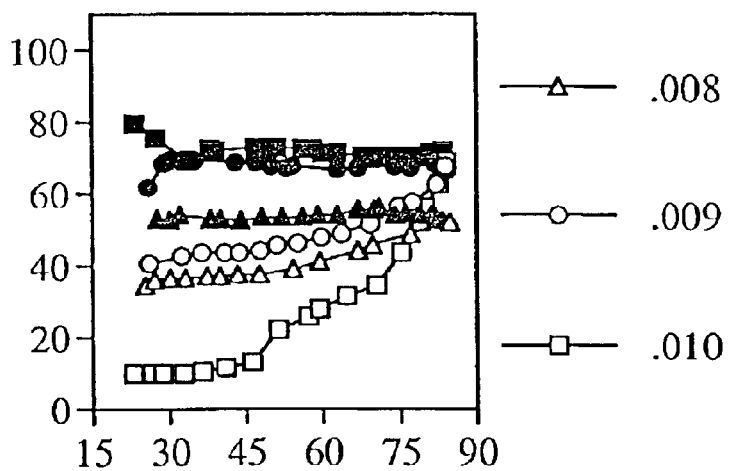
Figure 7B1
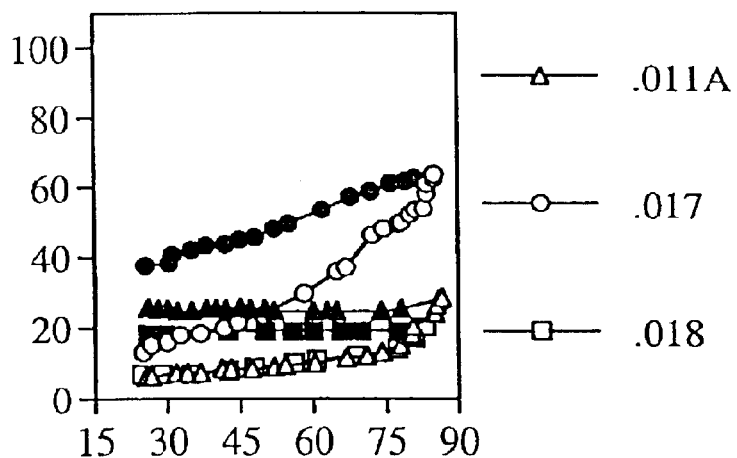
Figure 7B2
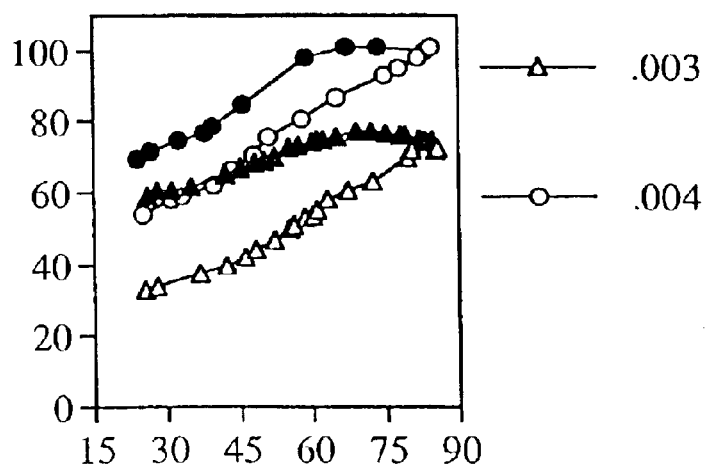
Figure 7B3

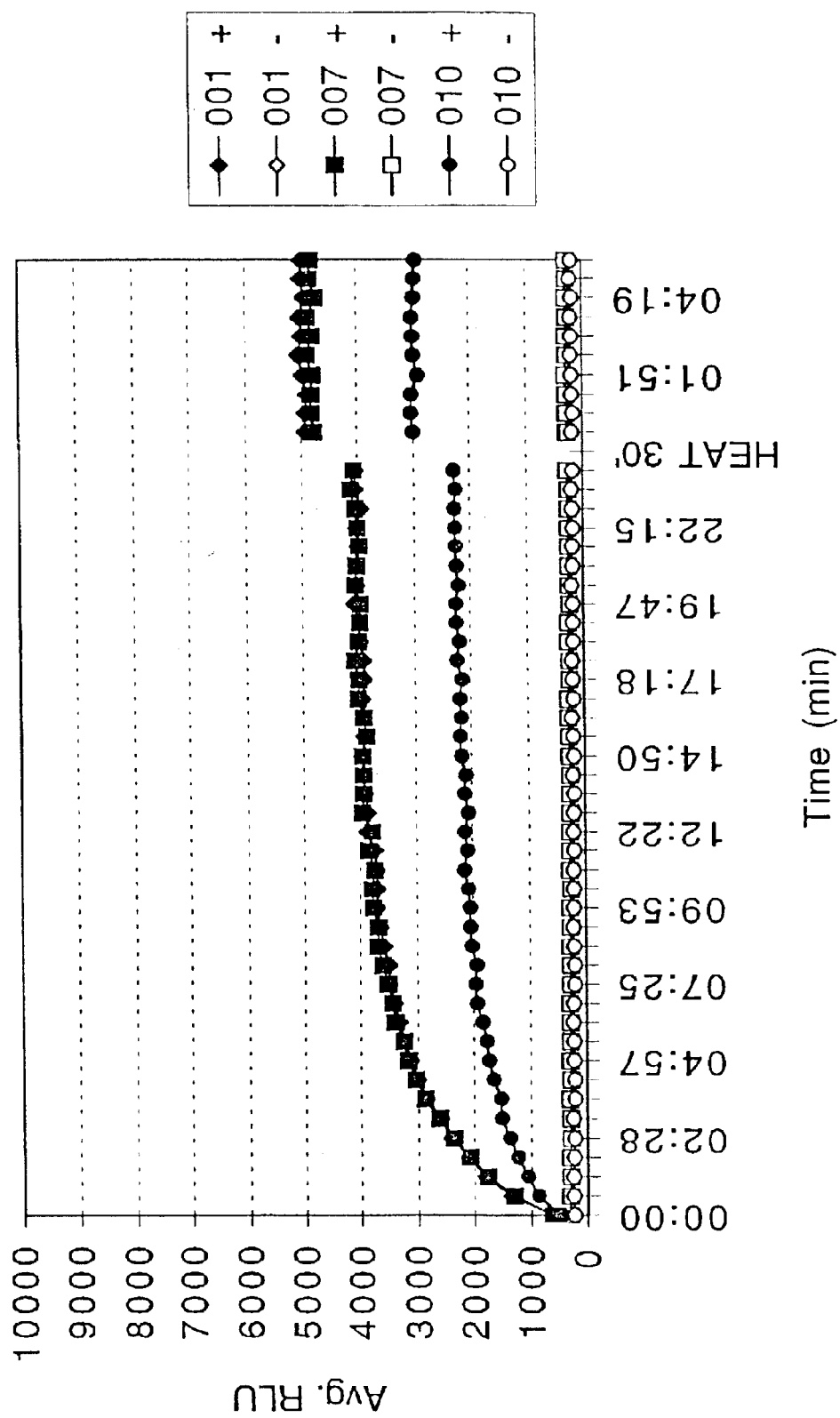

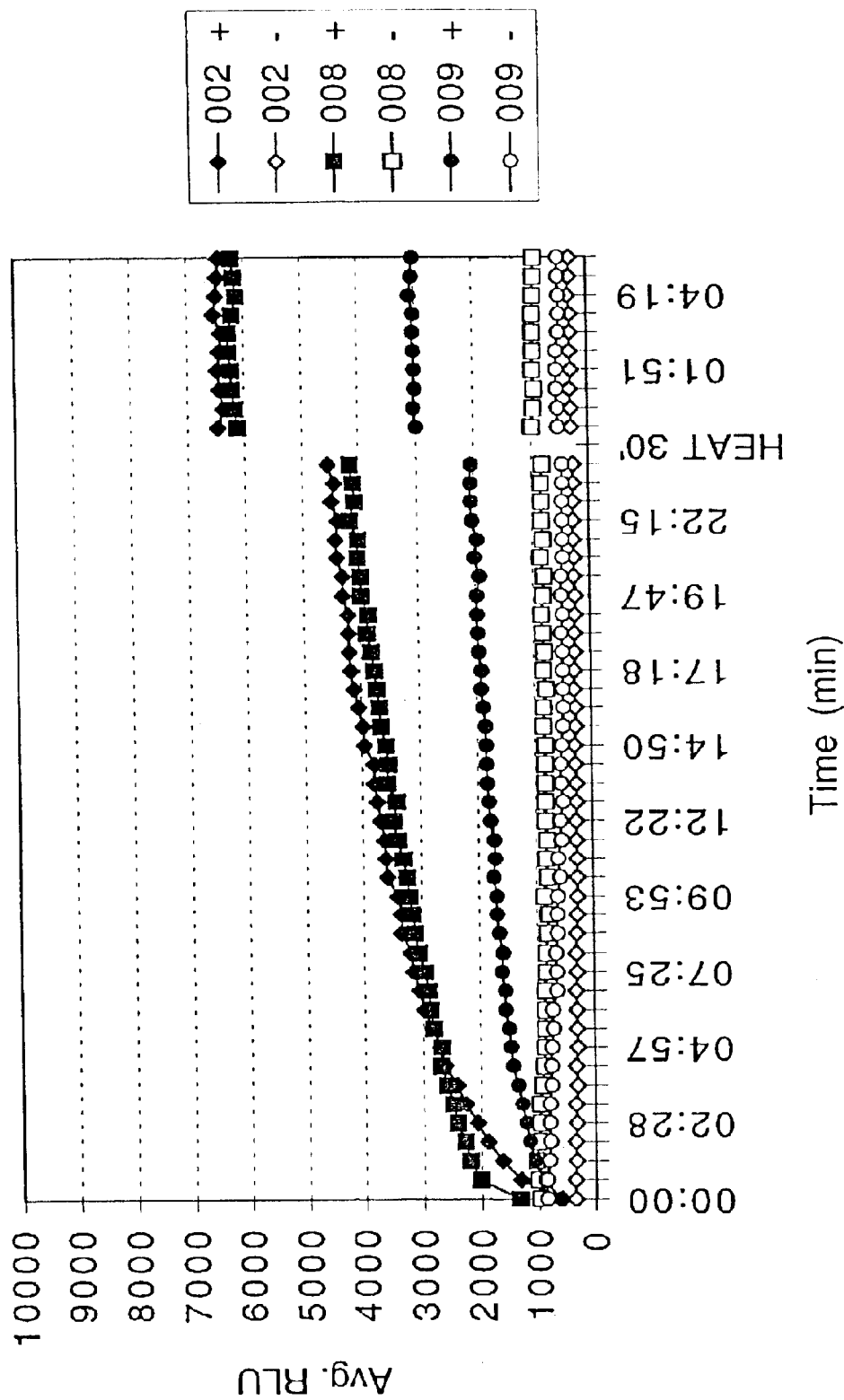
Figure 8A2

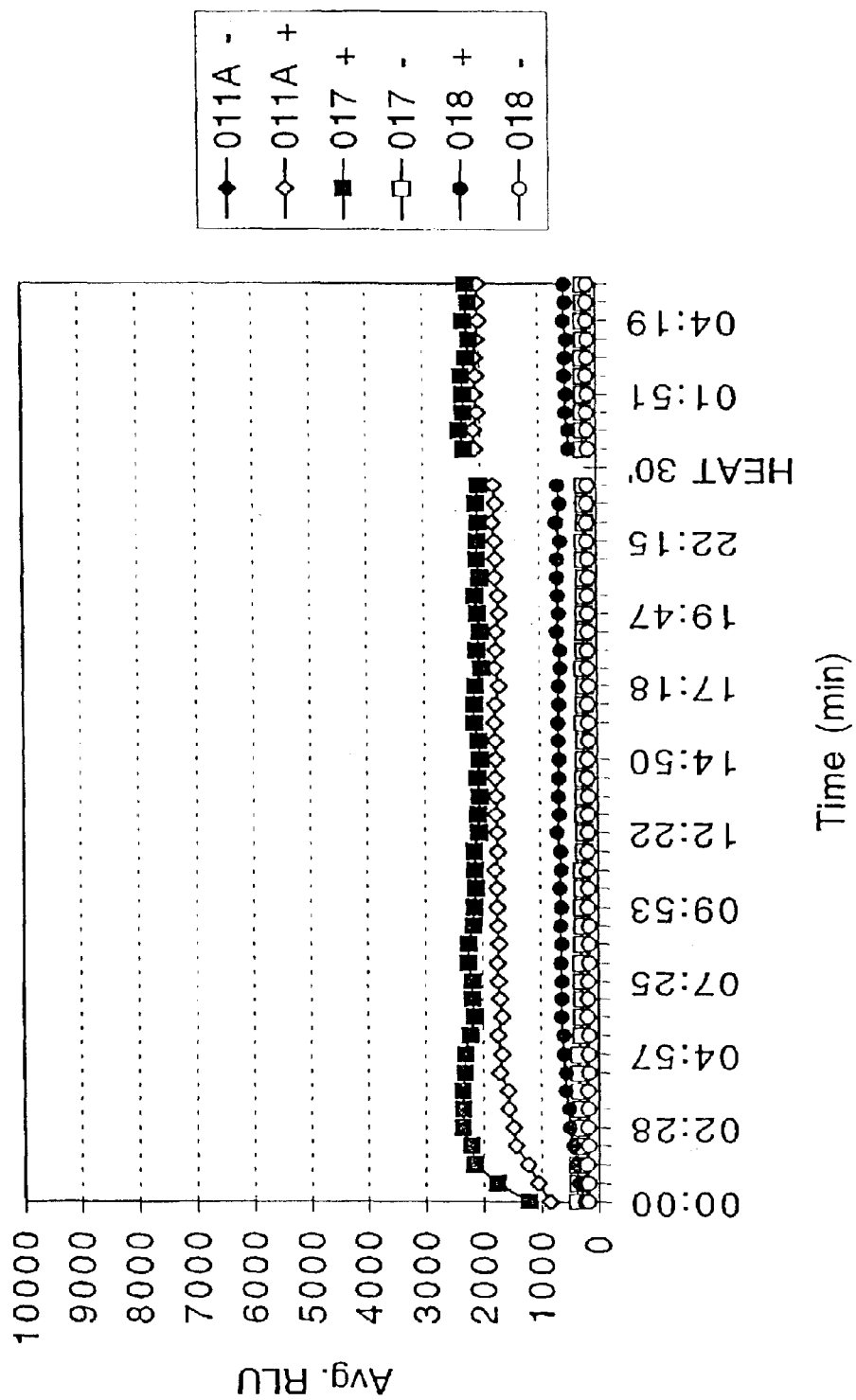
Figure 8A3

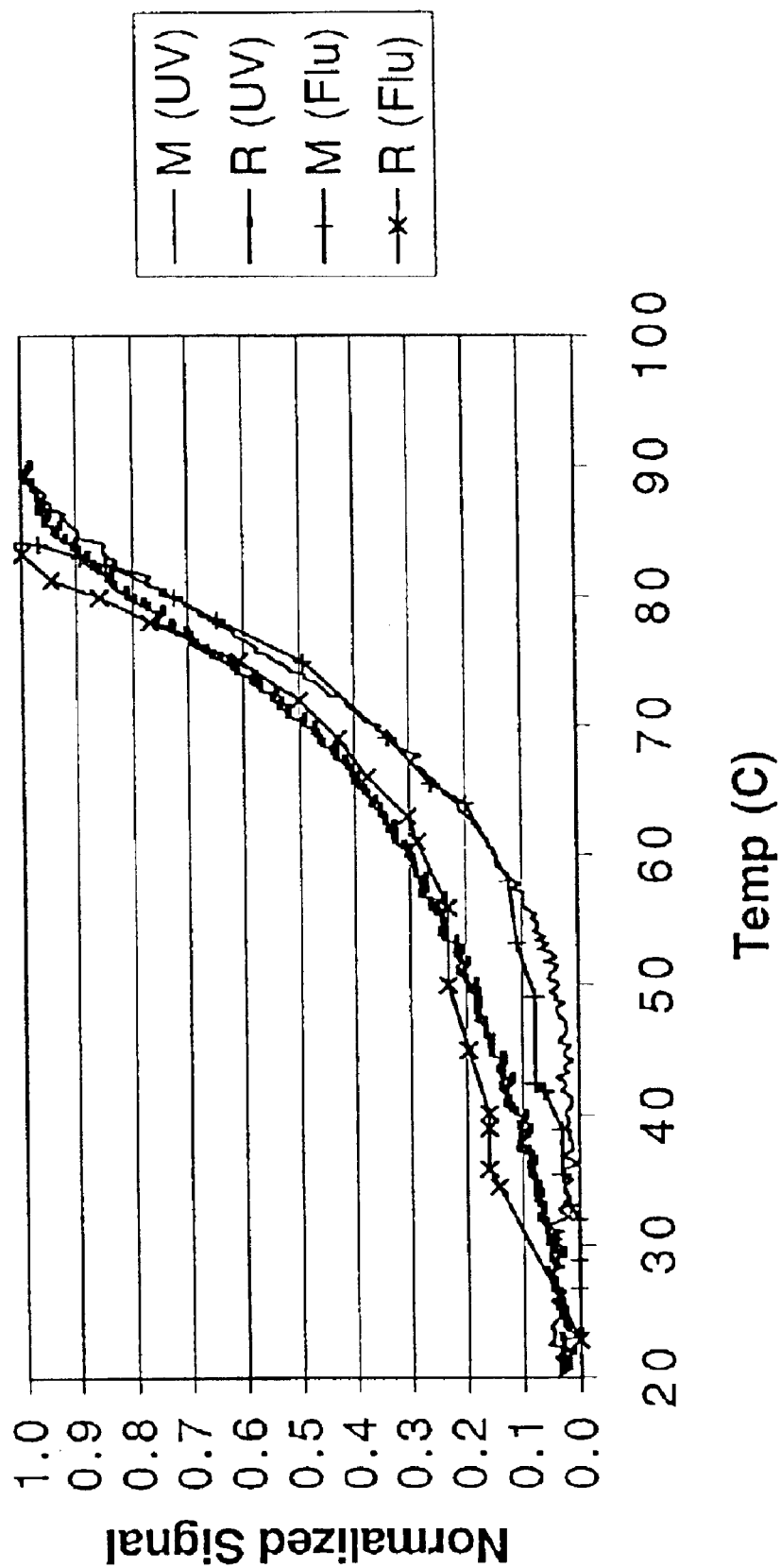

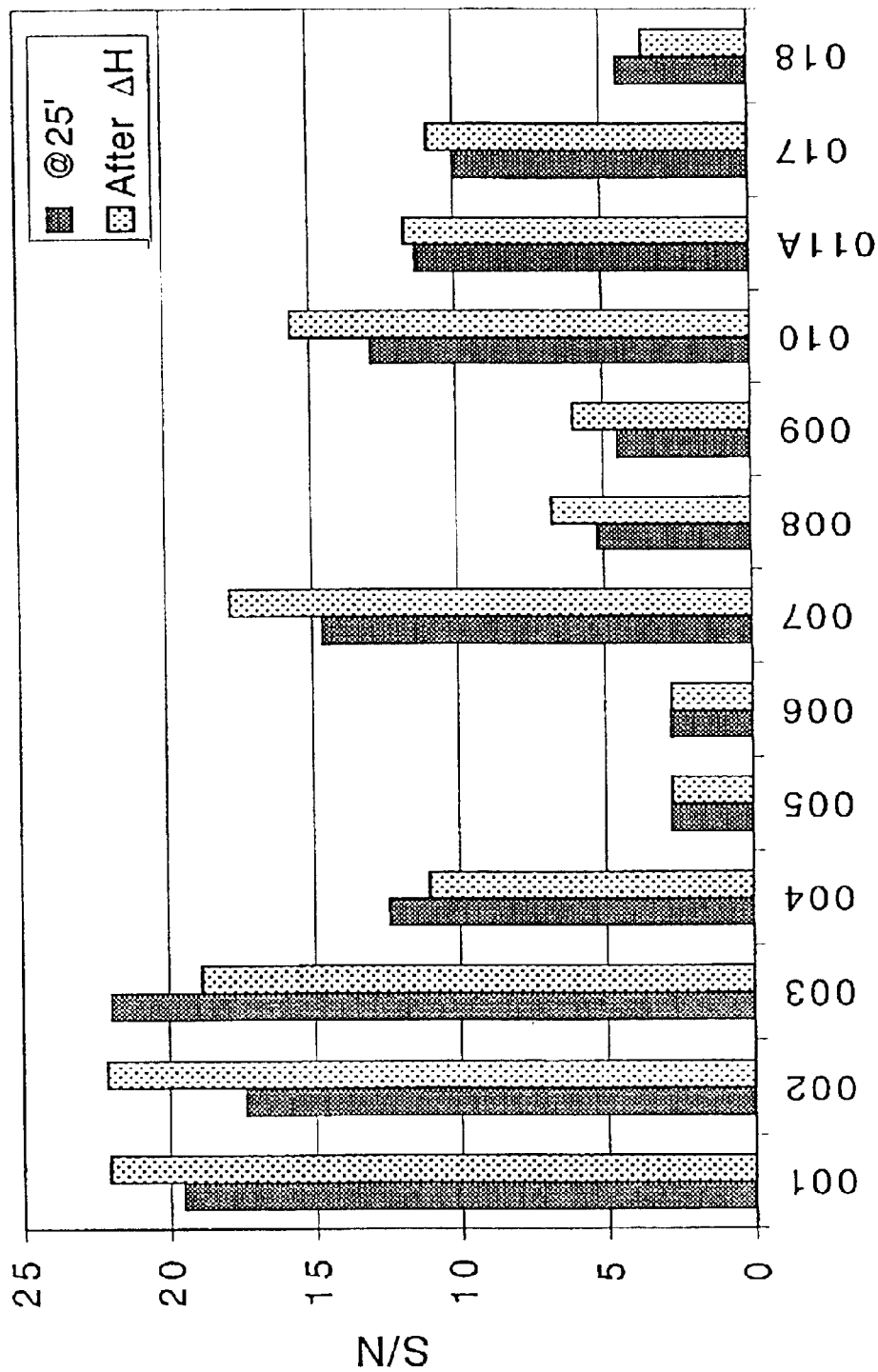

Figure 11
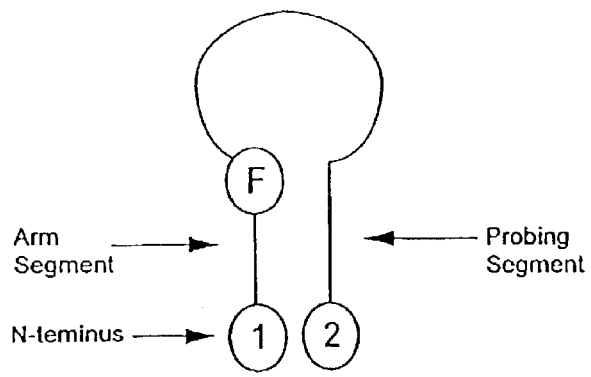
F = Flexible Linkage
1 & 2 are independantly either a quencher or fluorophore provided at least one is a fluorophore and the other is a quencher
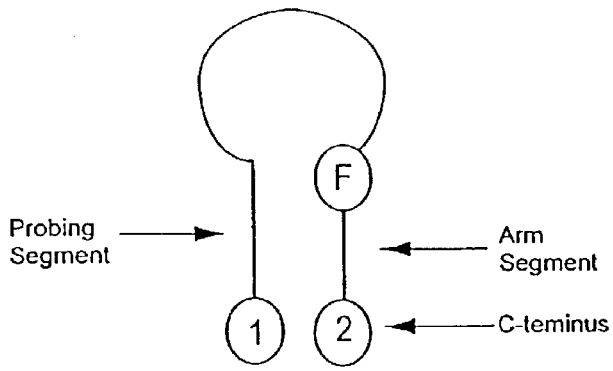
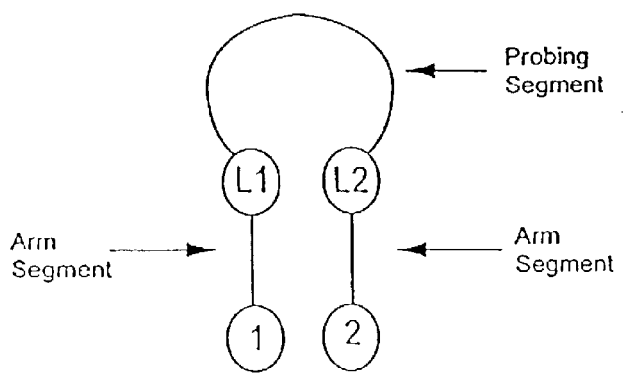
L1 & L2 = "Linkage" provided that at least one of L1 and L2 is a flexible linkage

METHODS, KITS AND COMPOSITIONS PERTAINING TO PNA MOLECULAR BEACONS

CROSS REFERENCE TO RELATED APPLICATIONS

This application is a continuation of U.S. application Ser. No. 09/888,341 (now U.S. Pat. No. 6,528,267), filed on Jun. 22, 2001, which is a division of U.S. application Ser. No. 09/179,298 (now U.S. Pat. No. 6,355,421), filed on Oct. 27, 1998, which is a continuation-in-part of U.S. application Ser. No. 08/958,532 filed on Oct. 27, 1997 (now abandoned).

BACKGROUND OF THE INVENTION

1. Field of the Invention

This invention is related to the field of probe-based nucleic acid sequence detection, analysis and quantitation. More specifically, this invention relates to novel compositions and methods pertaining to PNA Molecular Beacons.

2. Description of the Related Art

Quenching of fluorescence signal can occur by either Fluorescence Resonance Energy Transfer "FRET" (also known as non-radiative energy transfer: See: Yaron et al., *Analytical Biochemistry* 95: 228–235 (1979) at p. 232, col. 1, lns. 32–39) or by non-FRET interactions (also known as radiationless energy transfer; See: Yaron et al., *Analytical Biochemistry* 95 at p. 229, col. 2, lns. 7–13). The critical distinguishing factor between FRET and non-FRET quenching is that non-FRET quenching requires short range interaction by "collision" or "contact" and therefore requires no spectral overlap between the moieties of the donor and acceptor pair (See: Yaron et al., *Analytical Biochemistry* 95 at p. 229, col. 1, lns. 22–42). Conversely, FRET quenching requires spectral overlap between the donor and acceptor moieties and the efficiency of quenching is directly proportional to the distance between the donor and acceptor moieties of the FRET pair (See: Yaron et al., *Analytical Biochemistry* 95 at p. 232, col. 1, ln. 46 to col. 2, ln. 29). Extensive reviews of the FRET phenomenon are described in Clegg, R. M., *Methods Enzymol.*, 221: 353–388 (1992) and Selvin, P. R., *Methods Enzymol.*, 246: 300–334 (1995). Yaron et al. also suggested that the principles described therein might be applied to the hydrolysis of oligonucleotides (See: Yaron et al., *Analytical Biochemistry* 95 at p. 234, col. 2, lns. 14–18).

The FRET phenomenon has been utilized for the direct detection of nucleic acid target sequences without the requirement that labeled nucleic acid hybridization probes or primers be separated from the hybridization complex prior to detection (See: Livak et al. U.S. Pat. No. 5,538,848). One method utilizing FRET to analyze Polymerase Chain Reaction (PCR) amplified nucleic acid in a closed tube format is commercially available from Perkin Elmer. The TaqMan™ assay utilizes a nucleic acid hybridization probe that is labeled with a fluorescent reporter and a quencher moiety in a configuration that results in quenching of fluorescence in the intact probe. During the PCR amplification, the probe sequence specifically hybridizes to the amplified nucleic acid. When hybridized, the exonuclease activity of the Taq polymerase degrades the probe thereby eliminating the intramolecular quenching maintained by the intact probe. Because the probe is designed to hybridize specifically to the amplified nucleic acid, the increase in fluorescence intensity of the sample, caused by enzymatic degradation of the probe, can be correlated with the activity of the amplification process.

Nonetheless, this method preferably requires that each of the fluorophore and quencher moieties be located on the 3' and 5' termini of the probe so that the optimal signal to noise ratio is achieved (See: Nazarenko et al., *Nucl. Acids Res.* 25: 2516–2521(1997) at p. 2516, col. 2, lns. 27–35). However, this orientation necessarily results in less than optimal fluorescence quenching because the fluorophore and quencher moieties are separated in space and the transfer of energy is most efficient when they are close. Consequently, the background emission from unhybridized probe can be quite high in the TaqMan™ assay (See: Nazarenko et al., *Nucl. Acids Res.* 25: at p. 2516, col. 2, lns. 36–40).

The nucleic acid Molecular Beacon is another construct which utilizes the FRET phenomenon to detect target nucleic acid sequences (See: Tyagi et al. *Nature Biotechnology*, 14: 303–308 (1996). A nucleic acid Molecular Beacon comprises a probing sequence embedded within two complementary arm sequences (See: Tyagi et al, *Nature Biotechnology*, 14: at p. 303, col. 1, lns. 22–30). To each termini of the probing sequence is attached one of either a fluorophore or quencher moiety. In the absence of the nucleic acid target, the arm sequences anneal to each other to thereby form a loop and hairpin stem structure which brings the fluorophore and quencher together (See: Tyagi et al., *Nature Biotechnology*, 14: at p. 304, col. 2, lns. 14–25). When contacted with target nucleic acid, the complementary probing sequence and target sequence will hybridize. Because the hairpin stem cannot coexist with the rigid double helix that is formed upon hybridization, the resulting conformational change forces the arm sequences apart and causes the fluorophore and quencher to be separated (See: Tyagi et al. *Nature Biotechnology*, 14: at p. 303, col. 2, lns. 1–17). When the fluorophore and quencher are separated, energy of the donor fluorophore does not transfer to the acceptor moiety and the fluorescent signal is then detectable. Since unhybridized "Molecular Beacons" are non-fluorescent, it is not necessary that any excess probe be removed from an assay. Consequently, Tyagi et al. state that Molecular Beacons can be used for the detection of target nucleic acids in a homogeneous assay and in living cells. (See: Tyagi et al., *Nature Biotechnology*, 14: at p. 303, col. 2; lns. 15–77).

The arm sequences of the disclosed nucleic acid Molecular Beacon constructs are unrelated to the probing sequence (See: Tyagi et al., *Nature Biotechnology*, 14: at p. 303, col. 1; ln. 30). Because the Tyagi et al. Molecular Beacons comprise nucleic acid molecules, proper stem formation and stability is dependent upon the length of the stem, the G:C content of the arm sequences, the concentration of salt in which it is dissolved and the presence or absence of magnesium in which the probe is dissolved (See: Tyagi et al., *Nature Biotchology*, 14: at p. 305, col. 1; lns. 1–16). Furthermore, the Tyagi et al. nucleic acid Molecular Beacons are susceptible to degradation by endonucleases and exonucleases.

Upon probe degradation, background fluorescent signal will increase since the donor and acceptor moieties are no longer held in close proximity. Therefore, assays utilizing enzymes known to have nuclease activity, will exhibit a continuous increase in background fluorescence as the nucleic acid Molecular Beacon is degraded (See: FIG. 7 in Tyagi et al: the data associated with (○) and (□) demonstrates that the fluorescent background, presumably caused by probe degradation, increases with each amplification cycle.) Additionally, Molecular Beacons will also, at least partially, be degraded in living cells because cells contain active nuclease activity.

The constructs described by Tyagi et al. are more broadly described in WO95/13399 (hereinafter referred to as "Tyagi2 et al." except that Tyagi2 et al. also discloses that the nucleic acid Molecular Beacon may also be bimolecular wherein they define bimolecular as being unitary probes of the invention comprising two molecules (e.g. oligonucleotides) wherein half, or roughly half, of the target complement sequence, one member of the affinity pair and one member of the label pair are present in each molecule (See: Tyagi2 et al., p. 8, ln. 25 to p. 9, ln. 3). However, Tyagi2 et al. specifically states that in designing a unitary probe for use in a PCR reaction, one would naturally choose a target complement sequence that is not complementary to one of the PCR primers (See: Tyagi2 et al., p. 41, ln. 27). Assays of the invention include real-time and end point detection of specific single-stranded or double stranded products of nucleic acid synthesis reactions, provided however that if unitary probes will be subjected to melting or other denaturation, the probes must be unimolecular (See: Tyagi2 et al., p. 37, lns. 1–9). Furthermore, Tyagi2 et al. stipulate that although the unitary probes of the invention may be used with amplification or other nucleic acid synthesis reactions, bimolecular probes (as defined in Tyagi2 et al.) are not suitable for use in any reaction (e.g. PCR) wherein the affinity pair would be separated in a target-independent manner (See: Tyagi2 et al., p. 13, lns. 9–12). Neither Tyagi et al. nor Tyagi2 et al. disclose, suggest or teach anything about PNA.

In a more recent disclosure, modified hairpin constructs which are similar to the Tyagi et al. nucleic acid Molecular Beacons, but which are suitable as primers for polymerase extension, have been disclosed (See: Nazarenko et al., *Nucleic Acids Res.* 25: 2516–2521(1997)). A method suitable for the direct detection of PCR-amplified DNA in a closed system is also disclosed. According to the method, the Nazarenko et al. primer constructs are, by operation of the PCR process, incorporated into the amplification product. Incorporation into a PCR amplified product results in a change in configuration that separates the donor and acceptor moieties. Consequently, increases in the intensity of the fluorescent signal in the assay can be directly correlated with the amount of primer incorporated into the PCR amplified product. The authors conclude, this method is particularly well suited to the analysis of PCR amplified nucleic acid in a closed tube format.

Because they are nucleic acids, the Nazarenko et al. primer constructs are admittedly subject to nuclease digestion thereby causing an increase in background signal during the PCR process (See: Nazarenko et al., *Nucleic Acids Res.* 25: at p. 2519, col. 1; lns. 28–39). An additional disadvantage of this method is that the Molecular Beacon like primer constructs must be linearized during amplification (See: Nazarenko et al., *Nucleic Acids Res.* 25: at p. 2519, col. 1, lns. 7–8). Consequently, the polymerase must read through and dissociate the stem of the hairpin modified Molecular Beacon like primer construct if fluorescent signal is to be generated. Nazarenko et al. does not suggest, teach or disclose anything about PNA.

In still another application of FRET to target nucleic acid sequence detection, doubly labeled fluorescent oligonucleotide probes which have been rendered impervious to exonuclease digestion have also been used to detect target nucleic acid sequences in PCR reactions and in-situ PCR (See: Mayrand, U.S. Pat. No. 5,691,146). The oligonucleotide probes of Mayrand comprise a fluorescer (reporter) molecule attached to a first end of the oligonucleotide and a quencher molecule attached to the opposite end of the oligonucleotide (See: Mayrand, Abstract). Mayrand suggests that the prior art teaches that the distance between the fluorophore and quencher is an important feature which must be minimized and consequently the preferred spacing between the reporter and quencher moieties of a DNA probe should be 6–16 nucleotides (See: col. 7, lns. 8–24). Mayrand, however teaches that the reporter molecule and quencher moieties are preferably located at a distance of 18 nucleotides (See: col. 3, lns. 35–36) or 20 bases (See: col. 7, lns. 25–46) to achieve the optimal signal to noise ratio. Consequently, both Mayrand and the prior art cited therein teach that the detectable properties of nucleic acid probes (DNA or RNA) comprising a fluorophore and quencher exhibit a strong dependence on probe length.

Resistance to nuclease digestion is also an important aspect of the invention (See: U.S. Pat. No. 5,691,146 at col. 6, lns. 42–64) and therefore, Mayrand suggests that the 5' end of the oligonucleotide may be rendered impervious to nuclease digestion by including one or more modified internucleotide linkages onto the 5' end of the oligonucleotide probe (See: U.S. Pat. No. 5,691,146 at col. 6, lns. 45–50). Furthermore, Mayrand suggests that a polyamide nucleic acid (PNA) or peptide can be used as a nuclease resistant linkage to thereby modify the 5' end of the oligonucleotide probe of the invention and render it impervious to nuclease digestion (See: U.S. Pat. No 5,691,146 at col. 6, lns. 53–64). Mayrand does not however, disclose, suggest or teach that a PNA probe construct might be a suitable substitute for the practice of the invention despite having obvious knowledge of its existence. Furthermore, Mayrand does not teach one of skill in the art how to prepare and/or label a PNA with the fluorescer or quencher moieties.

The efficiency of energy transfer between donor and acceptor moieties as they can be influenced by oligonucleotide length (distance) has been further examined and particularly applied to fluorescent nucleic acid sequencing applications (See: Mathies et al., U.S. Pat. No. 5,707,804). Mathies et al. states that two fluorophores will be joined by a backbone or chain where the distance between the two fluorophores may be varied (See: U.S. Pat. No. 5,707,804 at col. 4, lns. 1–3). Thus, the distance must be chosen to provide energy transfer from the donor to the acceptor through the well-known Foerster mechanism (See: U.S. Pat. No. 5,707,804 at col. 4, lns. 7–9). Preferably about 3–10 nucleosides separate the fluorophores of a single stranded nucleic acid (See: U.S. Pat. No. 5,707,804 at col. 7, lns. 21–25). Mathies et al. does not suggest, teach or disclose anything about PNA.

From the analysis of DNA duplexes is has been observed that: 1: the efficiency of FET (or FRET as defined herein) appears to depend somehow on the nucleobase sequence of the oligonucleotide; 2: donor fluorescence changes in a manner which suggests that dye-DNA interactions affect the efficiency of FET; and 3: the Forster equation does not quantitatively account for observed energy transfer and therefore the length between donor and acceptor moieties attached to oligonucleotides cannot be quantitated, though it can be used qualitatively (See: Promisel et al., *Biochemistry*, 29: 9261–9268 (1990). Promisel et al. suggest that non-Forster effects may account for some of their observed but otherwise unexplainable results (See: Promisel et al., *Biochemistry*, 29: at p. 9267, col. 1, ln. 43 to p. 9268, col. 1, ln. 13). The results of Promisel et al. suggest that the FRET phenomena when utilized in nucleic acids in not entirely predictable or well understood. Promisel et al. does not suggest, teach or disclose anything about PNA and, in fact, the manuscript predates the invention of PNA.

The background art thus far discussed does not disclose, suggest or teach anything about PNA oligomers to which are directly attached a pair of donor and acceptor moieties. In fact, the FRET phenomenon as applied to the detection of nucleic acids, appears to be confined to the preparation of constructs in which the portion of the probe which is complementary to the target nucleic acid sequence is itself comprised solely of nucleic acid.

FRET has also been utilized within the field of peptides. (See: Yaron et al. *Analytical Biochemistry* 95 at p. 232, col. 2, ln. 30 to p. 234, col. 1, ln. 30). Indeed, the use of suitably labeled peptides as enzyme substrates appears to be the primary utility for peptides which are labeled with donor and acceptor pairs (See: Zimmerman et al., *Analytical Biochemistry*, 70: 258–262 (1976), Carmel et al., *Eur. J. Biochem.*, 73: 617–625 (1977), Ng et al., *Analytical Biochemistry*, 183: 50–56 (1989), Wang et al., *Tett. Lett.*, 31: 6493–6496 (1990) and Meldal et al., *Analytical Biochemistry*, 195: 141–147 (1991). Early work suggested that quenching efficiency of the donor and acceptor pair was dependent on peptide length (See: Yaron et al., *Analytical Biochemistry* 95 at p. 233, col. 2, lns. 36–40). However, the later work has suggested that efficient quenching was not so dependent on peptide length (See: Ng et al., *Analytical Biochemistry*, 183: at p. 54, col. 2, ln 23 to p. 55, col. 1, ln. 12; Wang et al., *Tett. Lett.*, 31 wherein the peptide is eight amino acids in length; and Meldal et al. *Analytical Biochemistry*, 195 at p. 144, col. 1, lns. 33–37). It was suggested by Ng et al. that the observed quenching in long peptides might occur by an as yet undetermined mechanism (See: Ng et al., *Analytical Biochemistry* 183 at p. 55, col. 1, ln 13 to col. 2, ln 7.)

Despite its name, peptide nucleic acid (PNA) is neither a peptide, a nucleic acid nor is it even an acid. Peptide Nucleic Acid (PNA) is a non-naturally occurring polyamide (pseudopeptide) which can hybridize to nucleic acid (DNA and RNA) with sequence specificity (See U.S. Pat. No. 5,539,082 and Egholm et al., *Nature* 365: 566–568 (1993)). PNAs are synthesized by adaptation of standard peptide synthesis procedures in a format which is now commercially available. (For a general review of the preparation of PNA monomers and oligomers please see: Dueholm et al., *New J. Chem.*, 21: 19–31 (1997) or Hyrup et. al., *Bioorganic & Med. Chem.* 4: 5–23 (1996)). Alternatively, labeled and unlabeled PNA oligomers can be purchased (See: PerSeptive Biosystems Promotional Literature: BioConcepts, Publication No. NL612, Practical PNA, *Review* and Practical PNA, Vol. 1, Iss. 2)

Being non-naturally occurring molecules, PNAs are not known to be substrates for the enzymes which are known to degrade peptides or nucleic acids. Therefore, PNAs should be stable in biological samples, as well as have a long shelf-life. Unlike nucleic acid hybridization which is very dependent on ionic strength, the hybridization of a PNA with a nucleic acid is fairly independent of ionic strength and is favored at low ionic strength, conditions which strongly disfavor the hybridization of nucleic acid to nucleic acid (Egholm et al., *Nature*, at p. 567). The effect of ionic strength on the stability and conformation of PNA complexes has been extensively investigated (Tomac et al., *J. Am. Chem. Soc.* 118: 5544–5552 (1996)). Sequence discrimination is more efficient for PNA recognizing DNA than for DNA recognizing DNA (Egholm et al., *Nature*, at p. 566). However, the advantages in point mutation discrimination with PNA probes, as compared with DNA probes, in a hybridization assay appears to be somewhat sequence dependent (Nielsen et al., *Anti-Cancer Drug Design* 8: 53–65, (1993)). As an additional advantage, PNAs hybridize to nucleic acid in both a parallel and antiparallel orientation, though the antiparallel orientation is preferred (See: Egholm et al., *Nature* at p. 566).

Despite the ability to hybridize to nucleic acid in a sequence specific manner, there are many differences between PNA probes and standard nucleic acid probes. These differences can be conveniently broken down into biological, structural, and physico-chemical differences. As discussed in more detail below, these biological, structural, and physico-chemical differences may lead to unpredictable results when attempting to use PNA probes in applications were nucleic acids have typically been employed. This non-equivalency of differing compositions is often observed in the chemical arts.

With regard to biological differences, nucleic acids, are biological materials that play a central role in the life of living species as agents of genetic transmission and expression. Their in vivo properties are fairly well understood. PNA, on the other hand is recently developed totally artificial molecule, conceived in the minds of chemists and made using synthetic organic chemistry. It has no known biological function (i.e. native (unmodified) PNA is not known to be a substrate for any polymerase, ligase, nuclease or protease).

Structurally, PNA also differs dramatically from nucleic acid. Although both can employ common nucleobases (A, C, G, T, and U), the backbones of these molecules are structurally diverse. The backbones of RNA and DNA are composed of repeating phosphodiester ribose and 2-deoxyribose units. In contrast, the backbones of the most common PNAs are composed on N-[2-(aminoethyl)]glycine subunits. Additionally, in PNA the nucleobases are connected to the backbone by an additional methylene carbonyl moiety.

PNA is not an acid and therefore contains no charged acidic groups such as those present in DNA and RNA. Because they lack formal charge, PNAs are generally more hydrophobic than their equivalent nucleic acid molecules. The hydrophobic character of PNA allows for the possibility of non-specific (hydrophobic/hydrophobic interactions) interactions not observed with nucleic acids. Further, PNA is achiral, providing it with the capability of adopting structural conformations the equivalent of which do not exist in the RNA/DNA realm.

The unique structural features of PNA result in a polymer which is highly organized in solution, particularly for purine rich polymers (See: Dueholm et al., *New J. Chem.*, 21: 19–31 (1997) at p. 27, col. 2, lns. 6–30). Conversely, a single stranded nucleic acid is a random coil which exhibits very little secondary structure. Because PNA is highly organized, PNA should be more resistant to adopting alternative secondary structures (e.g. a hairpin stem and/or loop).

The physico/chemical differences between PNA and DNA or RNA are also substantial. PNA binds to its complementary nucleic acid more rapidly than nucleic acid probes bind to the same target sequence. This behavior is believed to be, at least partially, due to the fact that PNA lacks charge on its backbone. Additionally, recent publications demonstrate that the incorporation of positively charged groups into PNAs will improve the kinetics of hybridization (See: Iyer et al., *J. Biol. Chem.* 270: 14712–14717 (1995)). Because it lacks charge on the backbone, the stability of the PNA/nucleic acid complex is higher than that of an analogous DNA/DNA or RNA/DNA complex. In certain situations, PNA will form highly stable triple helical complexes through a process called "strand displacement". No equivalent strand displacement processes or structures are known in the DNA/RNA world.

Recently, the "Hybridization based screening on peptide nucleic acid (PNA) oligomer arrays" has been described wherein arrays of some 1000 PNA oligomers of individual sequence were synthesized on polymer membranes (See: Weiler et al., *Nucl. Acids Res.* 25: 2792–2799(1997)). Arrays are generally used, in a single assay, to generate affinity binding (hybridization) information about a specific sequence or sample to numerous probes of defined composition. Thus, PNA arrays may be useful in diagnostic applications or for screening libraries of compounds for leads which might exhibit therapeutic utility. However, Weiler et al. note that the affinity and specificity of DNA hybridization to immobilized PNA oligomers depended on hybridization conditions more than was expected. Moreover, there was a tendency toward non-specific binding at lower ionic strength. Furthermore, certain very strong binding mismatches were identified which could not be eliminated by more stringent washing conditions. These unexpected results are illustrative of the lack of complete understanding of these newly discovered molecules (i.e. PNA).

In summary, because PNAs hybridize to nucleic acids with sequence specificity, PNAs are useful candidates for investigation as substitute probes when developing probe-based hybridization assays. However, PNA probes are not the equivalent of nucleic acid probes in both structure or function. Consequently, the unique biological, structural, and physico-chemical properties of PNA requires that experimentation be performed to thereby examine whether PNAs are suitable in applications where nucleic acid probes are commonly utilized.

SUMMARY OF THE INVENTION

Tyagi et al. and Tyagi2 et al. disclose nucleic acid Molecular Beacons which comprise a hairpin loop and stem to which energy transfer donor and acceptor moieties are linked at opposite ends of the nucleic acid polymer. Numerous PNA polymers were examined in an attempt to prepare a PNA Molecular Beacon. The applicant's have determined that all probes they examined, which contained linked donor and acceptor moieties exhibited a low inherent noise (background) and an increase in detectable signal upon binding of the probe to a target sequence. Very surprisingly, these characteristic properties of a nucleic acid Molecular Beacon were observed whether or not the PNA oligomer possessed self-complementary arm segments intended to form a PNA hairpin. For example, PNA oligomers prepared as control samples which by design did not possess any self-complementary arm segments suitable for forming a hairpin exhibited a signal (PNA oligomer bound to target sequence) to noise (no target sequence present) ratio which was quite favorable as compared with probes comprising flexible linkages and self-complementary arm segments.

Applicant's data further demonstrates that flexible linkages inserted within the probe and shorter self-complementary arm segments are a preferred embodiment since the signal to noise ratio of probes of this embodiment compare well with the signal to noise ratio published for nucleic acid hairpins (approximately 25 to 1). The data compiled by applicants is inconclusive with respect to whether or not the PNA Molecular Beacons they prepared which have shorter arms segments (2–5 subunits in length) and one or more flexible linkages exist as hairpins. However, applicant's data demonstrates that probes with longer arm segments (e.g. 9 subunits) do form a hairpin (See: Example 19 of this specification) and unlabeled probes having arms segments as short as six subunits do not exist primarily as a hairpin (See: Example 19 of this specification). Furthermore, the signal to noise ratio for those probes having longer arm segments suitable for forming a hairpin exhibited very poor a signal to noise ratios upon melting of the hairpin or when in the presence of a complementary nucleic acid. Consequently, embodiments having longer arm segments (e.g. 6 or more subunits) do not appear to be well suited for use in the detection of nucleic acid targets.

The data compiled by applicant's demonstrates the non-equivalence of structure and function of PNA as compared with nucleic acids. Consequently, this invention pertains to methods, kits and compositions pertaining to PNA Molecular Beacons. Though we refer to the probes of this invention as PNA Molecular Beacons, we do not mean to imply that they exist as hairpins since they may well exist as aggregates, bimolecular constructs or as higher order hybrids (e.g. multimers). Regardless of the nature of the secondary structure, a PNA Molecular Beacon efficiently transfers energy between donor and acceptor moieties linked to the probe in the absence of target sequence. Upon hybridization of the probing nucleobase sequence to a target sequence, the efficiency of energy transfer between donor and acceptor moieties of a PNA Molecular Beacon is altered such that detectable signal from at least one linked moiety can be used to monitor or quantitate the occurrence of the hybridization event.

At a minimum a PNA Molecular Beacon comprises a probing nucleobase sequence, two arm segments, wherein at least one arm segment is linked to the probe through a flexible linkage, at least one linked donor moiety and at least one linked acceptor moiety. The donor and acceptor moieties can be linked at any position within the PNA Molecular Beacon provided that the point of attachment of donor and acceptor moieties of a set are located at opposite ends of the probing nucleobase sequence.

The probing nucleobase sequence is designed to hybridize to at least a portion of a target sequence. The first and second arm segments of the PNA Molecular Beacon provide for intramolecular or intermolecular interactions which stabilize secondary structures, dimers and/or multimers which when formed stabilize the rate of energy transfer between donor and acceptor moieties of the unhybridized PNA Molecular Beacon. Without intending to be bound to this hypothesis, it is believed that the flexible linkages provide flexibility and randomness to the otherwise highly structured PNA oligomer thereby resulting in more efficient energy transfer of the linked donor and acceptor moieties of the unhybridized PNA Molecular Beacon as compared with probes of similar nucleobase sequence which do not comprise flexible linkages.

In one preferred embodiment, this invention is directed to PNA Molecular Beacons comprising an arm segment having a first and second end. Additionally, there is also a probing nucleobase sequence having a first and second end wherein, the probing nucleobase sequence is complementary or substantially complementary to the target sequence. There is also a second arm segment which is embedded within the probing nucleobase sequence and is complementary or substantially complementary to the first arm segment. The polymer also comprises a flexible linkage which links the second end of the first arm segment to the second end of the probing nucleobase sequence. A donor moiety is linked to the first end of one of either of the first arm segment or the probing nucleobase sequence; and an acceptor moiety is linked to the first end of the other of either of the first arm segment or the probing nucleobase sequence.

In still another preferred embodiment, this invention is directed to PNA Molecular Beacons comprising a probing nucleobase sequence having a first and second end, wherein, the probing nucleobase sequence is complementary or substantially complementary to the target sequence. There is also a first arm segment comprising a first and second end and a second arm segment comprising a first and second end, wherein, at least a portion of the nucleobases of the second arm segment are complementary to the nucleobase sequence to the first arm segment. The polymer also comprises a first flexible linkage which links the second end of the first arm segment to either of the first or second end of the probing nucleobase sequence. There is a second linkage which links the second end of the second arm segment to the other of either of the first or second end of the probing nucleobase sequence. A donor moiety is linked to the first end of one of either of the first or second arm segments; and an acceptor moiety is linked to the first end of the other of either of the first or the second arm segments.

In one preferred embodiment, this invention is related to a method for the detection, identification or quantitation of a target sequence in a sample. The method comprises contacting the sample with a PNA Molecular Beacon and then detecting, identifying or quantitating the change in detectable signal associated with at least one donor or acceptor moiety of the probe whereby the change in detectable signal is used to determine the presence, absence or amount of target sequence present in the sample of interest. The measurable change in detectable signal of at least one donor or acceptor moiety of the probe can be used to determine the presence, absence or amount of target sequence present in the sample of interest since applicant's have demonstrated that the efficiency of energy transfer between donor and acceptor moieties is altered by hybridization of the PNA Molecular Beacon to the intended target sequence, under suitable hybridization conditions. Accurate quantitation can be achieved by correcting for signal generated by any unhybridized PNA Molecular Beacon. Consequently, the PNA Molecular Beacons of this invention are particularly well suited for the detection, identification or quantitation of target sequences in closed tube assays. Because PNAs are not known to be degraded by enzymes, PNA Molecular Beacons are also particularly well suited for detection, identification or quantitation of target sequences in cells, tissues or organisms, whether living or not.

In still another embodiment, this invention is related to kits suitable for performing an assay which detects the presence, absence or number of a target sequences in a sample. The kits of this invention comprise one or more PNA Molecular Beacons and other reagents or compositions which are selected to perform an assay or otherwise simplify the performance of an assay.

In yet another embodiment, this invention is also directed to an array comprising two or more support bound PNA Molecular Beacons suitable for detecting, identifying or quantitating a target sequence of interest. Arrays of PNA Molecular Beacons are convenient because they provide a means to rapidly interrogate numerous samples for the presence of one or more target sequences of interest in real time without using a secondary detection system.

The methods, kits and compositions of this invention are particularly useful for the detection of target sequences of organisms which may be found in food, beverages, water, pharmaceutical products, personal care products, dairy products or environmental samples. The analysis of preferred beverages include soda, bottled water, fruit juice, beer, wine or liquor products. Additionally, the methods, kits and compositions will be particularly useful for the analysis of raw materials, equipment, products or processes used to manufacture or store food, beverages, water, pharmaceutical products, personal care products dairy products or environmental samples.

Whether support bound or in solution, the methods, kits and compositions of this invention are particularly useful for the rapid, sensitive, reliable and versatile detection of target sequences which are particular to organisms which might be found in clinical environments. Consequently, the methods, kits and compositions of this invention will be particularly useful for the analysis of clinical specimens or equipment, fixtures or products used to treat humans or animals. For example, the assay may be used to detect a target sequence which is specific for a genetically based disease or is specific for a predisposition to a genetically based disease. Non-limiting examples of diseases include, β-Thalassemia, sickle cell anemia, Factor-V Leiden, cystic fibrosis and cancer related targets such as p53, p10, BRC-1 and BRC-2.

In still another embodiment, the target sequence may be related to a chromosomal DNA, wherein the detection, identification or quantitation of the target sequence can be used in relation to forensic techniques such as prenatal screening, paternity testing, identity confirmation or crime investigation.

BRIEF DESCRIPTION OF THE DRAWINGS

FIG. 3 is a graphical illustration of experimental data.

FIG. 5 is a graphical representation of comparative fluorescent melting signal to noise ratios.

FIGS. 7B1, 7B2 and 7B3 are graphical illustrations of data for PNA probes which exhibit a Type B Fluorescent Thermal Profile.

FIGS. 8A1, 8A2 and 8A3 are a graphical illustration of data for PNA probes which exhibit a Type A Hybridization Profile.

FIG. 9 is an overlay of normalized fluorescence vs. temperature and absorbance vs. temperature plots for a the labeled unimolecular PNA probe 0.001.

FIG. 10 is a graphical illustration of signal to noise data obtained by Hybridization analysis of PNA oligomers listed in Table 1.

FIG. 11 is an illustration of several possible hairpin configurations of a PNA Molecular Beacon.

DESCRIPTION OF THE PREFERRED EMBODIMENTS

Figure 1:
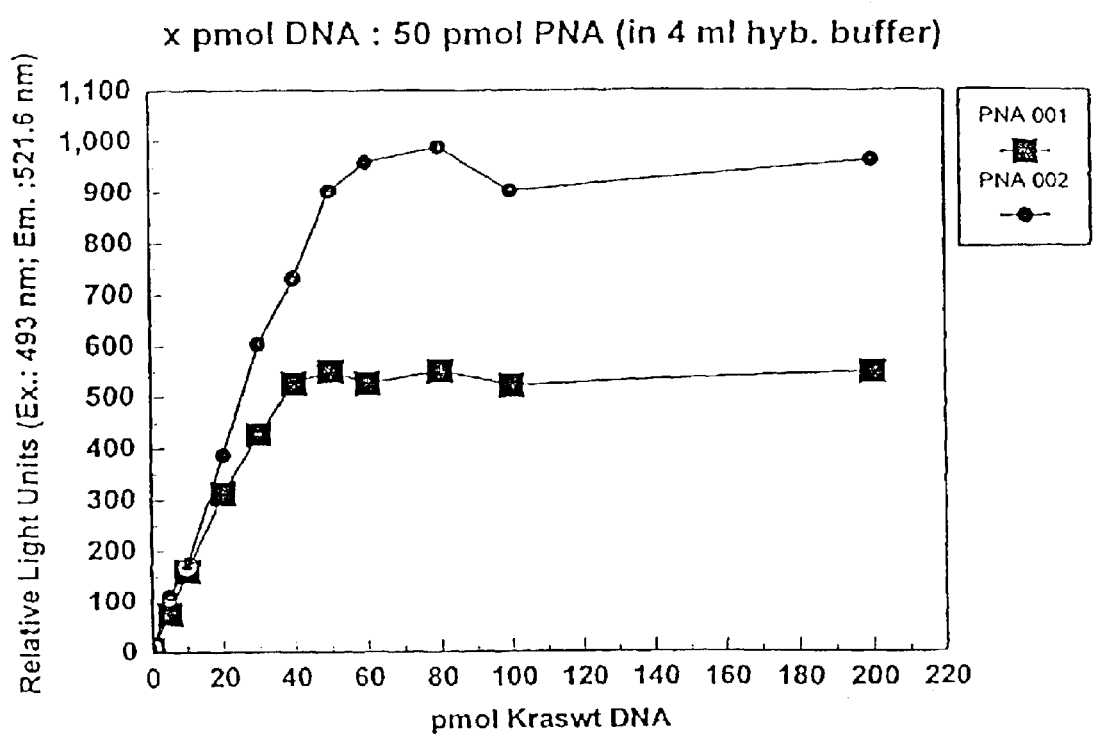
FIG. 1 is a graphical illustration of experimental data.

1. Definitions:

a. As used herein, the term "nucleobase" shall include those naturally occurring and those non-naturally occurring heterocyclic moieties commonly known to those who utilize nucleic acid technology or utilize peptide nucleic acid technology to thereby generate polymers which can sequence specifically bind to nucleic acids.

b. As used herein, the term "nucleobase sequence" is any segment of a polymer which comprises nucleobase containing subunits. Non-limiting examples of suitable polymers or polymers segments include oligonucleotides, oligoribonucleotides, peptide nucleic acids and analogs or chimeras thereof.

c. As used herein, the term "target sequence" is any sequence of nucleobases in a polymer which is sought to be detected. The "target sequence" may comprise the entire polymer or may be a subsequence of the nucleobase sequence which is unique to the polymer of interest. Without limitation, the polymer comprising the "target sequence" may be a nucleic acid, a peptide nucleic acid, a chimera, a linked polymer, a conjugate or any other polymer comprising substituents (e.g. nucleobases) to which the PNA Molecular Beacons of this invention may bind in a sequence specific manner.

d. As used herein, the term "peptide nucleic acid" or "PNA" shall be defined as any oligomer, linked polymer or chimeric oligomer, comprising two or more PNA subunits (residues), including any of the compounds referred to or claimed as peptide nucleic acids in U.S. Pat. Nos. 5,539,082, 5,527,675, 5,623,049, 5,714,331, 5,736,336, 5,773,571 or 5,786,571 (all of which are herein incorporated by reference). The term "Peptide Nucleic Acid" or "PNA" shall also apply to those nucleic acid mimics described in the following publications: Diderichsen et al., *Tett. Lett.* 37:475–478 (1996); Fujii et al., *Bioorg. Med. Chem. Lett.* 7:637–627 (1997); Jordan et al., *Bioorg. Med. Chem. Lett.* 7:687–690 (1997); Krotz et al., *Tett. Lett.* 36:6941–6944 (1995); Lagriffoul et al., *Bioorg. Med. Chem. Lett.* 4:1081–1082 (1994); Lowe et al., *J. Chem. Soc. Perkin Trans.* 1, (1997) 1:539–546; Lowe et al., *J. Chem. Soc. Perkin Trans.* 1 1:547–554 (1997); Lowe et al., *J. Chem. Soc. Perkin Trans.* 1 1:555–560 (1997); and Petersen et al., *Bioorg. Med. Chem. Lett.* 6:793–796 (1996).

In preferred embodiments, a PNA is a polymer comprising two or more PNA subunits of the formula:

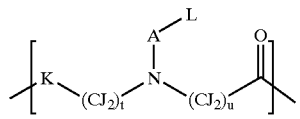

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms which may optionally contain a heteroatom or a substituted or unsubstituted aryl group. Each A is selected from the group consisting of a single bond, a group of the formula; $-(CJ_2)_s-$ and a group of the formula; $-(CJ_2)_sC(O)-$, wherein, J is defined above and each s is an integer from one to five. The integer t is 1 or 2 and the integer u is 1 or 2. Each L is the same or different and is independently selected from the group consisting of J, adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin and fluorescein. In the most preferred embodiment, a PNA subunit consists of a naturally occurring or non-naturally occurring nucleobase attached to the aza nitrogen of the N-[2-(aminoethyl)]glycine backbone through a methylene carbonyl linkage.

2. Detailed Description

I. General:

PNA Synthesis:

Methods for the chemical assembly of PNAs are well known (See: U.S. Pat. Nos. 5,539,082, 5,527,675, 5,623,049, 5,714,331, 5,736,336, 5,773,571 or 5,786,571 (all of which are herein incorporated by reference). Chemicals and instrumentation for the support bound automated chemical assembly of Peptide Nucleic Acids are now commercially available. Chemical assembly of a PNA is analogous to solid phase peptide synthesis, wherein at each cycle of assembly the oligomer possesses a reactive alkyl amino terminus which is condensed with the next synthon to be added to the growing polymer. Because standard peptide chemistry is utilized, natural and non-natural amino acids are routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

Labels:

The labels attached to the PNA Molecular Beacons of this invention comprise a set (hereinafter "Beacon Set(s)") of energy transfer moieties comprising at least one energy donor and at least one energy acceptor moiety. Typically, the Beacon Set will include a single donor moiety and a single acceptor moiety. Nevertheless, a Beacon Set may contain more than one donor moiety and/or more than one acceptor moiety. The donor and acceptor moieties operate such that one or more acceptor moieties accepts energy transferred from the one or more donor moieties or otherwise quench signal from the donor moiety or moieties. The energy transfer moieties of this invention operate by both FRET and non-FRET but preferably do not involve electron transfer.

Preferably the donor moiety is a fluorophore. Preferred fluorophores are derivatives of fluorescein, derivatives of bodipy, 5-(2'-aminoethyl)-aminonaphthalene-1-sulfonic acid (EDANS), derivatives of rhodamine, Cy2, Cy3, Cy 3.5, Cy5, Cy5.5, texas red and its derivatives. Though the previously listed fluorophores might also operate as acceptors, preferably, the acceptor moiety is a quencher moiety. Preferably, the quencher moiety is a non-fluorescent aromatic or heteroaromatic moiety. The preferred quencher moiety is 4-((-4-(dimethylamino)phenyl)azo) benzoic acid (dabcyl).

Transfer of energy may occur through collision of the closely associated moieties of a Beacon Set or through a nonradiative process such as fluorescence resonance energy transfer (FRET). For FRET to occur, transfer of energy between donor and acceptor moieties of a Beacon Set requires that the moieties be close in space and that the emission spectrum of a donor(s) have substantial overlap with the absorption spectrum of the acceptor(s) (See: Yaron et al. *Analytical Biochemistry*, 95: 228–235 (1979) and particularly page 232, col. 1 through page 234, col. 1). Alternatively, collision mediated (radiationless) energy transfer may occur between very closely associated donor and acceptor moieties whether or not the emission spectrum of a donor moiety(ies) has a substantial overlap with the absorption spectrum of the acceptor moiety(ies) (See: Yaron et al., *Analytical Biochemistry*, 95: 228–235 (1979) and particularly page 229, col. 1 through page 232, col. 1). This process is referred to as intramolecular collision since it is believed that quenching is caused by the direct contact of the donor and acceptor moieties (See: Yaron et al.). As applicant's have demonstrated, the donor and acceptor moieties attached to the PNA Molecular Beacons of this invention need not have a substantial overlap between the emission of the donor moieties and the absorbance of the acceptor moieties. Without intending to be bound to this hypothesis, this data suggests that collision or contact operates as the primary mode of quenching in PNA Molecular Beacons.

Detecting Energy Transfer:

Because the efficiency of both collision mediated and nonradiative transfer of energy between the donor and acceptor moieties of a Beacon Set is directly dependent on the proximity of the donor and acceptor moieties, detection of hybrid formation of a PNA Molecular Beacon with a target sequence can be monitored by measuring at least one physical property of at least one member of the Beacon Set which is detectably different when the hybridization complex is formed as compared with when the PNA Molecular Beacon exists in the absence of target sequence. We refer to this phenomenon as the self-indicating property of PNA Molecular Beacons. This change in detectable signal results from the change in efficiency of energy transfer between the donor and acceptor upon hybridization of the PNA Molecular Beacon to a target sequence. Preferably, the means of detection will involve measuring fluorescence of a donor or acceptor fluorophore of a Beacon Set. Most preferably, the Beacon Set will comprise at least one donor fluorophore and at least one acceptor quencher such that the fluorescence of the donor fluorophore is used to detect, identify or quantitate hybridization.

PNA Labeling:

Chemical labeling of a PNA is analogous to peptide labeling. Because the synthetic chemistry of assembly is essentially the same, any method commonly used to label a peptide may be used to label a PNA. Typically, the N-terminus of the polymer is labeled by reaction with a moiety having a carboxylic acid group or activated carboxylic acid group. One or more spacer moieties can optionally be introduced between the labeling moiety and the probing nucleobase sequence of the oligomer. Generally, the spacer moiety is incorporated prior to performing the labeling reaction. However, the spacer may be embedded within the label and thereby be incorporated during the labeling reaction.

Typically the C-terminal end of the probing nucleobase sequence is labeled by first condensing a labeled moiety with the support upon which the PNA is to be assembled. Next, the first synthon of the probing nucleobase sequence can be condensed with the labeled moiety. Alternatively, one or more spacer moieties can be introduced between the labeled moiety and the oligomer (e.g. 8-amino-3,6-dioxaoctanoic acid). Once the PNA Molecular Beacon is completely assembled and labeled, it is cleaved from the support deprotected and purified using standard methodologies.

The labeled moiety could be a lysine derivative wherein the ε-amino group is modified with a donor or acceptor moiety. For example the label could be a fluorophore such as 5(6)-carboxyfluorescein or a quencher moiety such as 4-((4-(dimethylamino)phenyl)azo)benzoic acid (dabcyl). Condensation of the lysine derivative with the synthesis support would be accomplished using standard condensation (peptide) chemistry. The α-amino group of the lysine derivative would then be deprotected and the probing nucleobase sequence assembly initiated by condensation of the first PNA synthon with the α-amino group of the lysine amino acid. As discussed above, a spacer moiety could optionally be inserted between the lysine amino acid and the first PNA synthon by condensing a suitable spacer (e.g. Fmoc-8-amino-3,6-dioxaoctanoic acid) with the lysine amino acid prior to condensation of the first PNA synthon of the probing nucleobase sequence.

Alternatively, a functional group on the assembled, or partially assembled, polymer is labeled with a donor or acceptor moiety while it is still support bound. This method requires that an appropriate protecting group be incorporated into the oligomer to thereby yield a reactive functional to which the donor or acceptor moiety is linked but has the advantage that the label (e.g. dabcyl or a fluorophore) can be attached to any position within the polymer including within the probing nucleobase sequence. For example, the ε-amino group of a lysine could be protected with a 4-methyl-triphenylmethyl (Mtt), a 4-methoxy-triphenylmethyl (MMT) or a 4,4'-dimethoxytriphenylmethyl (DMT) protecting group. The Mtt, MMT or DMT groups can be removed from PNA (assembled using commercially available Fmoc PNA monomers and polystyrene support having a PAL linker; PerSeptive Biosystems, Inc., Framingham, Mass.) by treatment of the resin under mildly acidic conditions. Consequently, the donor or acceptor moiety can then be condensed with the ε-amino group of the lysine amino acid. After complete assembly and labeling, the polymer is then cleaved from the support, deprotected and purified using well known methodologies.

By still another method, the donor or acceptor moiety is attached to the polymer after it is fully assembled and cleaved from the support. This method is preferable where the label is incompatible with the cleavage, deprotection or purification regimes commonly used to manufacture the oligomer. By this method, the PNA will generally be labeled in solution by the reaction of a functional group on the polymer and a functional group on the label. Those of ordinary skill in the art will recognize that the composition of the coupling solution will depend on the nature of oligomer and the donor or acceptor moiety. The solution may comprise organic solvent, water or any combination thereof. Generally, the organic solvent will be a polar non-nucleophilic solvent. Non limiting examples of suitable organic solvents include acetonitrile, tetrahydrofuran, dioxane, methyl sulfoxide and N,N'-dimethylformamide.

Generally the functional group on the polymer to be labeled will be an amine and the functional group on the label will be a carboxylic acid or activated carboxylic acid. Non-limiting examples of activated carboxylic acid functional groups include N-hydroxysuccinimidyl esters. In aqueous solutions, the carboxylic acid group of either of the PNA or label (depending on the nature of the components chosen) can be activated with a water soluble carbodiimide. The reagent, 1-(3-dimethylaminopropyl)-3-ethylcarbodiimide hydrochloride (EDC), is a commercially available reagent sold specifically for aqueous amide forming condensation reactions.

Generally, the pH of aqueous solutions will be modulated with a buffer during the condensation reaction. Preferably, the pH during the condensation is in the range of 4–10. When an arylamine is condensed with the carboxylic acid, preferably the pH is in the range of 4–7. When an alkylamine is condensed with a carboxylic acid, preferably the pH is in the range of 7–10. Generally, the basicity of non-aqueous reactions will be modulated by the addition of non-nucleophilic organic bases. Non-limiting examples of suitable bases include N-methylmorpholine, triethylamine and N,N-diisopropylethylamine. Alternatively, the pH is modulated using biological buffers such as N-[2-hydroxyethyl] piperazine-N'-[2-ethanesulfonic acid (HEPES) or 4-morpholineethane-sulfonic acid (MES) or inorganic buffers such as sodium bicarbonate.

Spacer/Flexible Linker Moieties:

Spacers are typically used to minimize the adverse effects that bulky labeling reagents might have on hybridization properties of PNA Molecular Beacons. Flexible linkers typically induce flexibility and randomness into the PNA Molecular Beacon or otherwise link two or more nucleobase sequences of a probe. Preferred spacer/flexible linker moieties for probes of this invention consist of one or more aminoalkyl carboxylic acids (e.g. aminocaproic acid) the side chain of an amino acid (e.g. the side chain of lysine or ornithine) natural amino acids (e.g. glycine), aminooxyalkylacids (e.g. 8-amino-3,6-dioxaoctanoic acid), alkyl diacids (e.g. succinic acid) or alkyloxy diacids (e.g. diglycolic acid). The spacer/linker moieties may also be designed to enhance the solubility of the PNA Molecular Beacon.

Preferably, a spacer/linker moiety comprises one or more linked compounds having the formula: —Y—(O$_m$—(CW$_2$)$_n$)$_o$—Z—. The group Y is a single bond or a group having the formula selected from the group consisting of: —(CW$_2$)$_p$—, —C(O)(CW$_2$)$_p$—, —C(S)(CW$_2$)$_p$— and —S(O$_2$)(CW$_2$)$_p$. The group Z has the formula NH, NR$^2$, S or O. Each W is independently H, R$^2$, —OR$^2$, F, Cl, Br or I; wherein, each R$^2$ is independently selected from the group consisting of: —CX$_3$, —CX$_2$CX$_3$, —CX$_2$CX$_2$CX$_3$, —CX$_2$CX(CX$_3$)$_2$, and —C(CX$_3$)$_3$. Each X is independently H, F, Cl, Br or I. Each m is independently 0 or 1. Each n, o and p are independently integers from 0 to 10. In the most preferred embodiment, the spacer/flexible linker comprises two linked 8-amino-3,6-dioxaoctanoic acid moieties. Consequently,, Y is —C(O)(CW$_2$)$_p$—, Z is NH, each W is H, m is 1, n is 2, o is 2 and p is 1.

Chimeric Oligomer:

A chimeric oligomer comprises two or more linked subunits which are selected from different classes of subunits. For example, a PNA/DNA chimera would comprise at least two PNA subunits linked to at least one 2'-deoxyribonucleic acid subunit (For methods and compositions related to PNA/DNA chimera preparation See: WO96/40709). The component subunits of the chimeric oligomers are selected from the group consisting of PNA subunits, DNA subunits, RNA subunits and analogues thereof.

Linked Polymer:

A linked polymer comprises two or more nucleobase sequences which are linked by a linker. The nucleobase sequences which are linked to form the linked polymer are selected from the group consisting of an oligodeoxynucleotide, an oligoribonucleotide, a peptide nucleic acid and a chimeric oligomer. The PNA probes of this invention include linked polymers wherein the probing nucleobase sequence is linked to one or more additional oligodeoxynucleotide, oligoribonucleotide, peptide nucleic acid or chimeric oligomers.

Hybridization Conditions/Stringency:

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probing nucleobase sequence/target sequence combination is often found by the well known technique of fixing several of the aforementioned stringency factors and then determining the effect of varying a single stringency factor. The same stringency factors can be modulated to thereby control the stringency of hybridization of PNA Molecular Beacons to target sequences, except that the hybridization of a PNA is fairly independent of ionic strength. Optimal stringency for an assay may be experimentally determined by examination of each stringency factor until the desired degree of discrimination is achieved.

Probing Nucleobase Sequence:

The probing nucleobase sequence of a PNA Molecular Beacon is the sequence recognition portion of the construct. Therefore, the probing nucleobase sequence is designed to hybridize to at least a portion of the target sequence. Preferably the probing nucleobase sequence hybridizes to the entire target sequence. The probing nucleobase sequence is a non-polynucleotide and preferably the probing nucleobase sequence is composed exclusively of PNA subunits. The subunit length of the probing nucleobase sequence will therefore generally be chosen such that a stable complex is formed between the PNA Molecular Beacon and the target sequence sought to be detected, under suitable hybridization conditions. The probing nucleobase sequence of a PNA oligomer, suitable for the practice of this invention, will generally have a length of between 5 and 30 PNA subunits. Preferably, the probing nucleobase sequence will be 8 to 18 subunits in length. Most preferably, the probing nucleobase sequence will be 11–17 subunits in length.

The probing nucleobase sequence of a PNA Molecular Beacons will generally have a nucleobase sequence which is complementary to the target sequence. Alternatively, a substantially complementary probing sequence might be used since it has been demonstrated that greater sequence discrimination can be obtained when utilizing probes wherein there exists a single point mutation (base mismatch) between the probing nucleobase sequence and the target sequence (See: Guo et al., Nature Biotechnology 15: 331–335 (1997), Guo et al., WO97/46711; and Guo et al., U.S. Pat. No. 5,780,233, herein incorporated by reference).

Arm Segments

The arm segments of the PNA Molecular Beacon are designed to anneal to each other and thereby stabilize the interactions which fix the energy transfer of linked donor and acceptor moieties until the PNA Molecular Beacon hybridizes to the target sequence. The arm segments may be of different lengths, but, are preferably the same length. The preferred length of the arm segments will depend on the stability desired for the interactions. However, the arm segments must not be so long that they prohibit hybridization to the target sequence. Preferably, the arm segments are 2–6 subunits in length and most preferably the arm segments are 2–5 subunits in length since applicant's data demonstrates that the highest signal to noise ratios are obtained with PNA Molecular Beacons having arm segments of 5 or less subunits. Preferably arm segments of a PNA Molecular Beacon are comprised primarily of PNA subunits and preferably comprised of only PNA subunits. However, salt pairs and hydrophobic/hydrophobic interactions may contribute to the stability of the interactions which fix the proximity of the donor and acceptor moieties In certain embodiments, both arm segments are external to the probing nucleobase sequence (See: FIG. 11; Configuration III). Alternatively, one arm segment may be embedded within a probing nucleobase sequence (See: FIG. 11; Configurations I and II). When one arm segment is embedded within the probing nucleobase sequence, preferably the other arm segment is oriented to the N-terminus of the PNA Molecular Beacon and the probing nucleobase sequence is oriented toward the C-terminus of the PNA Molecular Beacon.

Flexible Linkages

The flexible linkages link one or more arm forming segments to the PNA Molecular Beacon. Without intending to be bound to this hypothesis, it is believed that flexible linkages provide flexibility and randomness to the otherwise highly structured PNA oligomer thereby resulting in more efficient energy transfer of the linked donor and acceptor moieties of the unhybridized PNA Molecular Beacon. The length and composition of the flexible linkages will be judiciously chosen to facilitate intramolecular interactions between functional groups of the polymer (e.g. nucleobase-nucleobase interactions) which would otherwise not be able to freely interact. Flexible linkages appear to produce PNA Molecular Beacons which exhibit higher signal to noise ratios in hybridization assays and a more reversible modulation of fluorescent signal in response to thermal changes in environment as compared with PNA Molecular Beacons which do not possess flexible linkages. Thus, flexible linkages are an important feature of the PNA Molecular Beacons of this invention.

Blocking Probes:

Blocking probes are PNA or nucleic acid probes which can be used to suppress the binding of the probing nucleobase sequence of a probe to a hybridization site which is unrelated or closely related to the target sequence (See: Coull et al., PCT/US97/21845, a.k.a. WO98/24933). Generally, the blocking probes suppress the binding of the probing nucleobase sequence to closely related non-target sequences because the blocking probe hybridizes to the non-target sequence to form a more thermodynamically stable complex than is formed by hybridization between the probing nucleobase sequence and the non-target sequence. Thus, blocking probes are typically unlabeled probes used in an assay to thereby suppress non-specific signal. Because they are usually designed to hybridize to closely related non-target sequence sequences, typically a set of two or more blocking probes will be used in an assay to thereby suppress non-specific signal from non-target sequences which could be present and interfere with the performance of the assay.

II. Preferred Embodiments of the Invention:

PNA Molecular Beacons:

Tyagi et al. and Tyagi2 et al. disclose nucleic acid Molecular Beacons which comprise a hairpin loop and stem to which energy transfer donor and acceptor moieties are linked at opposite ends of the nucleic acid polymer. Numerous PNA polymers were examined in an attempt to prepare a PNA Molecular Beacon. The applicant's have determined that all probes they examined, which contained linked donor and acceptor moieties exhibited a low inherent noise (background) and an increase in detectable signal upon binding of the probe to a target sequence. Very surprisingly, these characteristic properties of a nucleic acid Molecular Beacon were observed whether or not the PNA oligomer possessed self-complementary arm segments intended to form a PNA hairpin. For example, PNA oligomers prepared as control samples which by design did not possess any self-complementary arm segments suitable for forming a hairpin exhibited a signal (PNA oligomer bound to target sequence) to noise (no target sequence present) ratio which was quite favorable as compared with probes comprising flexible linkages and self-complementary arm segments.

Applicant's data further demonstrates that flexible linkages inserted within the probe and shorter self-complementary arm segments are a preferred embodiment since the signal to noise ratio of probes of this embodiment compare well with the signal to noise ratio published for nucleic acid hairpins (approximately 25 to 1). The data compiled by applicants is inconclusive with respect to whether or not the PNA Molecular Beacons they prepared which have shorter arms segments (2–5 subunits in length) and one or more flexible linkages exist as hairpins. However, applicant's data demonstrates that probes with longer arm segments (e.g. 9 subunits) do form a hairpin (See: Example 19 of this specification) and unlabeled probes having arms segments as short as six subunits do not exist primarily as a hairpin (See: Example 19 of this specification). Furthermore, the signal to noise ratio for those the probes having longer arm segments suitable for forming a hairpin exhibited very poor a signal to noise ratios upon melting of the hairpin or when in the presence of a complementary nucleic acid. Consequently, embodiments having longer arm segments (e.g. 6 or more subunits) do not appear to be well suited for use in the detection of nucleic acid targets.

This invention pertains to methods, kits and compositions pertaining to PNA Molecular Beacons. Though we refer to the probes of this invention as PNA Molecular Beacons, we do not mean to imply that they exist as hairpins since they may well exist as aggregates, bimolecular constructs or as higher order hybrids (e.g. multimers). Regardless of the nature of the secondary structure, a PNA Molecular Beacon efficiently transfers energy between donor and acceptor moieties linked to the probe in the absence of target sequence. Upon hybridization of the probing nucleobase sequence to a target sequence, the efficiency of energy transfer between donor and acceptor moieties of a PNA Molecular Beacon is altered such that detectable signal from at least one linked moiety can be used to monitor or quantitate the occurrence of the hybridization event.

Generally, a PNA Molecular Beacon is a polymer suitable for detecting, identifying or quantitating a target sequence. At a minimum, a PNA Molecular Beacon comprises a probing nucleobase sequence, two arm segments, wherein at least one arm segment is linked to the probe through a flexible linkage, at least one linked donor moiety and at least one linked acceptor moiety. The donor and acceptor moieties can be linked at any position within the PNA Molecular Beacon provided they are separated by at least a portion of the probing nucleobase sequence. Preferably the donor and acceptor moieties of a Beacon Set are located at opposite ends of the probing nucleobase sequence and most preferably at the termini of the PNA Molecular Beacon. The PNA Molecular Beacon is further characterized in that the probe exhibits detectable change in at least one property of at least one linked donor or acceptor moiety which occurs upon hybridization to the target sequence under suitable hybridization conditions.

In one preferred embodiment, this invention is directed to a PNA Molecular Beacons comprising an arm segment having a first and second end. Additionally, there is also a probing nucleobase sequence having a first and second end wherein, the probing nucleobase sequence is complementary or substantially complementary to the target sequence. There is also a second arm segment which is embedded within the probing nucleobase sequence and is complementary or substantially complementary to the first arm segment. The polymer also comprises a flexible linkage which links the second end of the first arm segment to the second end of the probing nucleobase sequence. A donor moiety is linked to the first end of one of either of the first arm segment or the probing nucleobase sequence; and an acceptor moiety is linked to the first end of the other of either of the first arm segment or the probing nucleobase sequence.

In still another preferred embodiment, this invention is directed to a PNA Molecular Beacon comprising a probing nucleobase sequence having a first and second end, wherein, the probing nucleobase sequence is complementary or substantially complementary to the target sequence. There is also a first arm segment comprising a first and second end and a second arm segment comprising a first and second end, wherein, at least a portion of the nucleobases of the second arm segment are complementary to the nucleobase sequence to the first arm segment. The polymer also comprises a first flexible linkage which links the second end of the first arm segment to either of the first or second end of the probing nucleobase sequence. There is a second linkage which links the second end of the second arm segment to the other of either of the first or second end of the probing nucleobase sequence. A donor moiety is linked to the first end of one of either of the first or second arm segments; and an acceptor moiety is linked to the first end of the other of either of the first or the second arm segments.

Preferably, a PNA Molecular Beacons is assembled by stepwise condensation of suitably protected amino acid moieties. Consequently, the polymer is preferably continuous from the amino to the carboxyl terminus. In the most preferred configuration, PNA Molecular Beacons are continuous from the N-terminus to the C-terminus wherein the first arm segment is oriented toward the N-terminus and the probing nucleobase sequence is oriented toward the C-terminus of the polymer. Additionally, the preferred PNA Molecular Beacons comprise a probing nucleobase sequence which is perfectly complementary to the target sequence and a first arm segment which is perfectly complementary to the second arm segment.

It is not a requirement that the PNA Molecular Beacons of this invention form a hairpin. However, if hairpins are formed, preferred embodiments of the PNA Molecular Beacons of this invention can generally be represented in three configurations with are illustrated in FIG. 11. In configuration I, the probing nucleobase sequence is located at the carboxyl terminus of the polymer. The probing nucleobase sequence is linked to the arm forming segment through one or more flexible linker moieties. In this embodiment, one of the two arm segments is embedded within the probing nucleobase sequence. As illustrated, the donor and acceptor moieties are located at opposite ends of the PNA Molecular Beacon but either orientation of the labels is acceptable. This embodiment of a Molecular Beacon is unique even in light of the nucleic acid Molecular Beacons, because one of the two arm forming segments is embedded within the probing segment. Minimization of sequence length is preferred since it should reduce non-specific interactions.

In configuration II, the positioning of the probing nucleobase sequence and arm segments are inverted as compared with configuration I. In this configuration the probing nucleobase sequence is located at the amino terminus of the polymer and is linked to an arm forming segment through one or more flexible linker moieties. As illustrated, the donor and acceptor moieties are located at opposite termini of the PNA Molecular Beacon but either orientation of the labels is acceptable.

In configuration III, the entire probing nucleobase sequence is external to the two arm forming segments. Thus, this embodiment is more similar to the nucleic acid Molecular Beacons than is either configuration I or II. Configuration III, however, differs from nucleic acid Molecular Beacons in that it is comprised of PNA subunits and also contains at least one flexible linkage separating a probing nucleobase sequence and the arm segments.

Unique Features of PNA Molecular Beacons:

There are many differences between prior art nucleic acid constructs and the PNA Molecular Beacons of this invention. For example, nucleic acid constructs comprise a polynucleotide backbone whereas the PNA Molecular Beacons of this invention comprise a probing nucleobase sequence which is not a polynucleotide. Thus, PNA Molecular Beacons which comprise PNA subunits exhibit all of the favorable properties of PNA such as resistance to nuclease degradation, salt independent sequence hybridization to complementary nucleic acids and rapid hybridization kinetics. For probes which do form hairpin stems, the Tm of the stem duplex is substantially independent of the presence or absence of magnesium and the ionic strength of the environment.

Additionally, several of the constructs designed by applicants are PNA Molecular Beacons having arm segments which are embedded within the probing nucleobase sequence. These unique constructs are shorter than corresponding nucleic acid Molecular Beacons. Shorter probes are less costly to synthesize, are generally easier to purify and should exhibit few non-specific interactions since they will comprise less nucleobase sequence diversity.

Additionally, the constructs described herein comprise flexible linkages which applicants have demonstrated to be a preferred embodiment since a higher signal to noise ratio is achieved as compared with PNA probes of similar subunit design which do not comprise flexible linkages. Similarly, the preferred PNA Molecular Beacons of this invention comprise short arm segments since applicant's data demonstrates a clear inverse correlation between arm length and signal to noise ratio. The preferred PNA Molecular Beacons of this invention comprise arms sequences of five or less, and more preferably three or less, subunits.

Probe Sets:

In another embodiment, this invention is directed to sets of PNA Molecular Beacons suitable for detecting or identifying the presence, absence or amount of two or more different target sequences which might be present in a sample. The characteristics of PNA Molecular Beacons suitable for the detection, identification or quantitation of target sequences have been previously described herein. The grouping of PNA Molecular Beacons within sets characterized for specific detection of two or more target sequences is a preferred embodiment of this invention.

Probe sets of this invention shall comprise at least one PNA Molecular Beacon but need not comprise only PNA Molecular Beacons. For example, probe sets of this invention may comprise mixtures of PNA Molecular Beacons, other PNA probes and/or nucleic acid probes, provided however that a set comprises at least one PNA Molecular Beacon as described herein. In preferred embodiments, at least one probe of the set is a blocking probe, as defined herein.

Immobilization of a PNA Molecular Beacon to a Surface:

One or more PNA Molecular Beacons may optionally be immobilized to a surface. In one embodiment, the probe can be immobilized to the surface using the well known process of UV-crosslinking. Alternatively, the PNA oligomer is synthesized on the surface in a manner suitable for deprotection but not cleavage from the synthesis support.

Preferably, the probe is covalently linked to a surface by the reaction of a suitable functional groups on the probe and support. Functional groups such as amino groups, carboxylic acids and thiols can be incorporated in a PNA Molecular Beacon by extension of one of the termini with suitable protected moieties (e.g. lysine, glutamic acid and cystine). When extending the terminus, one functional group of a branched amino acid such as lysine can be used to incorporate the donor or acceptor label at the appropriate position in the polymer (See: Section entitled "PNA Labeling") while the other functional group of the branch is used to optionally further extend the polymer and immobilize it to a surface.

Methods for the attachment of probes to surfaces generally involve the reaction of a nucleophilic group, (e.g. an amine or thiol) of the probe to be immobilized, with an electrophilic group on the support to be modified. Alternatively, the nucleophile can be present on the support and the electrophile (e.g. activated carboxylic acid) present on the PNA Molecular Beacon. Because native PNA possesses an amino terminus, a PNA will not necessarily require modification to thereby immobilize it to a surface (See: Lester et al., Poster entitled "PNA Array Technology").

Conditions suitable for the immobilization of a PNA to a surface will generally be similar to those conditions suitable for the labeling of a PNA (See: subheading "PNA Labeling"). The immobilization reaction is essentially the equivalent of labeling the PNA whereby the label is substituted with the surface to which the PNA probe is to be covalently immobilized.

Numerous types of surfaces derivatized with amino groups, carboxylic acid groups, isocyantes, isothiocyanates and malimide groups are commercially available. Non-limiting examples of suitable surfaces include membranes, glass, controlled pore glass, polystyrene particles (beads), silica and gold nanoparticles.

When immobilized to a surface, energy transfer between moieties of a Beacon Set will occur in the PNA Molecular Beacon. Upon hybridization to a target sequence under suitable hybridization conditions, the location on the surface where the PNA Molecular Beacon (of known sequence) is attached will generate detectable signal based on the measurable change in signal of at least one member of the Beacon Set of the immobilized PNA Molecular Beacon. Consequently, the intensity of the signal on the surface can be used to detect, identify or quantitate the presence or amount of a target sequence in a sample which contacts the surface to which the PNA Molecular Beacon is immobilized. In a preferred embodiment, detection of surface fluorescence will be used to detect hybridization to a target sequence.

Detectable and Independently Detectable Moieties/Multiplex Analysis:

In preferred embodiments of this invention, a multiplex hybridization assay is performed. In a multiplex assay, numerous conditions of interest are simultaneously examined. Multiplex analysis relies on the ability to sort sample components or the data associated therewith, during or after the assay is completed. In preferred embodiments of the invention, distinct independently detectable moieties are used to label the different PNA Molecular Beacons of a set. The ability to differentiate between and/or quantitate each of the independently detectable moieties provides the means to multiplex a hybridization assay because the data which correlates with the hybridization of each of the distinctly (independently) labeled PNA Molecular Beacons to a target sequence can be correlated with the presence, absence or quantity of the target sequence sought to be detected in a sample. Consequently, the multiplex assays of this invention may be used to simultaneously detect the presence, absence or amount of one or more target sequences which may be present in the same sample in the same assay. Preferably, independently detectable fluorophores will be used as the independently detectable moieties of a multiplex assay using PNA Molecular Beacons. For example, two PNA Molecular Beacons might be used to detect each of two different target sequences wherein a fluorescein (green) labeled probe would be used to detect the first of the two target sequences and a rhodamine or Cy3 (red) labeled probe would be used to detect the second of the two target sequences. Consequently, a green, a red or a green and red signal in the assay would signify the presence of the first, second and first and second target sequences, respectively.

Arrays of PNA Molecular Beacons:

Arrays are surfaces to which two or more probes of interest have been immobilized at predetermined locations. Arrays comprising both nucleic acid and PNA probes have been described in the literature. The probe sequences immobilized to the array are judiciously chosen to interrogate a sample which may contain one or more target sequences of interest. Because the location and sequence of each probe is known, arrays are generally used to simultaneously detect, identify or quantitate the presence or amount of one or more target sequences in the sample. Thus, PNA arrays may be useful in diagnostic applications or in screening compounds for leads which might exhibit therapeutic utility.

For example, in a diagnostic assay a target sequence is captured by the complementary probe on the array surface and then the probe/target sequence complex is detected using a secondary detection system. In one embodiment the probe/target sequence complex is detected using a second probe which hybridizes to another sequence of the target molecule of interest. In another embodiment, a labeled antibody is used to detect, identify or quantitate the presence of the probe/target sequence complex.

Since the composition of the PNA Molecular Beacon is known at the location on the surface of the array (because the PNA was synthesized or attached to this position in the array), the composition of target sequence(s) can be directly detected, identified or quantitated by determining the location of detectable signal generated in the array. Because hybridization of the PNA Molecular Beacon to a target sequence is self-indicating, no secondary detection system is needed to analyze the array for hybridization between the PNA Molecular Beacon and the target sequence.

Arrays comprised of PNAs have the additional advantage that PNAs are highly stable and should not be degraded by enzymes which degrade nucleic acid. Therefore, PNA arrays should be reusable provided the nucleic acid from one sample can be striped from the array prior to introduction of the second sample. Upon stripping of hybridized target sequences, signal on the array of PNA Molecular Beacons should again become reduced to background. Because PNAs are not degraded by heat or endonuclease and exonuclease activity, arrays of PNA Molecular Beacon should be suitable for simple and rapid regeneration by treatment with heat, nucleases or chemical denaturants such as aqueous solutions containing formamide, urea and/or sodium hydroxide.

Methods:

In yet another embodiment, this invention is directed to a method for the detection, identification or quantitation of a target sequence in a sample. The method comprises contacting the sample with a PNA Molecular Beacon and then detecting, identifying or quantitating the change in detectable signal associated with at least one moiety of a Beacon Set whereby correlation between detectable signal and hybridization is possible since PNA Molecular Beacons are self-indicating. Because PNA Molecular Beacons are self-indicating, this method is particularly well suited to analysis performed in a closed tube assay (a.k.a. "homogeneous assays"). By closed tube assay we mean that once the components of the assay have been combined, there is no need to open the tube or remove contents of the assay to determine the result. Since the tube need not, and preferably will not, be opened to determine the result, there must be some detectable or measurable change which occurs and which can be observed or quantitated without opening the tube or removing the contents of the assay. Thus, most closed tube assays rely on a change in fluorescence which can be observed with the eye or otherwise be detected and/or quantitated with a fluorescence instrument which uses the tube as the sample holder. Examples of such instruments include the Light Cycler from Idaho Technologies and the Prism 7700 from Perkin Elmer.

Preferred closed tube assays of this invention comprise the detection of nucleic acid target sequences which have been synthesized or amplified by operation of the assay. Non-limiting examples of preferred nucleic acid synthesis or nucleic acid amplification reactions are Polymerase Chain Reaction (PCR), Ligase Chain Reaction (LCR), Strand Displacement Amplification (SDA), Transcription-Mediated Amplification (TMA), Rolling Circle Amplification (RCA) and Q-beta replicase. The PNA Molecular Beacons present in the closed tube assay will generate detectable signal in response to target sequence production from the nucleic acid synthesis or nucleic acid amplification reaction occurring in the closed tube assay. In a most preferred embodiment, the assay is an asymmetric PCR reaction.

Because the PNA Molecular Beacons of this invention can be designed to be stable to the enzymes found in the cell, this method is particularly well suited to detecting a target sequence in a cell, tissue or organism, whether living or not. Thus, in preferred embodiments, in-situ hybridization is used as the assay format for detecting identifying or quantitating target organisms. Most preferably, fluorescence in-situ hybridization (FISH or PNA-FISH) is the assay format. Exemplary methods for performing PNA-FISH can be found in: Thisted et al. Cell Vision, 3:358–363 (1996) or WIPO Patent Application WO97/18325, herein incorporated by reference.

Organisms which have been treated with the PNA Molecular Beacons of this invention can be detected by several exemplary methods. The cells can be fixed on slides and then visualized with a microscope or laser scanning device. Alternatively, the cells can be fixed and then analyzed in a flow cytometer (See for example: Lansdorp et al.; WIPO Patent Application; WO97/14026). Slide scanners and flow cytometers are particularly useful for rapidly quantitating the number of target organisms present in a sample of interest.

Because the method of this invention may be used in a probe-based hybridization assay, this invention will find utility in improving assays used to detect, identify of quantitate the presence or amount of an organism or virus in a sample through the detection of target sequences associated with the organism or virus. (See: U.S. Pat. No. 5,641,631, entitled "Method for detecting, identifying and quantitating organisms and viruses" herein incorporated by reference). Similarly, this invention will also find utility in an assay used in the detection, identification or quantitation of one or more species of an organism in a sample (See U.S. Pat. No. 5,288,611, entitled "Method for detecting, identifying and quantitating organisms and viruses" herein incorporated by reference). This invention will also find utility in an assay used to determine the effect of antimicrobial agents on the growth of one or more microorganisms in a sample (See: U.S. Pat. No. 5,612,183, entitled "Method for determining the effect of antimicrobial agents on growth using ribosomal nucleic acid subunit subsequence specific probes" herein incorporated by reference). This invention will also find utility in an assay used to determine the presence or amount of a taxonomic group of organisms in a sample (See: U.S. Pat. No. 5,601,984, entitled "Method for detecting the presence of amount of a taxonomic group of organisms using specific r-RNA subsequences as probes" herein incorporated by reference).

When performing the method of this invention, it may be preferable to use one or more unlabeled or independently detectable probes in the assay to thereby suppress the binding of the PNA Molecular Beacon to a non-target sequence. The presence of the "blocking probe(s)" helps to increase the discrimination of the assay and thereby improve reliability and sensitivity (signal to noise ratio).

In certain embodiments of this invention, one target sequence is immobilized to a surface by proper treatment of the sample. Immobilization of the nucleic acid can be easily accomplished by applying the sample to a membrane and then UV-crosslinking. For example, the samples may be arranged in an array so that the array can be sequentially interrogated with one or more PNA Molecular Beacons to thereby determine whether each sample contains one or more target sequence of interest.

In still another embodiment, the PNA Molecular Beacon is immobilized to a support and the samples are sequentially interrogated to thereby determine whether each sample contains a target sequence of interest. In preferred embodiments, the PNA Molecular Beacons are immobilized on an array which is contacted with the sample of interest. Consequently, the sample can be simultaneously analyzed for the presence and quantity of numerous target sequences of interest wherein the composition of the PNA Molecular Beacons are judiciously chosen and arranged at predetermined locations on the surface so that the presence, absence or amount of particular target sequences can be unambiguously determined. Arrays of PNA Molecular Beacons are particularly useful because no second detection system is required since PNA Molecular Beacons are self-indicating. Consequently, this invention is also directed to an array comprising two or more support bound PNA Molecular Beacons suitable for detecting, identifying or quantitating a target sequence of interest.

Kits:

In yet another embodiment, this invention is directed to kits suitable for performing an assay which detects the presence, absence or amount of one or more target sequence which may be present in a sample. The characteristics of PNA Molecular Beacons suitable for the detection, identification or quantitation of amount of one or more target sequence have been previously described herein. Furthermore, methods suitable for using the PNA Molecular Beacon components of a kit to detect, identify or quantitate one or more target sequence which may be present in a sample have also been previously described herein.

The kits of this invention comprise one or more PNA Molecular Beacons and other reagents or compositions which are selected to perform an assay or otherwise simplify the performance of an assay. Preferred kits contain sets of PNA Molecular Beacons, wherein each of at least two PNA Molecular Beacons of the set are used to distinctly detect and distinguish between the two or more different target sequences which may be present in the sample. Thus, the PNA Molecular Beacons of the set are preferably labeled with independently detectable moieties so that each of the two or more different target sequences can be individually detected, identified or quantitated (a multiplex assay).

Exemplary Applications for Using the Invention:

Whether support bound or in solution, the methods, kits and compositions of this invention are particularly useful for the rapid, sensitive, reliable and versatile detection of target sequences which are particular to organisms which might be found in food, beverages, water, pharmaceutical products, personal care products, dairy products or environmental samples. The analysis of preferred beverages include soda, bottled water, fruit juice, beer, wine or liquor products. Consequently, the methods, kits and compositions of this invention will be particularly useful for the analysis of raw materials, equipment, products or processes used to manufacture or store food, beverages, water, pharmaceutical products, personal care products, dairy products or environmental samples.

Whether support bound or in solution, the methods, kits and compositions of this invention are particularly useful for the rapid, sensitive, reliable and versatile detection of target sequences which are particular to organisms which might be found in clinical environments. Consequently, the methods, kits and compositions of this invention will be particularly useful for the analysis of clinical specimens or equipment, fixtures or products used to treat humans or animals. For example, the assay may be used to detect a target sequence which is specific for a genetically based disease or is specific for a predisposition to a genetically based disease. Non-limiting examples of diseases include, β-Thalassemia, sickle cell anemia, Factor-V Leiden, cystic fibrosis and cancer related targets such as p53, p10, BRC-1 and BRC-2.

In still another embodiment, the target sequence may be related to a chromosomal DNA, wherein the detection, identification or quantitation of the target sequence can be used in relation to forensic techniques such as prenatal screening, paternity testing, identity confirmation or crime investigation.

EXAMPLES

This invention is now illustrated by the following examples which are not intended to be limiting in any way.

Example 1

Synthesis of N-α-(Fmoc)-N-ε-(NH$_2$)-L-Lysine-OH

To 20 mmol of N-α-(Fmoc)-N-ε-(t-boc)-L-lysine-OH was added 60 mL of 2/1 dichloromethane (DCM)/ trifluoroacetic acid (TFA). The solution was allowed to stir until the tert-butyloxycarbonyl (t-boc) group had completely been removed from the N-α-(Fmoc)-N-ε-(t-boc)-L-lysine-OH. The solution was then evaporated to dryness and the residue redissolved in 15 mL of DCM. An attempt was then made to precipitate the product by dropwise addition of the solution to 350 mL of ethyl ether. Because the product oiled out, the ethyl ether was decanted and the oil put under high vacuum to yield a white foam. The white foam was dissolved in 250 mL of water and the solution was neutralized to pH 4 by addition of saturated sodium phosphate (dibasic). A white solid formed and was collected by vacuum filtration. The product was dried in a vacuum oven at 35–40° C. overnight. Yield 17.6 mmol, 88%.

Example 2

Synthesis of N-α-(Fmoc)-N-ε-(dabcyl)-L-Lysine-OH

To 1 mmol of N-α-(Fmoc)-N-ε-(NH$_2$)-L-Lysine-OH (Example 1) was added 5 mL of N,N'-dimethylformamide (DMF) and 1.1 mmol of TFA. This solution was allowed to stir until the amino acid had completely dissolved.

To 1.1 mmol of 4-((4-(dimethylamino)phenyl)azo) benzoic acid, succinimidyl ester (Dabcyl-NHS; Molecular Probes, P/N D-2245) was added 4 mL of DMF and 5 mmol of diisopropylethylamine (DIEA). To this stirring solution was added, dropwise, the N-α-(Fmoc)-N-ε-(NH$_2$)-L-Lysine-OH solution prepared as described above. The reaction was allowed to stir overnight and was then worked up.

The solvent was vacuum evaporated and the residue partitioned in 50 mL of DCM and 50 mL of 10% aqueous citric acid. The layers were separated and the organic layer washed with aqueous sodium bicarbonate and again with 10% aqueous citric acid. The organic layer was then dried with sodium sulfate, filtered and evaporated to an orange foam. The foam was crystallized from acetonitrile (ACN) and the crystals collected by vacuum filtration. Yield 0.52 mmol, 52%.

Example 3

Synthesis of N-α-(Fmoc)-N-ε-(dabcyl)-L-Lysine-PAL-Peg/PS Synthesis Support

The N-α-(Fmoc)-N-ε-(dabcyl)-L-Lysine-OH (Example 2) was used to prepare a synthesis support useful for the preparation of C-terminal dabcylated PNAs. The fluorenylmethoxycarbonyl (Fmoc) group of 0.824 g of commercially available Fmoc-PAL-Peg-PS synthesis support (PerSeptive Biosystems, Inc.; P/N GEN913384) was removed by treatment, in a flow through vessel, with 20% piperidine in DCM for 30 minutes. The support was then washed with DCM. Finally, the support was washed with DMF and dried with a flushing stream of argon.

A solution containing 0.302 g N-α-(Fmoc)-N-ε-(dabcyl)-L-Lysine-OH, 3.25 mL of DMF, 0.173 g (O-(7-azabenzotriaol-1-yl)-1,1,3,3-tetramethyluronium hexafluorophosphate (HATU), 0.101 mL DIEA and 0.068 mL 2,6-lutidine was prepared by sequential combination of the reagents. This solution was then added to the washed synthesis support and allowed to react for 2 hours. The solution was then flushed through the vessel with a stream of argon and the support washed sequentially with DMF, DCM and DMF. The resin was then dried with a stream of argon.

The support was then treated with 5 mL of standard commercially available PNA capping reagent (PerSeptive Biosystems, Inc., P/N GEN063102). The capping reagent was then flushed from the vessel and the support was washed with DMF and DCM. The support was then dried with a stream of argon. Finally, the synthesis support was dried under high vacuum.

Final loading of the support was determined by analysis of Fmoc loading of three samples of approximately 6–8 mg. Analysis determined the loading to be approximately 0.145 mmol/g.

This synthesis support was packed into an empty PNA synthesis column, as needed, and used to prepare PNA oligomers having a C-terminal dabcyl quenching moiety attached to the PNA oligomer through the ε-amino group of the C-terminal L-lysine amino acid.

Example 4

Synthesis of PNA

PNAs were synthesized using commercially available reagents and instrumentation obtained from PerSeptive Biosystems, Inc. Double couplings were routinely performed to improve the quality of the crude product. PNAs possessing a C-terminal dabcyl moiety were prepared by performing the synthesis using the dabcyl-lysine modified synthesis support prepared as described in Example 3 or by labeling the N-ε-amino group of the C-terminal lysine residue while the PNA was still support bound as described in Example 10. All PNAs possessing both an N-terminal fluorescein moiety, as well as, a C-terminal dabcyl moiety were treated with the appropriate labeling reagents and linkers (as required) prior to cleavage from the synthesis support.

Example 5

Preferred Method for Removal of the Fmoc Protecting Group

The synthesis support was treated with a solution of 25% piperidine in DMF for 5–15 minutes at room temperature. After treatment, the synthesis support was washed and dried under high vacuum. The support was then treated with the appropriate labeling reagent and/or cleaved from the synthesis support.

Example 6

Synthesis of Fluorescein-O-Linker

To 7.5 mmol of N-(tert-butyloxycarbonyl)-8-amino-3,6-dioxaoctanoic acid stirring in 10 mL of DCM was added 50 mmol of TFA. The solution was stirred at room temperature until the t-boc group was completely removed. The solvent was then removed by vacuum evaporation and the product was then resuspended in 10 mL of DCM.

To this stirring solution was added, dropwise, a solution containing 7.5 mmol of Di-O-pivaloyl-5(6)-carboxyfluorescein-NHS ester, 30 mmol of N-methylmorpholine (NMM) and 20 mL of DCM. The reaction was allowed to run overnight and was then transferred to a separatory funnel in the morning.

This organic solution was washed with aqueous 10% citric acid two times and then dried with sodium sulfate, filtered and evaporated to a brown foam. The product was column purified using silica gel. A DCM mobile phase and stepwise methanol gradient was used to elute the product from the stationary phase. Yield 2.8 g of foam which was precipitated by dissolution in a minimal amount of DCM and dropwise addition of that solution to hexane. Yield 2.32 g white powder. The purity of the product was not suitable for labeling so an additional reversed phase chromatographic separation was performed on a sample of this material.

One gram of the precipitated product was dissolved in 30 mL of a 50 mM aqueous-triethylammonium acetate (pH 7) containing 40% acetonitrile. This solution was then added to a pre-equilibrated 2 g Waters Sep-Pack Vac 12 cc tC18 cartridge (P/N WAT043380) in 10, 3 mL aliquots. After the addition of all loading solvent, two 3 mL aliquots of 50 mM aqueous triethylammonium acetate (pH 7) containing 40% acetonitrile was loaded as a first wash. Two 3 mL aliquots of 50 mM aqueous triethylammonium acetate (pH 7) containing 60% acetonitrile was then loaded as a second wash. Finally, a single 3 mL aliquot of acetonitrile was used to elute the material remaining on the column. The eluent of each aliquot was collected individually and analyzed by HPLC for purity. The aliquots were vacuum evaporated and the mass of each determined. Fractions of suitable purity were redissolved in DCM, the fractions were combined and precipitated in hexane. Yield 0.232 g.

Example 7

General Procedure for N-Terminal Labeling of Support Bound PNA with Fluorescein-O-Linker For N-terminal fluorescein labeling, the amino terminal fluorenylmethoxycarbonyl (Fmoc) group of several of the fully assembled PNA oligomers was removed by piperidine treatment and the resin was washed and dried under vacuum. The resin was then treated for 20–30 minutes with approximately 300 µL of a solution containing 0.07 M Fluorescein-O-Linker, 0.06 M (HATU), 0.067 M DIEA and 0.1 M 2,6-lutidine. After treatment the resin was washed and dried under high vacuum. The PNA oligomer was then cleaved, deprotected and purified as described below.

Example 8

General Procedure for Labeling of Support Bound PNA with 5(6)Carboxyfluorescein-NHS This method was used as an alternative to the procedure described in Example 7, for labeling PNAs with 5(6)-carboxyfluorescein. This procedure requires that the N-terminus of the PNA oligomer be reacted with Fmoc-8-amino-3,6-dioxaoctanoic acid prior to performing the labeling reaction so that equivalent PNA constructs are prepared. The amino terminal fluorenylmethoxycarbonyl (Fmoc) group of the fully assembled PNA oligomer was removed by piperidine treatment and the synthesis support was washed and dried under vacuum. The synthesis support was then treated for 4–5 hours at 37° C. with approximately 300 µL of a solution containing 0.1M 5(6)carboxyfluorescein-NHS (Molecular Probes, P/N C-1311), 0.3M DIEA and 0.3M 2,6-lutidine. After treatment the synthesis support was washed and dried under high vacuum. The PNA oligomer was then cleaved, deprotected and purified as described below.

More preferably, the synthesis support was then treated for 2–5 hours at 30–37° C. with approximately 250 µL of a solution containing 0.08M 5(6)carboxyfluorescein-NHS, 0.24M DIEA and 0.24M 2,6-lutidine.

Example 9

General Procedure for Labeling of Support Bound PNA with 5(6)Carboxyfluorescein

After proper reaction with linkers and removal of the terminal amine protecting group, the resin was treated with 250 µL of a solution containing 0.5M 5(6) carboxyfluorescein, 0.5M N,N'-diisopropylcarbodiimide, 0.5M 1-hydroxy-7-azabenzotriazole (HOAt) in DMF (See: Weber et al., *Bioorganic & Medicinal Chemistry Letters*, 8: 597–600 (1998). After treatment the synthesis support was washed and dried under high vacuum. The PNA oligomer was then cleaved, deprotected and purified as described below.

Note on Fluorescein Labeling: The fluorescein labeled PNAs described herein were prepared using several different procedures. The different procedures have evolved to optimize fluorescein labeling conditions. At this time we prefer to use the procedure of Weber et al. for most fluorescein labeling operations.

Example 10

General Procedure for Dabcyl Labeling of the N-ε-Amino Group of Support Bound L-Lysine This procedure was used as an alternative to using the prederivatized support when preparing dabcylated PNAs.

This procedure has the advantage that the lysine moiety (and therefore the attached dabcyl moiety) may be placed at any location in the polymer including within the probing nucleobase sequence.

The resin (still in the synthesis column) was treated with 10 mL of a solution containing 1% trifluoroacetic acid, 5% triisopropylsilane (TIS) in dichloromethane by passing the solution through the column over a period of approximately 15 minutes. After treatment, the synthesis support was washed with DMF. Prior to treatment with labeling reagent the support was neutralized by treatment with approximately 10 mL of a solution containing 5% diisopropylethylamine in DMF. After treatment, the support was treated with Dabcyl-NHS (as a substitute for 5(6)carboxyfluorescein-NHS in the procedure) essentially as described in Example 8.

Note: This procedure was only performed on PNA prepared using Fmoc-PAL-PEG/PS (PerSeptive P/N GEN913384). It was not performed with the more acid labile Fmoc-XAL-PEG/PS (PerSeptive P/N GEN913394).

Example 11

General Procedure for Cleavage, Deprotection and Purification

The synthesis support (Fmoc-PAL-PEG/PS; P/N GEN913384) was removed from the synthesis cartridge, transferred to a Ultrafree spin cartridge (Millipore Corp., P/N SE3P230J3) and treated with a solution of TFA/m-cresol (either of 7/3 or 8/2 (preferred)) for 1–3 hours. The solution was spun through the support bed and again the support was treated with a solution of TFA/m-cresol for 1–3 hours. The solution was again spun through the support bed. The combined eluents (TFA/m-cresol) were then precipitated by addition of approximately 1 mL of diethyl ether. The precipitate was pelletized by centrifugation. The pellet was then resuspended in ethyl ether and pelletized two additional times. The dried pellet was then resuspended in 20% aqueous acetonitrile (ACN) containing 0.1% TFA (additional ACN was added as necessary to dissolve the pellet). The product was analyzed and purified using reversed phase chromatographic methods.

Note: Several PNAs were prepared using new product Fmoc-XAL-PEG/PS synthesis support (P/N GEN 913394) available from PerSeptive Biosystems, Inc. This support has the advantage that,the PNA can be removed more rapidly and under more mildly acid conditions. For PNAs prepared with Fmoc-XAL-PEG/PS the support was treated as described above except that a solution of TFA/m-cresol 9/1 was generally used for a period of 10–15 minutes (2x).

Experiment 12

Analysis and Purification of PNA Oligomers

All PNA probes were analyzed and purified by reversed phase HPLC. Probe composition was confirmed by comparison with theoretical calculated masses. The crude products for PNA probes P3 and P4 (Table 5) were prepurified using anion exchange chromatography prior to reversed phase HPLC purification. Anion exchange chromatography generally improved the purity level to better than 70 percent. Sephadex (Pharmacia Biotech) was used as the stationary phase and the mobile phase was 10 mM sodium hydroxide with a sodium chloride gradient.

HPLC Procedures:

Generally, two different high performance liquid chromatography (HPLC) gradients were used to analyze and purify the PNA oligomers (Gradients A & B). Preparative purifications were scaled based on the analytical analysis conditions described in Gradients A & B. Gradient B was developed because initial purification using standard gradients (Gradient A) proved to be less than satisfactory. The experimental conditions are as described below except that some attempts were made to improve purifications by the addition of 20% formamide to the running buffers during some of the purifications. This procedure was abandoned since it did not appear to produce any beneficial results. Curiously however, careful review of the data suggested that the HPLC artifacts previously thought to correlate with the structure of certain probes (See: Provisional Patent Application No. 60/063,283 filed on Oct. 27, 1997) was also found to correlate with the presence of formamide during the purification. Therefore, no correlation is now believed to exist between structure of the PNA probe and the HPLC profiles observed for the purified oligomers.

Gradients A & B

Buffer A=0.1% TFA in water.
Buffer B=0.1% TFA in acetonitrile.
Flow Rate: 0.2 mL/min.
Column Temperature: 60° C.
Instrument: Waters 2690 Alliance: Control by Waters Millennium Software
Stationary Phase: Waters Delta Pak C18, 300 Å, 5 μm, 2×150 mm (P/N WAT023650)
Detection at 260 nm

| Time (min.) | Percent Buffer A | Percent Buffer B | Curve |
|---|---|---|---|
| Gradient Profile A | | | |
| 0.00 | 100 | 0 | 0 |
| 4.00 | 100 | 0 | 6 |
| 22.00 | 80 | 20 | 6 |
| 38.00 | 40 | 60 | 6 |
| 40.00 | 20 | 80 | 11 |
| Gradient Profile B | | | |
| 0.00 | 90 | 10 | 0 |
| 40.00 | 60 | 40 | 6 |
| 50.00 | 20 | 80 | 6 |

Mass Analysis:

Samples were analyzed using a linear Voyager Delayed Extraction Matrix Assisted Laser Desorption Ionization-Time Of Flight (DE MALDI-TOF) Mass spectrometer (PerSeptive Biosystems, Inc.). Sinipinic acid was used as the sample matrix and also used as one point for calibration of the mass axis. Bovine insulin was used as an internal calibration standard for the second calibration point of the mass axis.

Samples were generally prepared for analysis by first preparing a solution of sinipinic acid at a concentration of 10 mg/mL in a 1:2 mixture of acetonitrile and 0.1% aqueous trifluoroacetic acid. Next, an insulin solution was prepared by dissolving 1 mg of bovine insulin (Sigma) in 0.1% aqueous trifluoroacetic acid. Finally, an insulin/matrix solution was then prepared by mixing 9 parts of the sinipHiic acid solution to 1 part of the bovine insulin solution. Samples were prepared for analysis by spotting 1 μL of the insulin/matrix solution followed by spotting 1 μL of diluted sample (approximately 0.1 to 1 OD per mL) onto the mass spectrometer target. The instrument target was allowed to dry before being inserted into the mass spectrometer.

Tables of PNA Oligomers Prepared for Study

TABLE 1

Probes Prepared To Evaluate PNA Molecular Beacons (Hairpins)

| Probe Desc. | CODE[1] | PNA Probe Sequence |
|---|---|---|
| | | *N-terminal Arm Forming Segments* |
| .001 | 5205 | Flu-O-TGG-AGO-OAC-GCC-ACC-AGC-TCC-AK(dabcvl)-NH$_2$ |
| .007 | 5105 | Flu-O-TGG-AGO-ACG-CCA-CCA-GCT-CCA-K(dabcyl)-NH$_2$ |
| .010 | 5005 | Flu-O-TGG-AGA-CGC-CAC-CAG-CTC-CAK(dabcyl)-NH$_2$ |
| .002 | 3203 | Flu-O-TGG-OOA-CGC-CAC-CAG-CTC-CAK(dabcyl)-NH$_2$ |
| .008 | 3103 | Flu-O-TGG-OAC-GCC-ACC-AGC-TCC-AK(dabcyl)-NH$_2$ |
| .009 | 4004[2] | Flu-O-TGG-ACG-CCA-CCA-GCT-CCA-K(dabcyl)-NH$_2$ |
| | | *C-terminal Arm Forming Segments* |
| .018 | 7027 | Flu-O-ACG-CCA-CCA-GCT-CCA-OO-GTG-GCG-T-K(dabcvl)-NH$_2$ |
| .011A | 5025 | Flu-O-ACG-CCA-CCA-GCT-CCA-OOG-GCG-TK(dabcyl)-NH$_2$ |
| .006 | 3023 | Flu-O-ACG-CCA-CCA-GCT-CCA-OOC-GTK(dabcyl)-NH$_2$ |
| | | *Probing Sequence External to the Arm Sequences* |
| .017 | 5115 | Flu-O-TAG-CAO-ACG-CCA-CCA-GCT-CCA-OTG-CTA-K(dabcvl)-NH$_2$ |
| .005 | 3113 | Flu-O-TAG-O-ACG-CCA-CCA-GCT-CCA-O-CTA-K(dabcyl)-NH$_2$ |
| | | *Control Probes; No Arm Forming Segments* |
| .003 | 0000 | Flu-O-ACG-CCA-CCA-GCT-CCA-K(dabcvl)-NH$_2$ |
| .004 | 0110 | Flu-OO-ACG-CCA-CCA-GCT-CCA-OK(dabcyl)-NH$_2$ |

[1]The CODE is a simple means to determine the length of the complementary nucleobases at the amine and carboxyl termini of the PNA polymer and the number and location of any 8-amino-3,6-dioxaoctanoic acid flexible linker units. The probing nucleobase sequence is the same for all probes listed in the table. The first digit in the CODE represents the length of the N-terminal arm segment which is complementary to the C-terminal arm segment. The second digit in the CODE represents the number of flexible linker units which link the N-terminal arm to the probing nucleobase sequence. The third digit in the CODE represents the number of flexible linker units which link the C-terminal arm to the probing nucleobase sequence. The fourth digit in the CODE represents the length of the C-terminal arm segment which is complementary to the N-terminal arm segment. Consequently, the CODE can be used to visually compare the general structure of the different PNA oligomers listed in Table 1.
[2]A coincidental, 4 bp. overlap between the nucleobases at the amine and carboxyl termini are present in this construct instead of the directly comparable 3 bp. overlap.
[3]PNA sequences are written from the amine to the carboxyl terminus. Abbreviations are: Flu = 5-(6)-carboxyfluorescein, dabcyl = 4-((4-(dimethylamino)phenyl)azo)benzoic acid, O = 8-amino-3,6-dioxaoctanoic acid; K = the amino acid L-Lysine

Example 13

Synthesis of DNA Oligonucleotides Prepared for Study

For this study, biotin labeled DNA oligonucleotides suitable as nucleic acids comprising a target sequence which are complementary to the PNA probing nucleobase sequence of the k-ras PNA probes were either synthesized using commercially available reagents and instrumentation or obtained from commercial vendors. All DNAs were purified by conventional methods. The sequences of the DNA oligonucleotides prepared for Examples 14–18 and 20–22 are illustrated in Table 2. Methods and compositions for the synthesis and purification of synthetic DNAs are well known to those of ordinary skill in the art.

TABLE 2

DNA Targets

| Description | Target DNA Sequence | |
|---|---|---|
| wt k-ras | Biotin-GTG-GTA-GTT-GGA-GCT-GGT-GGC-GTA | Seq.Id.No.1 |

TABLE 2-continued

DNA Targets

| Description | Target DNA Sequence | |
|---|---|---|
| mu k-ras | Biotin-GTG-GTA-GTT-GGA-GCT-TGT-GGC-GTA | Seq.Id.No.2 |
| Univ. Comp. | Biotin-ACT-CCT-ACG-GGA-GGC-AGC | Seq.Id.No.3 |

The difference between the wild type (wt) and mutant (mu) target sequences is only a single base (a G to T point mutation. The position of the point mutation is depicted in bold underlined script. These nucleic acid targets are illustrated from the 5' to 3' terminus.

Initial Experimental Analysis of PNA Molecular Beacons

In the initial experiments using a fluorescence detection instrument and PNA oligomers 0.001 and 0.002, it was determined that the PNA constructs have very little intrinsic fluorescence at room temperature. However, upon hybridization of either PNA oligomer to its complementary target sequence, an increasing fluorescent signal was observed.

Example 14

Hybridization Experiments

Amounts of PNA oligomer and target DNA used in this experiment are recorded in Table 3. The PNA oligomer and/or the target DNA was mixed in 20 μl of Hybridization Buffer (50 mM Tris-HCl, pH 8.3; 100 mM NaCl) and heated to 95° C. for 10 minutes. After cooling slowly to room temperature, the mixture was diluted to a total volume of 4 mL (vol. needed in cuvette for measurement). Control samples containing Hybridization Buffer (Hyb. Buffer) and the individual DNA or PNA oligomers were also examined under identical conditions. Additionally, a fluorescein labeled PNA without quencher or arm forming segment was included (Flu-OO-ACG-CCA-CCA-GCT-CC A-NH$_2$; "F-PNA"). The experimental measurements which were recorded are reproduced in Table 3.

With reference to Table 3, there was a low background fluorescence from the individual components of the test system (e.g. hybridization buffer, single stranded DNA, and PNA oligomers). When target DNA and PNA oligomer was mixed and allowed to hybridize, a significant increase in fluorescent signal was detected. Moreover, the intensity of fluorescent signal varied as the relative concentrations of the target DNA and PNA oligomer was altered. Consequently, the data demonstrates that hybridization of the PNA oligomers to the complementary DNA target generated very intense fluorescent signal.

The signal obtained using PNA oligomer 0.002 (3 bp. stem) was between 29 and 83% higher than the signal observed for the PNA oligomer 0.001 (5 bp. stem) (Compare: data in rows 2, 7 and 12 with data in rows, 1, 6 and 11). However, as demonstrated by the greater fluorescent intensity observed for the control probe (F-PNA), the presence of the quenching moiety attached to the PNA oligomer results in a significant quenching effect (Compare: data in rows 3, 13 and 16 with data in rows 1–2, 6–7 and 11–12). Because the fluorescence of the control probe F-PNA was so intense, it was diluted to obtain fluorescent signal which was comparable in intensity to the data obtained using a PNA oligomer having an linked dabcyl quencher moiety. Specifically, the signal obtained with the fluorescein labeled control PNA oligomer (F-PNA) was approximately two to three times the greatest intensity of the signal generated from the PNA oligomers containing a quencher moiety.

TABLE 3

| Row No. | Assay Components | pmol | Ex. L(490) 521 nm |
|---|---|---|---|
| 1 | wt k-ras DNA/PNA .001 | 125/25 | 300 |
| 2 | wt k-ras DNA/PNA .002 | 125/25 | 447 |
| 3 | wt k-ras DNA/F-PNA | 12.5/2.5 | 87 |
| 4 | PNA .001 | 25 | 1 |
| 5 | PNA .002 | 25 | 1 |
| 6 | wt k-ras DNA/PNA .001 | 25/25 | 189 |
| 7 | wt k-ras DNA/PNA .002 | 25/25 | 345 |
| 8 | wt k-ras DNA/F-PNA | 12.5/12.5 | 423 |
| 9 | PNA .001 | 25 | 1 |
| 10 | PNA .002 | 25 | 1 |
| 11 | wt k-ras DNA/PNA .001 | 25/125 | 353 |
| 12 | wt k-ras DNA/PNA .002 | 25/125 | 455 |
| 13 | wt k-ras DNA/F-PNA | 2.5/12.5 | 373 |
| 14 | PNA .001 | 125 | 25 |
| 15 | PNA .002 | 125 | 38 |
| 16 | wt k-ras DNA/F-PNA | 12.5/12.5 | 423 |
| 17 | wt k-ras DNA | 125 | −3 |
| 18 | Hybridization Buffer | — | −5 |

Example 15

Titration of PNA Oligomer with Nucleic Acid Target

In another experiment, 50 pmol of PNA oligomers 0.001 and 0.002 were mixed with differing amounts of nucleic acid target (0–200 pmol) in a total volume of 20 μl of Hyb. Buffer. The mixtures were then heated to 95° C. for 10 minutes and cooled slowly to ambient temperature. The samples were diluted into a total volume of 4 mL and excitation/emission at 493/521.6 nm was recorded using a RF-5000 spectrofluorophotometer (Shimadzu). Results are illustrated graphically in FIG. 1.

With reference to FIG. 1, the fluorescent signal generated from the sample continuously increased with the addition of target sequence until a concentration of 40–60 pmol was present (50 pmol PNA oligomer was used in the assay). There was no significant increase in fluorescent signal as the amount of target sequence was increased between 60–200 pmol. Consequently, the data demonstrates that the signal generated in proportional to the amount of target sequence added, thereby indicating that the production of the signal was caused by the hybridization of the PNA oligomer to the target nucleic acid.

Example 16

Kinetics of Hybridization for PNA Molecular Beacons

In this experiment, 100 pmol (5 μL of 20 pmole/μL) of wt k-ras DNA (ssDNA oligonucleotide) was mixed with 4 mL Hybridization Buffer in a cuvette and adjusted to ambient temperature. Next, 50 pmol (2.5 μL of 20 pmole/μL) of PNA oligomer 0.002, was added and the excitation/emission at 493/521.6 nm was recorded RF-5000 spectrofluorophotometer (Shimadzu). The data obtained is graphically illustrated in FIG. 2.

Figure 2:
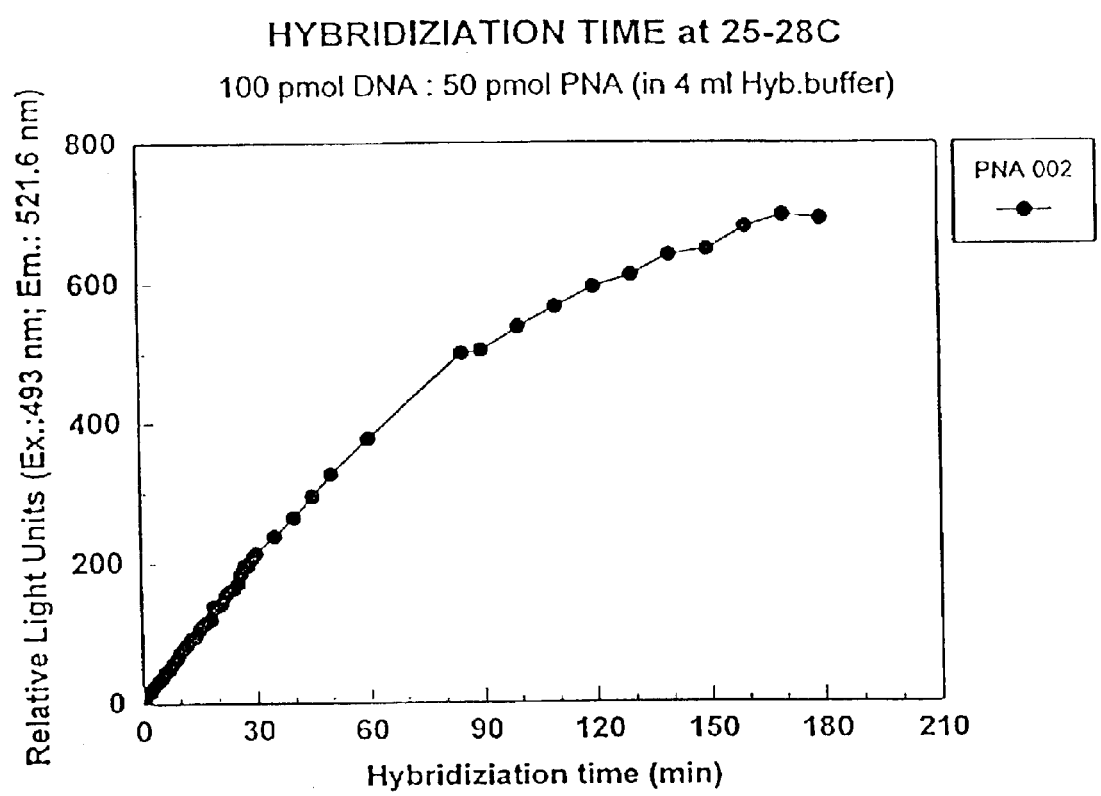
FIG. 2 is a graphical illustration of experimental data.

With reference to FIG. 2, the results demonstrate that the PNA Molecular Beacon hybridizes to the target DNA present in the sample to thereby generate a fluorescent signal with measurable kinetics. The generation of fluorescent signal occurred with an initial rate of 7.2 relative light units (rlu)/minute. After 120 minutes of hybridization the signal was 595 rlu. The kinetic profile of the increase in fluorescent intensity is strongly indicative of hybridization of the PNA oligomer to the target nucleic acid.

Example 17

Hybridization Related to the Composition of the DNA Target

In this experiment, 50 pmol of either wt k-ras or mu k-ras DNA, in hybridization buffer, was mixed with 50 pmol PNA Molecular Beacon 0.001 in hybridization buffer. As a control, 50 pmol of a totally unrelated target DNA oligonucleotide, mixed with 50 pmol of PNA Molecular Beacon 0.001, was also examined (Univ. Comp., See: Table 2). Excitation/emission at 493/521.6 nm was recorded was recorded RF-5000 spectrofluorophotometer (Shimadzu). The results are presented graphically in FIG. 3.

With reference to FIG. 3, the increasing fluorescent intensity observed when mixing PNA 0.001 and the complementary target sequence demonstrates that the PNA Molecular Beacon hybridized to its perfect complement wt k-ras DNA. The rate of fluorescent signal generation and the maximal fluorescent signal generated was significantly lower for the sample when the non-complementary mu k-ras DNA (having a single point mutation as compared with the wild type target) was substituted in the assay. Furthermore, mixing a totally unrelated nucleic acid sequence (Univ. Comp) with PNA Molecular Beacon 0.001 did not produce any fluorescent signal, even after heating the sample to 95° C. Consequently, the data strongly demonstrates that the generation of the fluorescent signal in the assay was directly related to the sequence specific interactions between the PNA Molecular Beacon and the nucleic acid present in the sample.

Example 18

Effect of Blocking Probes on Sequence Discrimination

This experiment was designed to increase discrimination of the PNA oligomer 0.001 by introducing some unlabeled "blocking PNA" into the hybridization mixture. This "blocking PNA" has a sequence complementary to the mu k-ras DNA and should, therefore, effectively compete with the labeled PNA oligomer 0.001 for binding to the non-target mu k-ras DNA. The unlabeled "blocking PNA" had the sequence:

Blocking PNA: H-ACG-CCA-CAA-GCT-CCA-NH$_2$

In this experiment, 50 pmol of wt k-ras or mu k-ras DNA was mixed with 50 pmol PNA oligomer 0.001. To one pair of reactions was added 500 pmol "blocking PNA" (data in Table 4, row 2). The samples were heated to 95° C. and then cooled slowly to RT. Excitation/emission at 493/521.6 nm were recorded. The results obtained are reproduced in Table 4.

With reference to Table 4, in the absence of blocker PNA there is a 2 fold difference (discrimination factor) between the fluorescent signal generated when the PNA oligomer hybridizes to the perfectly complementary wt k-ras DNA as compared with signal generated upon hybridization to non-complementary mutant k-ras DNA (single point mutation). Addition of "blocking PNA" increases the discrimination of the assay by approximately 10 fold (Compare data in Table 4, the discrimination factor (DF) is increased to 19.6 from 2). This increase in discrimination occurred despite an approximately 50% reduction in the signal generated by hybridization to the complementary wt k-ras DNA. However, as demonstrated by analysis of the data in Table 4, hybridization of the PNA probe to the non-complementary mu k-ras DNA was effectively eliminated in the presence of the "blocking PNA". Consequently, the data again strongly illustrates that the generation of fluorescent signal was directly related to the sequence specific hybridization of the nucleic acid to the PNA oligomer. The data further demonstrates the utility of using blocking probes to enhance sequence discrimination in nucleic acid hybridization assays when utilizing PNA Molecular Beacons.

TABLE 4

| Row No. | Conditions | wt k-ras DNA/ PNA .001 | mu k-ras DNA/ PNA .001 | DF |
| --- | --- | --- | --- | --- |
| 1 | 0 pmol Blocking PNA | 541 | 271 | 2 |
| 2 | 500 pmol Blocking PNA | 255 | 13 | 19.6 |

Conclusions from the Initial Experimental Data:

PNA Molecular Beacons can be prepared. They have low intrinsic fluorescent intensity until hybridized to a complementary or substantially complementary target nucleic acid. Non-specific interactions can be eliminated, if desired, using a "blocking PNA". Thus, we have demonstrated that it is possible to prepare functional PNA Molecular Beacons which exhibit a good specificity which can be further enhance by the application of "blocker probes". Consequently, the PNA oligomer constructs investigated in these initial experiments demonstrate the effective use of PNA Molecular Beacons in probe-based hybridization assays.

Example 19

Structural Analysis of PNA Hairpins and Multimers

The reference entitled "Hairpin-Forming Peptide Nucleic Acid Oligomers", Armitage et al., *Biochemistry*, 37: 9417–9425 (1998) is admitted as prior art to this Example 19 only. It has been recently reported in the scientific literature that PNAs form hairpin structures (See: Armitage et al.). Using the hairpin forming PNA (referred to as "PNA1" in the reference (See: Scheme 3: col. 1, p. 9419), hereinafter referred to as "PNAD") described in the literature as a model, numerous PNA and analogous DNA oligomers were prepared and their properties examined in order to obtain a basis for understanding the physical behavior of PNA hairpins and multimers. We anticipated this would allow us to better interpret the results reported in our priority application (U.S. Ser. No. 08/958532). The data presented in this Example 19 demonstrates that PNA hairpins will form if designed to have long stems (e.g. 9 subunits). However PNA hairpins having shorter stems (e.g. 6 subunits) do not form hairpins as readily as their DNA counterparts. Furthermore, applicants have observed that the formation and stability of a PNA hairpin is not substantially affected by the presence or absence of magnesium or the ionic strength of the buffer as are DNA hairpins (See Tyagi et al., Nature Biotechnology, 14: 303–308 (1996) at p. 305, col. 1, lns 1–16). Nevertheless, PNA hairpins having stem duplexes of 9 subunits in length exhibit poor signal to noise ratios (less than 4 to 1) upon melting and, contrary to the findings of Armitage et al., do not appear to substantially hybridize to complementary nucleic acid. Consequently, PNA hairpins which have long stems (e.g. 7 or greater subunits), do not appear to be ideally suited for the analysis of nucleic acids.
Materials and Methods:
Probes PNAs were prepared and purified as described herein. Labeled and unlabeled DNA oligonucleotides were synthesized using commercially available reagents and instrumentation. Dabcylated DNAs were prepared using the dabcyl synthesis support available from Glen Research (P/N 20-5911) and other commercially available DNA reagents and instrumentation. The Fluoredite phosphoramidite (PerSeptive Biosystems, Inc., P/N GEN080110) was used to label DNAs with 5(6)carboxyfluorescein. All DNAs were purified by conventional methods. The DNA and PNA probe compositions are presented in Table 5. Tm data for DNA probes is summarized in Table 6 and the Tm data for PNA probes is summarized in Table 7. Tm data for both the melting "M" and the reannealing "R" is presented in Table 6 and 7.

Preparation of Dilution Series of PNA and DNA Probes for Tm Analysis

Purified PNA probes were dissolved in 1:1 DMF/$H_2O$ at 0.05 OD (260 nm ) per 20 $\mu L$ to prepare the PNA Probe Stock. Purified DNA probes were dissolved in 4:1 $H_2O$/acetonitrile at 0.05 OD (260 nm) per 20 ǁL to prepare the DNA Probe Stock. Based on calculated extinction coefficients, the appropriate amount of PNA Probe Stock or DNA Probe Stock was added to 5 ml of Tm Buffer (10 mM sodium phosphate, pH 7.0) to prepare a solution of approximately 7.5 $\mu M$ of the one or two oligomers needed to perform the Tm analysis of the unimolecular or bimolecular system. From this solution was taken 2.5 mL which was added to 2.5 mL of Tm buffer to thereby prepare the second concentration of a dilution series of Tm Samples. The remaining 2.5 mL of the first sample was used for Tm analysis. Serial dilution the samples in Tm Buffer was continued in this fashion until 2.5 mL of Tm Samples at concentrations of approximately 7.5 $\mu M$, 3.75 $\mu M$, 1.87 $\mu M$, 0.94 $\mu M$ and 0.468 $\mu M$ (5 mL) were prepared. A Tm analysis of these solutions was then performed as described below.
Tm Analysis 1. Tm Buffer:

The five Tm Samples of a dilution series of a particular unimolecular or bimolecular system to be analyzed were simultaneously examined using a Cary 100 Bio UV-Visible Spectrophotometer (Varian Instruments) equipped with a 6×6 thermostatable multicell block running Win UV Bio application software package. To a 10×10 UV cell (Starna Cells, P/N 21-Q-10) was added a 7.2 mm stir bar and the 2.5 mL of each sample of the dilution series. The stirring accessory was used during all analysis. All samples were thermally denatured and reannealed prior to data collection by having the instrument rapidly ramp the temperature to a point above the melting temperature and then holding that temperature for 5–10 minutes before returning to the starting temperature. Data for both dissociation and reannealing was collected and analyzed. The temperature range over which data was collected was varied in response to the expected Tm which was roughly determined during the premelt and prereannealing step. Regardless of the temperature range, the temperature ramp rate for both dissociation and reannealing was always 0.5° C./min. The absorbance (260 nm, averaged over a 3 second collection) was plotted vs. the temperature of the multicell block.

2. Tm Buffer and 1 mM $MgCl_2$:

After the Tm analysis was performed in Tm Buffer, to each cell was added 0.5 $\mu L$ of 5M $MgCl_2$ to thereby prepare a sample containing 1 mM $MgCl_2$. The dilution effect was considered to be negligible. The Tm analysis was then performed again to determine whether the presence of $MgCl_2$ had any effect on the Tm of the unimolecular or bimolecular system.

3. Tm Buffer, 1 mM $MgCl_2$ and 100 mM NaCl:

After the Tm analysis was performed in Tm Buffer and 1 mM $MgCl_2$, to each cell was added 42 $\mu L$ of saturated NaCl (approximately 6.11 M/L). The dilution effect was again considered to be negligible. The Tm analysis was then performed again to determine whether the presence of approximately 100 mM NaCl had any effect on the Tm of the unimolecular or bimolecular system.
Results and Discussion:

With reference to Table 5, the sequences of complementary labeled PNA probes P1 and P2 are illustrated. These probes hybridize to form a 9 subunit duplex identical to the stem duplex formed in PNA hairpins, P3 and P4. Therefore, P1 and P2 form a bimolecular system for comparison with the unimolecular PNAs, P3 and P4. Probes P3 and P4 differ only in that the subunits which form the loop of P4 have been replaced with flexible linkages in P3. Unlabeled versions of all four PNA probes have likewise been prepared so as to understand the effects of labels on Tm. In Table 5, the unlabeled probes are designated with an "N" for no label.

Also prepared for comparison is the PNA probe "PNAD" which Armitage et al. teach will form a hairpin. Applicants have also prepared a version of the PNAD probe which possess arm segments of 6 subunits (PNAD 6S) as compared with the 9 subunits self complementary arm segments of the PNAD probe. The PNA probe P5 is complementary to the DNA probe D5B. This bimolecular complex was prepared to determine its Tm since Armitage et al. teach that this short 12-mer nucleic acid sequence will hybridize to the PNAD probe thereby opening the 9 subunit stem.

TABLE 5

| Probe Sequence | Sequence ID | Seq Id. No. |
|---|---|---|
| Peptide Nucleic Acid Probes | | |
| Flu-O-ATA-TAT-TGG-EE-$NH_2$ | P1 | |
| Ac-O-ATA-TAT-TGG-EE-$NH_2$ | P1N | |
| Ac-EE-CCA-ATA-TAT-K(dabcyl)-$NH_2$ | P2 | |
| Ac-EE-CCA-ATA-TAT-$NH_2$ | P2N | |

TABLE 5-continued

| Probe Sequence | Sequence ID | Seq Id. No. |
|---|---|---|
| Flu-OEE-ATA-TAT-TGG-OO-CCA-ATA-TAT-EE-K(dabcyl)-NH₂ | P3 | |
| H₂N-OEE-ATA-TAT-TGG-OO-CCA-ATA-TAT-EEK-NH₂ | P3N | |
| Flu-OEE-ATA-TAT-TGG-CTG-ATC-CAA-TAT-AT-EE-K(dabcyl)-NH₂ | P4 | |
| H₂N-OEE-ATA-TAT-TGG-CTG-ATC-CAA-TAT-AT-EEK-NH₂ | P4N | |
| H₂N-ATA-TAT-TGG-CTG-ATC-CAA-TAT-AT-KK-NH₂ | PNAD | |
| H₂N-TAT-TGG-CTG-ATC-CAA-TA-KK-NH₂ | PNAD 6S | |
| H₂N-TTG-GCT-GAT-CCA-NH₂ | P5 | |
| Synthetic Oligodeoxynucleotides | | |
| Flu-ATA-TAT-TGG-OH | D1 | Seq. Id. No. 4 |
| HO-ATA-TAT-TGG-OH | D1N | Seq. Id. No. 5 |
| HO-CCA-ATA-TAT-(dabcyl) | D2 | Seq. Id. No. 6 |
| HO-CCA-ATA-TAT-OH | D2N | Seq. Id. No. 7 |
| Flu-ATA-TAT-TGG-(spacer)-CCA-ATA-TAT-dabcyl | D3 | Seq. Id. No. 8 |
| HO-ATA-TAT-TGG-(spacer)-CCA-ATA-TAT-OH | D3N | Seq. Id. No. 9 |
| Flu-ATA-TAT-TGG-CTG-ATC-CAA-TAT-AT-dabcyl | D4 | Seq. Id. No. 10 |
| HO-ATA-TAT-TGG-CTG-ATC-CAA-TAT-AT-OH | D4N | Seq. Id. No. 11 |
| Bio-TGG-ATC-AGC-CAA-OH | D5B | Seq. Id. No. 12 |
| HO-ATA-TAT-TGG-ATC-AGC-CAA-TAT-AT-OH | D6 | Seq. Id. No. 13 |

PNA sequences are written from the amine to the carboxyl terminus.
DNA sequences are written from the 5' to 3'.
Abbreviations are:
Flu = 5-(6)-carboxyfluorescein, dabcyl = 4-((4-(dimethylamino)phenyl)azo)benzoic acid,
O = 8-amino-3,6-dioxaoctanoic acid;
K = the amino acid L-Lysine and
"E" is the Solubility Enhancer "compound "4" which has been described in: Gildea et al., Tett. Lett. 39 (1998) 7255–7258.
The "spacer" used for the DNAs was commercially available C3 spacer phosphoramidite Glen Research (P/N 10-1913 ).

With reference to Table 5, the sequences for the synthetic oligodeoxynucleotides prepared for examination are also illustrated. DNAs which were conceptually the most equivalent labeled and unlabeled versions of P1, P2, P3, P4, P1N, P2N, P3N and P4N were prepared for comparison. As discussed, D5B is a complement to P5 and D6 is the complement to D4, P4 and PNAD.

TABLE 6

| | UV Tm Analysis | | | | | | | | | |
|---|---|---|---|---|---|---|---|---|---|---|
| | [1] | | [2] | | [3] | | [4] | | [5] | |
| Probes (Conditions) | M | R | M | R | M | R | M | R | M | R |
| D1N/D2N (Buf) | <10 | <10 | <10 | <10 | <10 | <10 | <10 | <10 | <10 | <10 |
| D1N/D2N (Buf, Mg) | 17.1 | 16.8 | 14.6 | 14.8 | 14.0 | 13.4 | 11.4 | 11.7 | <10 | <10 |
| D1N/D2N (Buf, Mg & Na) | 22.3 | 21.7 | 20.7 | 18.9 | 19.0 | 18.2 | 15.0 | 15.0 | 14.2 | 13.4 |
| D1/D2 (Buf) | 15.0 | 14.8 | 13.5 | 13.3 | 12.0 | 12.9 | 11.5 | 9.9 | <10 | <10 |
| D1/D2 (Buf, Mg) | 24.1 | 23.8 | 22.0 | 21.8 | 21.0 | 20.9 | 19.5 | 19.9 | 16.5 | 17.9 |
| D1/D2 (Buf, Mg & Na) | 29.0 | 28.4 | 27.5 | 26.4 | 26.0 | 25.5 | 23.4 | 23.0 | 21.4 | 20.0 |
| D3N (Buf) | 40.0 | 40.5 | 40.5 | 40.5 | 40.5 | 40.5 | 40.5 | 41.2 | 40.5 | 41.2 |
| D3N (Buf, Mg) | 44.6 | 44.7 | 44.6 | 45.3 | 44.6 | 44.8 | 45.5 | 45.4 | 45.5 | 44.9 |
| D3N (Buf, Mg & Na) | 48.1 | 48.3 | 48.6 | 48.8 | 49.0 | 49.4 | 48.5 | 49.5 | 48.0 | 48.6 |
| D3 (Buf) | 43.7 | 43.6 | 44.3 | 44.1 | 44.3 | 44.6 | 43.9 | 44.0 | 43.9 | 44.0 |
| D3 (Buf, Mg) | 50.6 | 49.9 | 50.6 | 49.9 | 51.1 | 50.5 | 51.0 | 50.5 | 51.5 | 51.1 |
| D3 (Buf, Mg & Na) | 54.1 | 53.8 | 55.6 | 53.8 | 54.6 | 54.0 | 54.5 | 54.5 | 54.5 | 54.1 |

TABLE 6-continued

| | UV Tm Analysis | | | | | | | | | |
|---|---|---|---|---|---|---|---|---|---|---|
| | [1] | | [2] | | [3] | | [4] | | [5] | |
| Probes (Conditions) | M | R | M | R | M | R | M | R | M | R |
| D4N (Buf) | 41.6 | 41.7 | 42.1 | 42.2 | 42.5 | 42.3 | 42.5 | 42.8 | 42.0 | 43.4 |
| D4N (Buf, Mg) | 51.6 | 51.2 | 52.1 | 52.3 | 52.5 | 52.4 | 52.5 | 53.5 | 52.5 | 53.0 |
| D4N (Buf, Mg & Na) | 54.1 | 54.4 | 55.1 | 54.9 | 55.1 | 55.0 | 55.0 | 55.0 | 55.0 | 55.1 |
| D4 (Buf) | 45.2 | 43.4 | 45.6 | 44.9 | 45.6 | 45.0 | 45.5 | 44.5 | 45.5 | 44.1 |
| D4 (Buf, Mg) | 54.6 | 53.9 | 55.5 | 55.0 | 55.5 | 55.0 | 54.5 | 54.1 | 55.0 | 54.6 |
| D4 (Buf, Mg & Na) | 57.1 | 56.5 | 57.5 | 57.5 | 58.0 | 57.5 | 58.5 | 57.6 | 58.0 | 57.6 |

With reference to Table 6, the Tm for the labeled and unlabeled bimolecular systems D1/D2 and D1N/D2N, respectively, are concentration dependent as can be seen by the 8–10° C. difference between the most and least concentrated samples where Tm data is available. The low and unmeasurable Tm values under conditions of low ionic strength are expected for such a short nucleic acid duplex. However, there is a remarkable stabilizing effect of approximately 7° C. due to the presence of the dabcyl/fluorescein labels as can be seen by comparison of the Tm values at all concentrations and under all conditions examined. This was a very surprising result.

The Tm of labeled (D3 and D4) and unlabeled (D3N and D4N) unimolecular probes exhibited a concentration independent Tm. Consequently, the data indicates that these DNAs exist as hairpins in solution. As taught by Tyagi et al., the hairpin stem duplex of these DNA probes is substantially stabilized by both the addition of magnesium and an increase in ionic strength (See: Tyagi et al. *Nature Biotechnology*, 14: 303–308 (1996) at p. 305, lns. 1–16). Surprisingly the stem duplex D4 (which contained a polynucleotide loop) was more stable under all conditions examined than was the stem duplex of D3 which contained a flexible linkage. Also noteworthy is the stabilizing effect attributable to the fluorescein/dabcyl pair. For D4 the stabilizing effect is approximately 3–4° C. whereas it is approximately 5–6° C. for D3. Thus, the data indicates that as the Tm of the stem duplex increases there is less of a stabilizing effect attributable to the dabcyl/fluorescein interactions. Nevertheless, this observation is very surprising and suggests that the interaction between the dyes is very strong.

TABLE 7

| | UV Tm Analysis | | | | | | | | | |
|---|---|---|---|---|---|---|---|---|---|---|
| | [1] | | [2] | | [3] | | [4] | | [5] | |
| Probes (Conditions) | M | R | M | R | M | R | M | R | M | R |
| P1N/P2N (Buf) | 57.1 | 56.5 | 55.0 | 54.6 | 53.0 | 52.6 | 51.5 | 50.6 | 48.5 | 48.7 |
| P1N/P2N (Buf, Mg) | 57.1 | 56.4 | 55.1 | 54.5 | 53.0 | 53.0 | 51.0 | 50.5 | 49.0 | 48.6 |
| P1N/P2N (Buf, Mg & Na) | 57.6 | 57.0 | 55.4 | 55.1 | 53.5 | 53.1 | 52.0 | 51.1 | 49.5 | 49.2 |
| P1/P2 (Buf) | 61.1 | 60.4 | 59.1 | 58.5 | 57.0 | 57.0 | 55.5 | 54.5 | 51.5 | 52.6 |
| P1/P2 (Buf, Mg) | 61.1 | 60.4 | 59.1 | 59.0 | 57.5 | 57.0 | 55.5 | 55.0 | 52.5 | 53.1 |
| P1/P2 (Buf, Mg & Na) | 61.5 | 60.9 | 59.6 | 59.5 | 58.0 | 57.0 | 56.0 | 55.5 | 54.0 | 53.6 |
| P3N (Buf) | 82.6 | 82.3 | 82.5 | 82.4 | 83.0 | 82.4 | 83.0 | 82.5 | 83.0 | 82.6 |
| P3N (Buf, Mg) | 83.1 | 82.4 | 83.1 | 81.9 | 83.0 | 82.5 | 83.0 | 83.1 | 83.0 | 82.6 |
| P3N (Buf, Mg & Na) | 83.1 | 82.9 | 83.1 | 81.4 | 83.5 | 82.9 | 83.5 | 83.0 | 83.5 | 83.1 |
| P3 (Buf) | 82.1 | 81.9 | 82.6 | 82.0 | 82.6 | 82.0 | 83.0 | 82.6 | 82.0 | 81.6 |
| P3 (Buf, Mg) | 82.1 | 81.8 | 82.1 | 81.8 | 82.5 | 82.4 | 82.5 | 82.0 | 83.0 | 83.5 |
| P3 (Buf, Mg & Na) | 83.1 | 82.9 | 83.5 | 83.0 | 84.0 | 83.0 | 83.5 | 83.0 | 83.5 | nd |
| P4N (Buf) | 81.6 | 81.4 | 82.1 | 81.5 | 82.1 | 81.5 | 82.5 | 81.1 | 82.0 | 80.1 |
| P4N (Buf, Mg) | 81.6 | 81.3 | 81.6 | 81.3 | 82.1 | 81.4 | 82.0 | nd | 82.0 | 81.1 |
| P4N (Buf, Mg & Na) | 82.1 | 82.3 | 82.1 | 82.3 | 82.5 | nd | 82.0 | 82.0 | 84.0 | 81.6 |
| P4 (Buf) | 81.6 | 80.9 | 81.6 | 81.4 | 82.1 | 81.5 | 82.0 | 81.5 | 81.5 | 81.1 |
| P4 (Buf, Mg) | 81.6 | 81.0 | 81.6 | 81.5 | 82.0 | 81.5 | 82.0 | 81.1 | 82.0 | 81.6 |
| P4 (Buf, Mg & Na) | 82.6 | 81.8 | 82.6 | 82.4 | 82.6 | 82.5 | 82.5 | 82.5 | 83.0 | 82.1 |
| PNAD (Buf) | 81.1 | 80.4 | 81.1 | 81.0 | 82.0 | 81.0 | 81.5 | 81.5 | 81.5 | 81.1 |
| PNAD (Buf, Mg) | 80.6 | 80.3 | 81.1 | 80.4 | 81.1 | 80.4 | 80.5 | 81.0 | 80.5 | 80.5 |
| PNAD (Buf, Mg & Na) | 80.6 | 80.4 | 81.5 | nd | 81.0 | 81.4 | 81.5 | 80.5 | 82.1 | 80.6 |
| PNAD 6S (Buf) | 75.0 | 74.6 | 75.0 | 74.1 | 74.5 | 73.5 | 73.5 | 65.5 | 67.5 | 57.5 | nd = not determinable

With reference to Table 7, Tm data for the PNA constructs is presented. The Tm values for the PNAs are substantially higher than for the comparable DNAs. Both the labeled (P1/P2) and unlabeled (P1N/P2N) bimolecular systems exhibited Tms which were concentration dependent as is evident by the 8–10° C. difference in Tm between the most and least concentrated samples. Again there was a increase of approximately 3–4° C. in Tm which was attributable to the presence of the fluorescein/dabcyl moieties. Though clearly dependent upon concentration, the stability of the duplexes were not substantially affected by the presence or absence of magnesium or the ionic strength of the buffer since there was no substantial difference in Tm under any of the three conditions examined. Most importantly no substantial hysteresis was observed in the analysis of labeled or unlabeled PNA bimolecular systems even at the lowest concentration examined. The lack of hysteresis indicates that the duplex reforms readily.

Figure 4A:
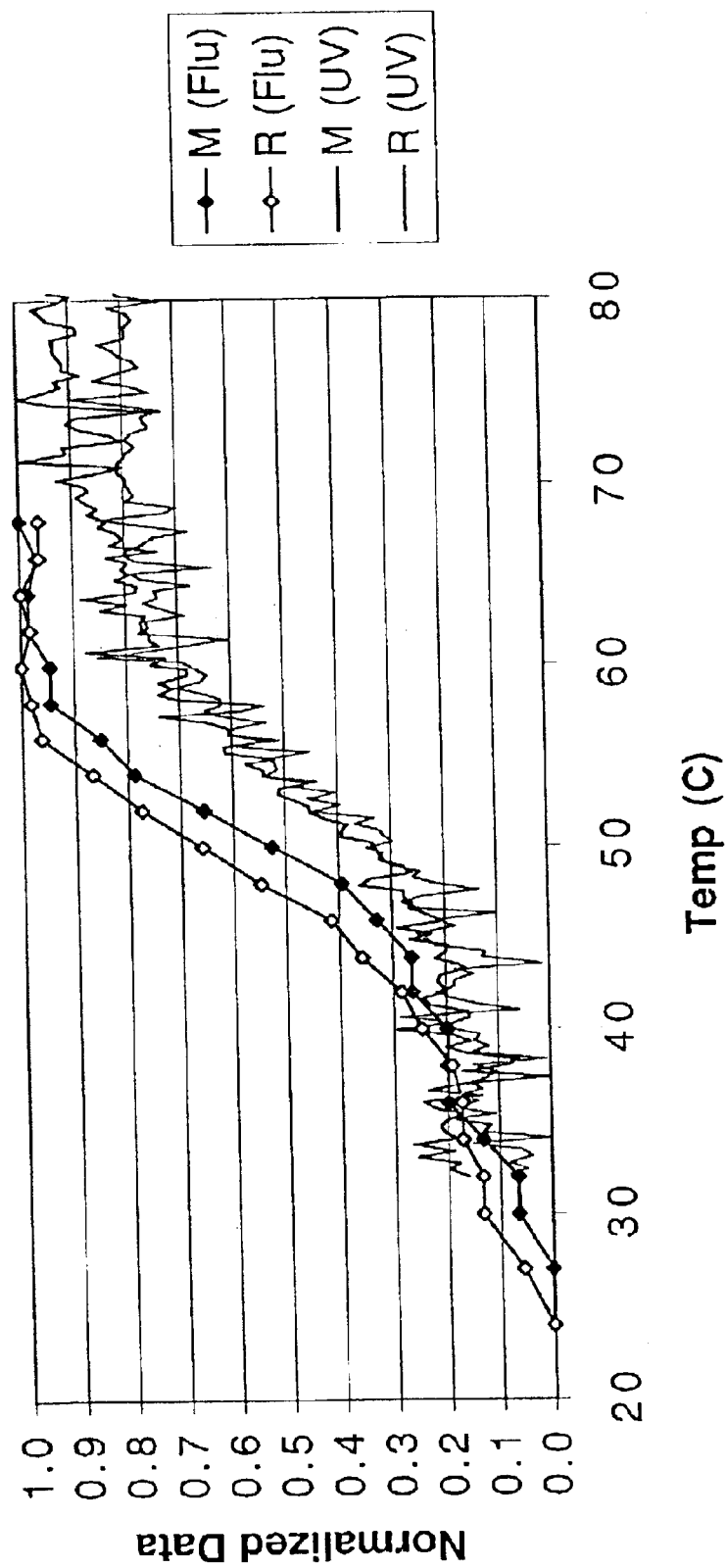
FIG. 4A is an overlay of normalized fluorescence vs. temperature and absorbance vs. temperature plots for a labeled PNA/PNA bimolecular duplex.

For comparison, fluorescence analysis of the least concentrated sample of the P1/P2 bimolecular system was performed. The least concentrated sample (sample at [5] which had 1 mM $MgCl_2$ and 100 mM NaCl) was analyzed for fluorescence essentially as described in Example 20, below, except that excitation was at 415 nm and emission was recorded at 520 nm. Normalized data for fluorescence vs. temperature and absorbance vs. temperature are overlaid in FIG. 4A. Though the shape of the curves is similar the data is not superimposible. A similar result was observed when the absorbance vs. temperature and fluorescence vs. temperature data for the D1/D2 system was overlaid (data not shown). The structural basis for this lack of superimposibility is not known but appears to be consistent for the bimolecular systems.

Both the labeled and unlabeled versions of P3 and P4 exhibited a concentration independent Tm. Consequently, the data indicates that these PNAs form hairpins in solution. Likewise, the probe PNAD also was confirmed to exhibit a concentration independent Tm of approximately 81–82° C., as had been reported by Amitage et al. The data clearly demonstrates that the stem duplex of a PNA hairpin is not substantially affected by the presence or absence of magnesium or the increase in ionic strength since the Tm for the probes are the same without regard to the buffer composition in which the Tm analysis was performed. Curiously there was no substantial difference in the Tm of labeled as compared with unlabeled probes. However, it is believed that the Tm of these duplexes is so high that the fluorescein/dabcyl interactions cannot be maintained.

Figure 4B:
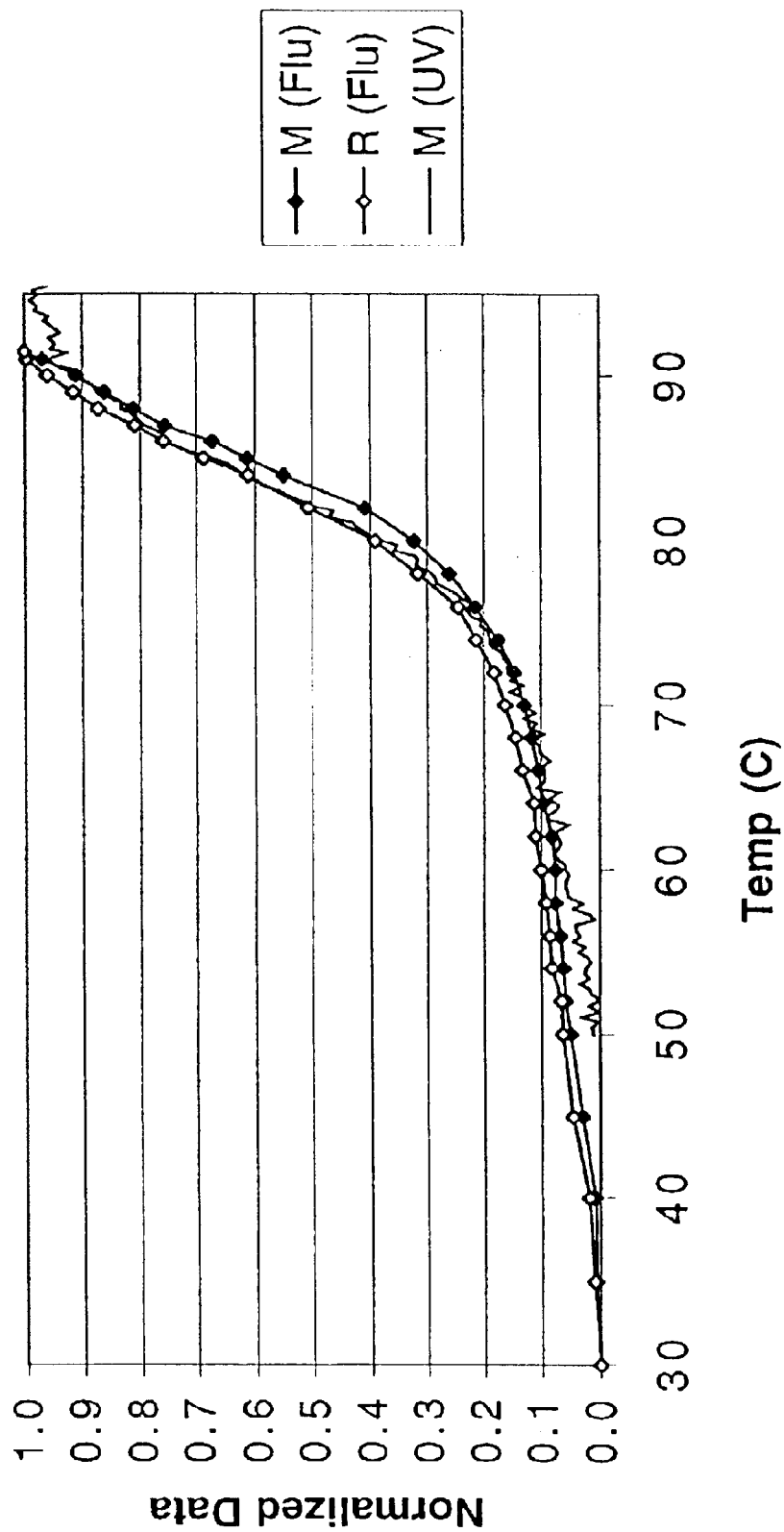
FIG. 4B is an overlay of normalized fluorescence vs. temperature and absorbance vs. temperature plots for a labeled unimolecular PNA probe comprising a flexible linkage.
Figure 4C:
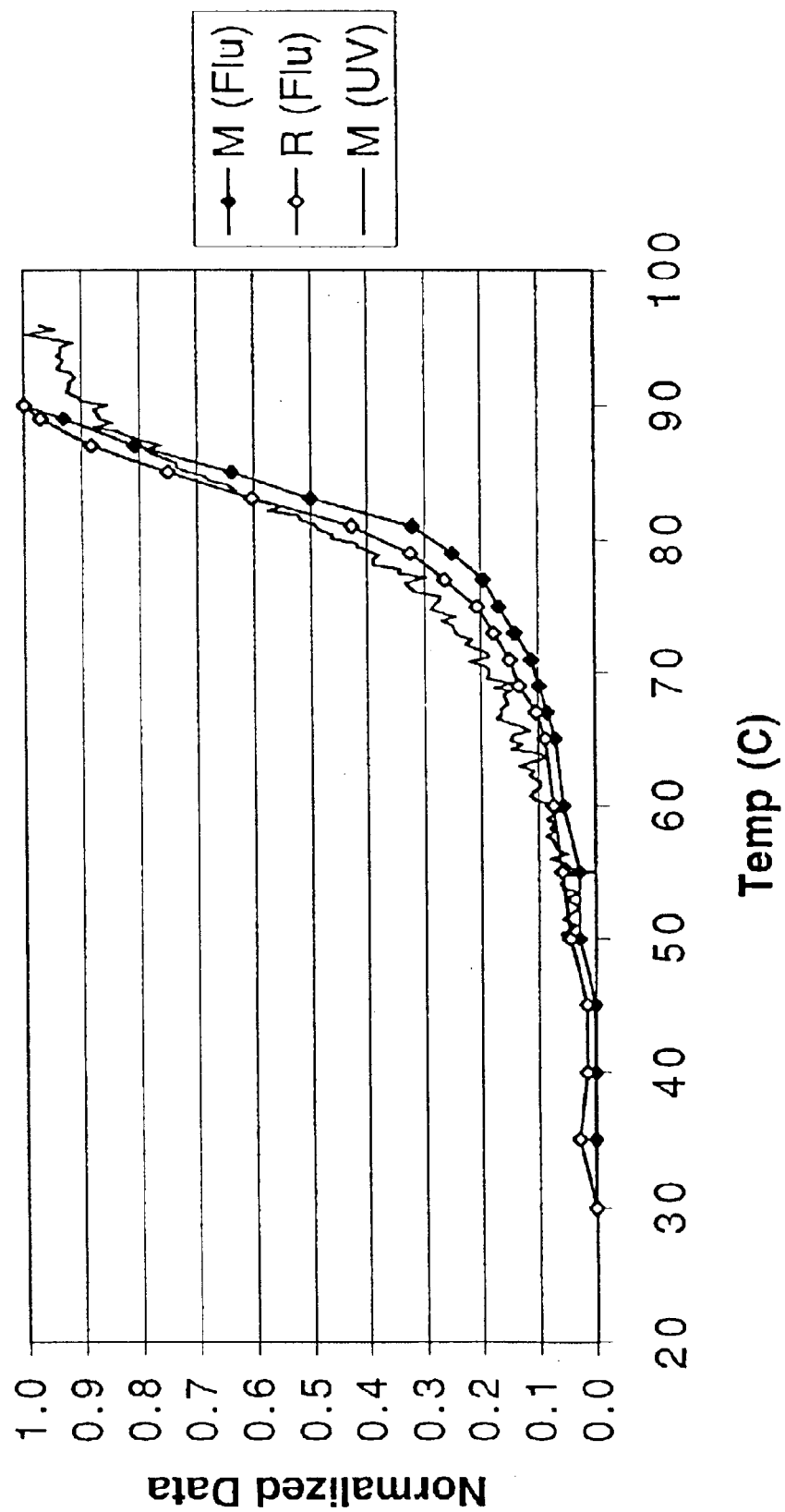
FIG. 4C is an overlay of normalized fluorescence vs. temperature and absorbance vs. temperature plots for a labeled unimolecular PNA probe which is continuous from the N- to C-terminus.

As with the P1/P2 and D1/D2 bimolecular systems, fluorescence vs. temperature analysis of the least concentrated samples (each probe at [5] which had 1 mM $MgCl_2$ and 100 mM NaCl) of both probes P3 and P4 were performed. With reference to FIGS. 4B and 4C, normalized fluorescence vs. temperature and absorbance vs. temperature data are overlaid for P3 and P4, respectively. Unlike the bimolecular system, the fluorescence vs. temperature and absorbance vs. temperature data for both P3 and P4 are superimposible. Data was also collected for the D3 and D4 unimolecular probes. The data for these unimolecular probes was also found to be highly superimposible (data not shown) thereby indicating they result from the same physical transition of the probe. Taken as a whole, the excellent correlation between the fluorescence vs. temperature and absorbance vs. temperature data in both the DNA and PNA unimolecular systems strongly indicates that increases in absorbance and fluorescence occur as result of a helix to coil transition.

Using the data obtained from melting and reannealing of D1/D2, D3, D4, P1/P2, P3 and P4 as described above, the difference between the lowest (helix) and highest (coil) fluorescence intensities recorded were calculated to determine the signal to noise value for each probe. This was intended to give an estimate of the potential increase in signal which could be expected in a hybridization assay wherein the stern of the probe was opened. In FIG. 5, the fluorescence signal to noise ratios for melting and reannealing the PNA and DNA bimolecular and unimolecular systems is presented. Most striking is the significantly lower signal to noise ratio for all the PNA systems as compared with the DNA systems. The low signal to noise ratio is consistent with the data presented by Armitage et al. though it is not clear that the labeled probes of Armitage et al. form hairpins. Nevertheless, the low signal to noise ratios for the PNA probes comprising long self-complementary arm segments suggests that these constructs are not optimal for analysis of nucleic acids.

Figure 6:
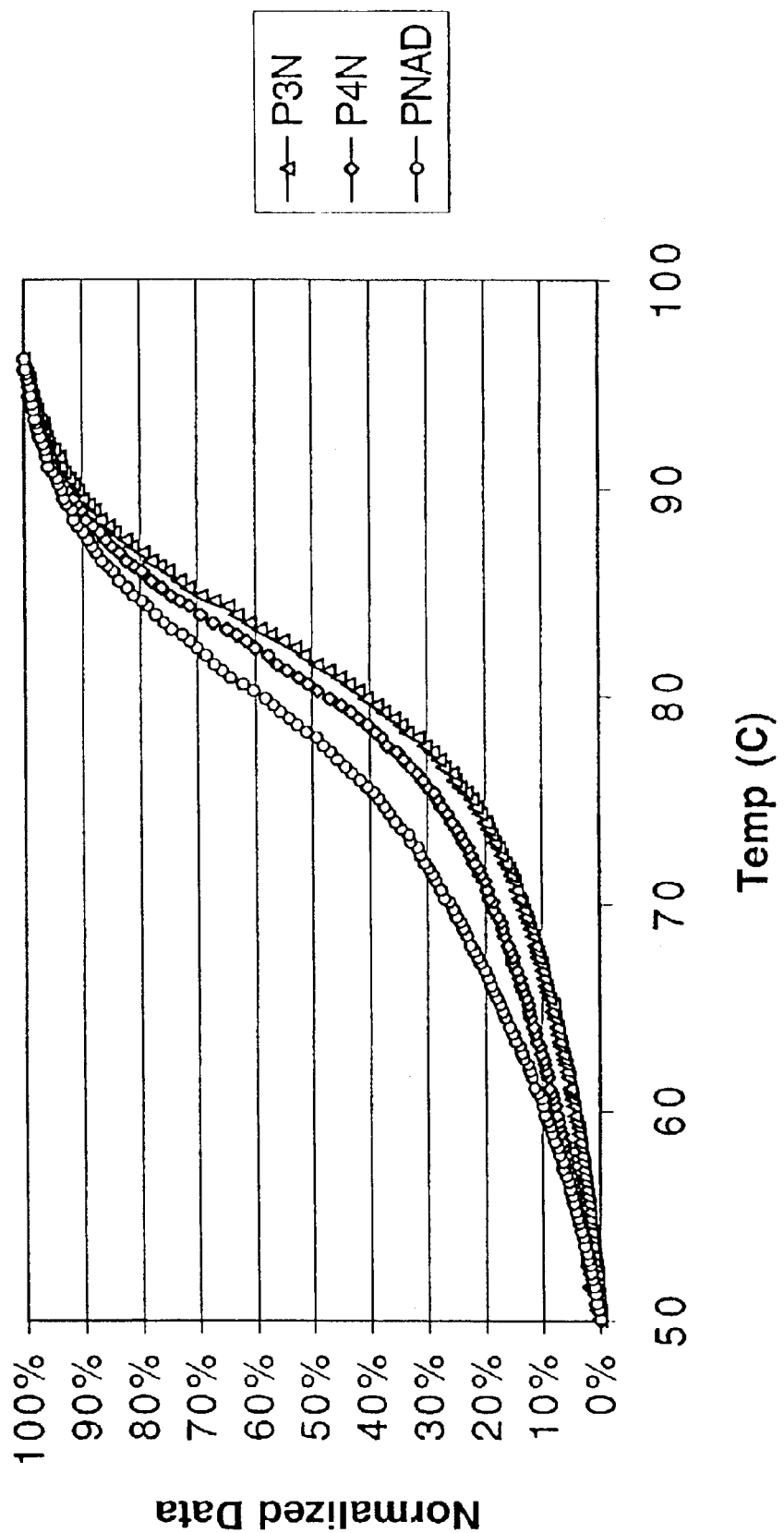
FIG. 6 is an overlay of normalized absorbance vs. temperature plots for three similar PNA unimolecular probes.

Though the Tm of labeled and unlabeled hairpins having an identical 9 bp stem duplex where all very similar (approximately 81–83° C.), normalized data presented in FIG. 6 demonstrates that several factors can influence thermodynamic parameters of the stem duplex. In FIG. 6, normalized absorbance vs. temperature data for melting of probes P3N, P4N and PNAD (each probe at [1]) is graphically illustrated. As these probes were all unlabeled and comprised the same nucleobase sequence there were directly comparable. Probe P3N which comprises a flexible linkage which links the two arms which form the stem duplex exhibited the most cooperative sigmoidal transition. Surprisingly, the solubility enhanced probe, P4, exhibited only a slightly less cooperative transition as compared with probe P3. The probe PNAD exhibited the least cooperative sigmoidal transition.

The shape of the sigmoidal transition evident in absorbance vs. temperature plots is a function of the properties of the duplex. Sharp cooperative transitions are expected for the more thermodynamically stable duplexes whereas sloping sigmoidal transitions are expected where the duplex is less thermodynamically stable. The flexible linkage in P3 was expected to stabilize the duplex so the sharp transition observed was expected. The substantial difference between probe P4 and PNAD however was surprising and can only be attributed to the presence of the solubility enhancers.

The data presented in FIG. 6 lead us to believe that although probe PNAD was a hairpin, it appeared to be borderline in stability. Therefore we theorized that a probe with shorter arm segments (e.g. 6 subunits in length) might not exist predominately as a hairpin since PNAs are known to be organized in solution (See: Dueholm et al., *New J. Chem.*, 21: 19–31 (1997) at p. 27, col. 2, lns. 6–30). With reference to Table 7, the data presented for probe PNAD 6S, which is designed with a six subunit self-complementary arm segment, as compared with the 9 subunit arm segments of the PNAD probe, confirms that the probe does not exist primarily as a hairpin since the Tm is concentration dependent. Moreover, there are two inflection points in the reannealing curve (data not shown) at low concentrations (samples at [4] and [5])) which is indicative of the existence of both hairpin and multimer formation. Consequently, the data indicates that PNAs having arm segments of 6 or less subunits, and no flexible linkage groups, do not exist primarily as hairpins.

The bimolecular duplex, P5/D5B was also analyzed to determine its Tm. The data obtained by applicants indicated that the most concentrated sample (approximately 7.5 $\mu$M) had a Tm of 71° C. At half concentration the Tm was approximately 70° C. and at one quarter concentration the Tm was approximately 68.5° C.

The DNA probe D5B was complementary to only a portion of PNA probes, P3, P4 and PNAD. The DNA probe, D6, was perfectly complementary to P4 and PNAD and a portion of P3. Hybridization assays were performed to determine whether probes D5B or D6 would hybridize with probes P3 or P4, thereby opening the hairpin stem duplex and generating fluorescent signal. Hybridizations were performed essentially as described in Example 21, below except that the DNA target was in excess. The data obtained indicated that very little hybridization occurred after 30 minutes. As these are the most favored duplexes given the perfect complementary of the probes and targets, the lack of detectable signal in the hybridization reaction indicates that little or no hybridization occurs. Consequently, the data suggests that probes having long stems (e.g. 7–10) and no flexible linkages are not optimal for analyzing samples for a nucleic acid target since they do not produce detectable signal.

These hybridization results should be expected since the Tm of the PNA/DNA duplex should be lower than the Tm of the hairpin stem duplex. For example, the Tm of the perfect complement P5/D5B is approximately 71° C. at concentrations much higher than the effective concentration of reactants in the hybridization reaction whereas the concentration independent Tm of the hairpin stem duplex is 81–82° C. Thus, it is not reasonable to expect that the short DNA probe, D5B, will substantially hybridize to P4 and open the more stable hairpin stem duplex.

In summary, the data presented in this Example 19 demonstrates that PNAs with long self-complementary arm segments (e.g. 9 subunits) and no flexible linkages form stable hairpins while those having shorter arm segments (e.g. 6 subunits) and no flexible linkages are likely to exist in-both the hairpin and multimer state. When hairpins are formed, the Tm of the stem duplex is substantially independent of the presence or absence of magnesium and the ionic strength of the buffer. Unfortunately, the data compiled by applicants indicates that labeled probes most likely to form hairpins, because they possess longer self-complementary arm segments (but do not comprise flexible linkages), exhibit very poor signal to noise ratios in both hybridization and thermal melting experiments. This data suggests that these probes are not well suited for use in the detection of nucleic acid targets. The most surprising result was the substantial stabilizing effect attributable to the dabcyl/fluorescein interactions. Such strong interactions may explain why quenching occurs regardless of lack of substantial spectral overlap between dabcyl and fluorescein (i.e. by non-FRET).

Detailed Analysis of PNA Oligomers Prepared for Study

Experiments 20–22 were performed to generate comparative data on the PNA oligomers in Table 1 so that preferred configurations of PNA Molecular Beacons could be determined. Generally the data indicates that the insertion of flexible linkages within the probes improves signal to noise ratios particularly when the flexible linkage is inserted at the N-terminus of the probe to thereby link an arm segment to the probing nucleobase sequence. The data also indicates that probes with shorter arm segments also generally exhibit a more favorable signal to noise ratio. Several of the probes exhibited signal to noise ratios which were comparable with nucleic acid constructs which are self-indicating (e.g. a nucleic acid Molecular Beacon). Therefore, the PNA Molecular Beacons of this invention are useful for detecting nucleic acid targets in samples of interest. However, the data is inconclusive with regard to whether or not any of the PNA probes listed in Table 1 exist primarily as hairpins. Furthermore, the data indicates that, under the same experimental conditions, the properties of the probes listed in Table 1 vary substantially from probe to probe under the conditions examined. Several of the results are not well understood. Thus, it has not been possible to characterize the PNA probes listed in Table 1.

Example 20

Analysis of Fluorescent Thermal Profiles

General Experimental Procedure:

Fluorescent measurements were taken using a RF-5000 spectrofluorophotometer (Shimadzu) fitted with a water jacketed cell holder (P/N 206-15439, Shimadzu) using a 1.6 mL, 10 mm path length cuvet (Starna Cells, Inc.). Cuvet temperature was modulated using a circulating water bath (Neslab). The temperature of the cuvet contents was monitored directly using a thermocouple probe (Barnant; model No. 600-0000) which was inserted below liquid level by passing the probe tip through the cap on the cuvet (custom manufacture).

Stock solution of HPLC purified PNA oligomer was prepared by dissolving the PNA in 50% aqueous N,N'-dimethylformamide (DMF). From each PNA stock was prepared a solution of PNA oligomer, each at a concentration of 10 pmol in 1.6 mL of Hyb. Buffer (50 mM Tris. HCl pH 8.3 and 100 mM NaCl) by serial dilution of purified PNA stock with Hyb. Buffer.

Samples were exited at 493 nm and the fluorescence measured at 521 nm. Data points were collected at numerous temperatures as the cuvet was heated and then again measured as the cuvet was allowed to cool. Generally, the bath temperature was sequentially increased by 5° C. and then allowed to equilibrate before each data point was recorded. Similarly, to generate the cooling profile, the bath temperature was sequentially decreased by 5° C. and then allowed to equilibrate before each data point was recorded.

Data Discussion:

Nucleic acid Molecular Beacons which form a hairpin structure are expected to exhibit an increase in fluorescent intensity when heated which is consistent with the melting of the hairpin stem and the physical transition of the probe stem from a helix to a random coil. Consistent with any nucleic acid melting event, the process is expected to be reversible thereby resulting in a decrease in fluorescence upon cooling of the sample caused by the resulting reformation of the helical structure. The expected melting phenomenon is documented for nucleic acid Molecular Beacons described by Tyagi et al. (See: Tyagi et al. *Nature Biotechnology*, 14: 303–308 (1996) at FIG. 3).

The results of the fluorescent thermal melting analysis of the PNA Molecular Beacons are summarized in the data presented in Table 8 and presented graphically in FIGS. 7A, 7B1, 7B2, 7B3 and 7C. With reference to Table 8, there are three different general Thermal Profiles observed for the different constructs and under the conditions examined. These are represented in Table 8 as Types A, B and C.

Fluorescent Thermal Profile Type A is characterized by a an increase in fluorescence intensity upon heating (melting) and a correlating decrease in fluorescence intensity upon cooling (reannealing). These results are similar to those published for nucleic acid Molecular Beacons which form a loop and hairpin stem structure. Thus, a Type A Fluorescent Thermal Profile is consistent with the formation of a stable hairpin stem and loop structure. This phenomenon is, therefore, believed to be caused by the melting and reannealing of a stem and loop structure in the PNA Molecular Beacon. However, applicants only claim that a Type A Fluorescent Thermal Profile is indicative of fairly reversible fluorescence quenching, as other structures may be responsible for or contribute to the observed phenomenon.

TABLE 8

Summary of Data Compiled In Experiments 20–22

| Probe No. | CODE | Fluorescent Thermal Profile Observed | Hybridization Profile Observed | Thermal Profile Observed |
|---|---|---|---|---|
| \multicolumn{5}{l}{N-terminal Arm Forming Segments} |
| .001 | 5205 | A | A | Sig, 6% |
| .007 | 5105 | A | A | Sig, 7% |
| .010 | 5005 | B | A | Sig, 19% |
| .002 | 3203 | A | A | Sig, 8% |
| .008 | 3103 | B | A | Sig, 8% |
| .009 | 4004 | B | A | Sig, 8% |
| \multicolumn{5}{l}{C-terminal Arm Forming Segments} |
| .018 | 7027 | B | A, B | Sig. 6% |
| .011A | 5025 | B | A | N. Sig, 5% |
| .006 | 3023 | C | C | N. Sig, 8% |
| \multicolumn{5}{l}{Probing Sequence External To Arm Segments} |
| .017 | 5115 | B | B | N. Sig, 14% |
| .005 | 3113 | C | C | N. Sig, 10% |
| \multicolumn{5}{l}{Control Probes: No Arm Forming Segments} |
| .003 | 0000 | B | B | No Data |
| .004 | 0110 | B | B | N. Sig, 5% |

For a definition of CODE, see Table 1

Figure 7A:
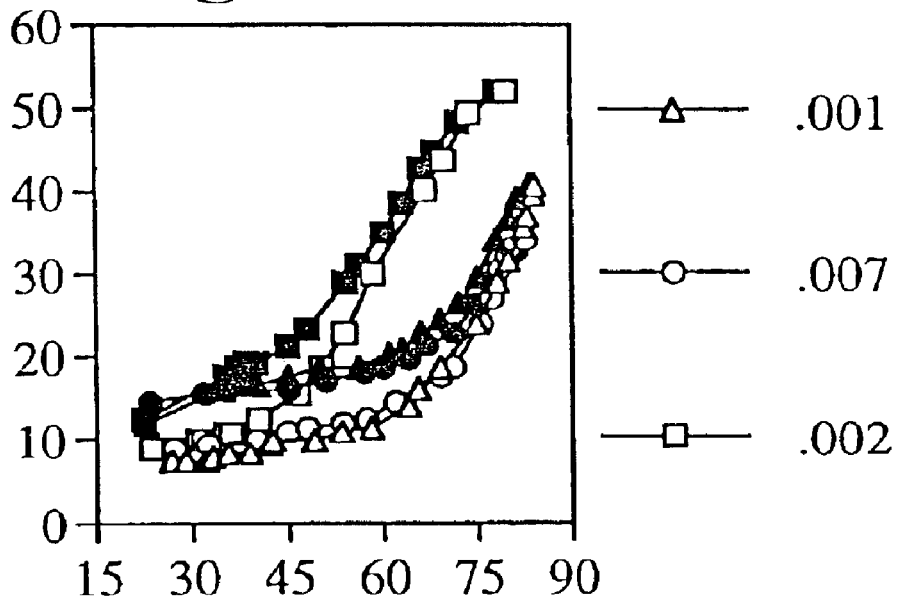
FIG. 7A is a graphical illustration of data for PNA probes which exhibit a Type A Fluorescent Thermal Profile.

Representatives of Type A Fluorescent Thermal Profiles are illustrated in FIG. 7A. The data presented in the Figure is for the PNA oligomers 0.001, 0.007 and 0.002. Data for both the melting (open character) and the reannealing (solid character) is presented. The sigmoidal transitions are consistent with a melting a reannealing of a duplex.

Fluorescent Thermal Profile Type B is characterized by an increase in fluorescence intensity upon heating (melting), but, no substantial correlating decrease in fluorescence intensity upon cooling of the sample. Thus, under the conditions examined, the interactions which initially cause the quenching of fluorescence do not appear to be readily reversible. Consequently, the data suggests that a PNA oligomer exhibiting a Type B Fluorescent Thermal Profile, does not exhibit all the features of a True Molecular Beacon. Nonetheless, as seen by the hybridization assay data, a Type B Fluorescent Thermal Profile does not prohibit the PNA oligomer from functioning as a PNA Beacon.

Representatives of Type B Fluorescent Thermal Profiles are illustrated in FIGS. 8B1, 8B2 and 8B3. The data is presented in three sets so that each trace may be more clearly viewed. The data presented in the Figures are for the PNA oligomers 0.10, 0.008, 0.009 (FIG. 7B1), 0.018, 0.011A, 0.017, (FIG. 7B2), and 0.003 and 0.004, (FIG. 7B3). Data for both the melting (open character) and the reannealing (solid character) is presented.

Fluorescent Thermal Profile Type C is characterized by a high initial fluorescent intensity which initially decreases with heating and again decreases even further upon cooling of the sample. The high initial fluorescent intensity suggests that this construct does not exhibit the initial fluorescence quenching observed with most of the other PNA constructs examined. The constant decrease in fluorescent intensity upon cooling is not well understood. Nevertheless, as seen by the hybridization assay data, a Type C, Fluorescent Thermal Profile does not prohibit the PNA oligomer from functioning as a PNA Beacon.

Figure 7C:
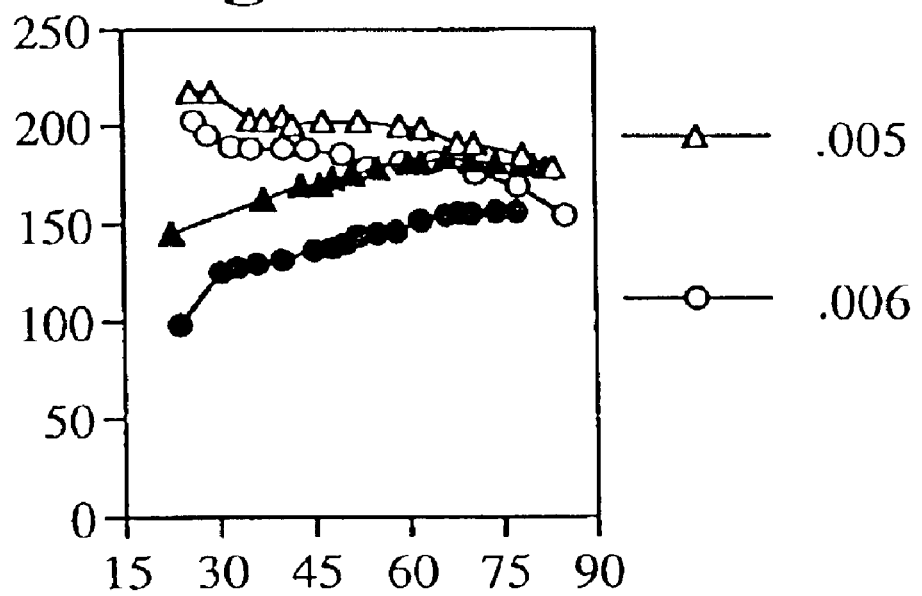
FIG. 7C is a graphical illustration of data for PNA probes which exhibit a Type C Fluorescent Thermal Profile.

Representatives of Type C Fluorescent Thermal Profiles are illustrated in FIG. 7C. The data presented in the FIG. 7C is for the PNA oligomers 0.005 and 0.006. Data for both the melting (open character) and the reannealing (solid character) is presented.

Example 21

Analysis of Hybridization Assay Data

General Experimental Procedures:

All hybridization assay data was collected using a Wallac 1420 VICTOR equipped with a F485 CW-lamp filter and a F535 Emission filter. The NUNC MaxiSorp, breakapart microtitre plate was used as the reaction vessel. Each microtitre plate was prewashed with Hyb. Buffer at room temperature for 15 minutes before the reaction components were added. Total reaction volume was 100 $\mu$L in Hyb. Buffer.

Stock solution of purified PNA probe was prepared by dissolving the PNA in 50% aqueous N,N'-dimethylformamide (DMF). From this PNA Stock was prepared a solution of each PNA at a concentration of 25 pmole/1 $\mu$L by serial dilution of the PNA Stock with 50% aqueous DMF.

Stock solution of purified wt k-ras DNA was prepared by dissolving the purified DNA in TE (10 mM Tris. HCl pH 8.0; 1.0 mM EDTA, Sigma Chemical). From this DNA Stock was prepared a solution of wt k-ras DNA at a concentration of 100 pmol/99 $\mu$L by serial dilution of the DNA Stock with Hyb. Buffer.

Each reaction sample used for analysis was prepared by combining 1 $\mu$L of the appropriate PNA oligomer (25 pmole/$\mu$L) with either of 99 $\mu$L of wt k-ras DNA stock or 99 $\mu$L of Hyb. Buffer (control) as needed to prepare 100 $\mu$L of sample.

Samples were mixed and then fluorescence intensity monitored with time using the Wallac VICTOR instrument. Samples were run in triplicate to insure reproducible results. Data was acquired for 20–25 minutes after the reactants were mixed and then the wells were sealed and the plate heated to 42–50° C. in an incubator for 30–40 minutes. After cooling to ambient temperature, the wells were unsealed and then another 10 data points were collected over approximately five minutes.

Data Discussion:

Nucleic acid Molecular Beacons which form a hairpin stem and loop structure are expected to exhibit an increase in fluorescent intensity upon hybridization of the probing sequence to complementary nucleic acid. The expected increase in fluorescent intensity is documented for DNA Molecular Beacons described by Tyagi et al. (See: Tyagi et al. *Nature Biotechnology,* 14: 303–308 (1996)).

The results of the hybridization analysis of the PNA oligomers are summarized in Table 8 and presented graphically in FIGS. 8A1, 8A2, 8A3, 8B and 8C. With reference to Table 8, there are three different general Hybridization Profiles observed for the different constructs examined. These are represented in Table 8 as Types A, B and C. In FIG. 10, the signal to noise ratio (before and after heating) for all probes examined are graphically illustrated.

Hybridization Profile Type A is characterized by the increase in fluorescence intensity in samples containing complementary target DNA as compared with samples containing only the PNA oligomer. After heating, the fluorescent intensity of samples containing target sequence increases but the background fluorescence of the control sample(s) does not significantly change. Because the PNAs possess a very low inherent fluorescence, the probes which exhibit a Type A, Hybridization Profile generally have the highest signal to noise ratios. Representatives of Type A Hybridization Profiles are illustrated in FIGS. 8A1, 8A2 and 8A3. The data is presented in two separate graphical illustrations to clarify the presentation. The data presented in the Figures is for the PNA oligomers 0.001, 0.007, 0.010 (FIG. 8A1), and 0.002, 0.008, 0.009 (FIG. 8A2), and 0.11A, 0.017 and 0.018 (FIG. 8A3).

Figure 8B:
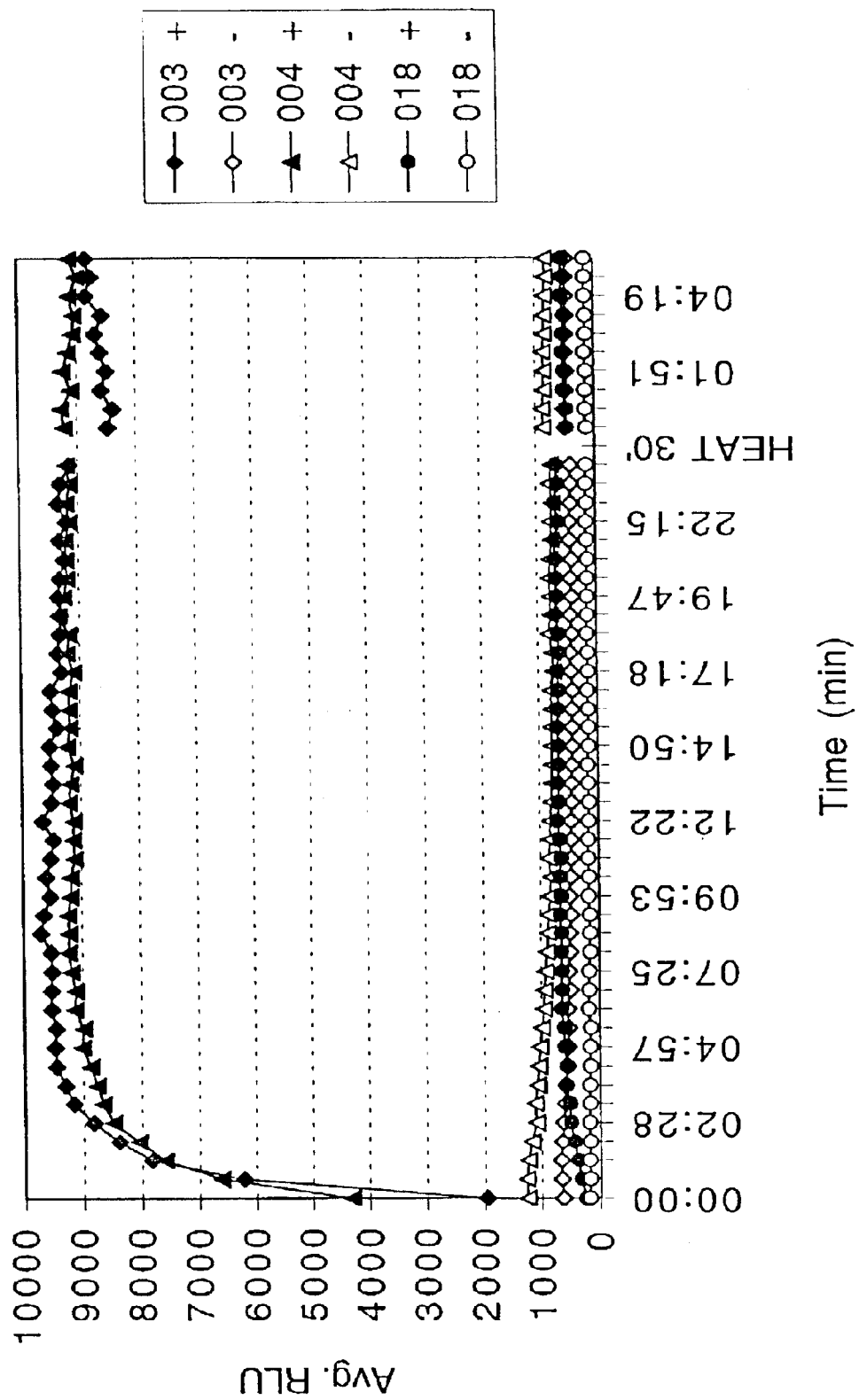
FIG. 8B is a graphical illustration of data for PNA probes which exhibit a Type B Hybridization Profile.

Hybridization Profile Type B is characterized by the very rapid increase in fluorescence intensity in samples containing complementary target DNA as compared with samples containing only the PNA oligomer. The fluorescence intensity quickly reaches a plateau which does not significantly change (if at all) after heating. The background fluorescence of the control sample(s) does not change significantly even after heating. This suggest that the hybridization event rapidly, and with little resistance, reaches a binding equilibrium without any requirement for heating. Representatives of Type B Hybridization Profiles are illustrated in FIG. 8B. The data presented in FIG. 8B is for the PNA oligomers 0.018, 0.003 and 0.004 though PNA oligomer 0.018 does not exhibit all the characteristics of a Type B Hybridization Profile. Specifically, the signal for probe 0.018 does not appear to increase after heating (Type B) but the hybridization kinetics appear to be more like a Type A Hybridization Profile.

Control probes 0.003 and 0.004 (herein referred to as PNA Molecular Beacons) exhibit a Type B Hybridization Profile. Thus, the rapid hybridization kinetics of the Type B Hybridization Profile is probably the result of having no stable hairpin stem, or any other strong force, which can stabilize the non fluorescent polymer form. Nonetheless, the dynamic range (signal to noise ratio) observed in the hybridization assay of these probes is typically quite high and suggests that forces other than the hydrogen bonding of complementary nucleobases of arm segments can stabilize the interactions between the donor and acceptor moieties. The data presented in Example 19 suggests that label/label interactions can be quite strong and may be an important factor in this surprising result.

Though the background (noise) is higher for the 0.003 and 0.004 probes, as compared with the 0.001, 0.002, 0.007, 0.009 and 0.010 probes, the fluorescence intensity after hybridization is higher than that observed in any probes yet examined. As a result of the higher background, PNA oligomers 0.003 and 0.004 have a very favorable signal to noise ratio. This S/N ratio is nearly as favorable as any (and better than some) of the other PNA oligomers examined whether or not they possess arm segments. The data demonstrates that it is not necessary to have arm forming segments to create a probe which exhibits an initial low fluorescence intensity and a corresponding increase in fluorescence signal upon the binding of the probe to a target sequence.

Figure 8C:
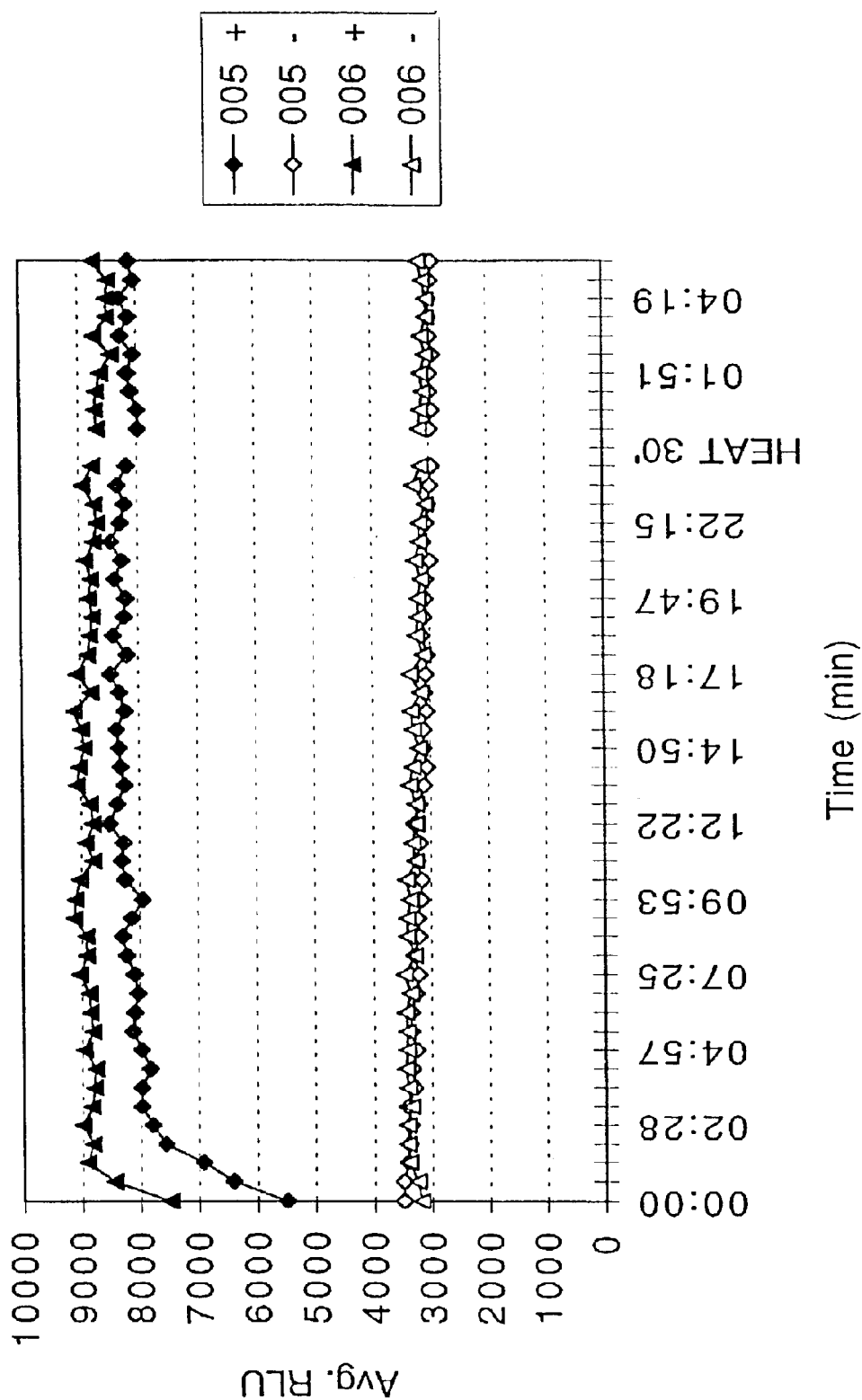
FIG. 8C is a graphical illustration of data for PNA probes which exhibit a Type C Hybridization Profile.

Hybridization Profile C is characterized by a moderate increase in fluorescence intensity in samples containing target DNA as compared with samples containing only the PNA oligomer. The fluorescence intensity quickly reaches a plateau which does not significantly change (if at all) after heating. The background fluorescence of the control sample(s) is relatively high but does not change significantly even after heating. Hybridization Profiles B and C differ primarily because the background fluorescence in the control samples, containing no target nucleic acid, are dramatically higher in Hybridization Profile Type C. The hybridization data obtained for samples containing complementary nucleic acid, suggests that the hybridization event rapidly, and with little resistance, reaches equilibrium. However, the very high background signal suggests that the forces which should hold the donor and acceptor moieties in close proximity are not strong enough in these constructs to effectively quench the fluorescent signal. As a consequence of the moderate increase in fluorescence upon binding to the target sequence and the higher than usual intrinsic fluorescence a PNA Molecular Beacon, which exhibits a Type C Hybridization Profile, has a very low signal to noise ratio. Representatives of Type C Hybridization Profiles are illustrated in FIG. 8C. The data presented in FIG. 8C is for the PNA oligomers 0.006 and 0.005, respectively.

Example 22

Ultraviolet Thermal Profile Analysis

The data collected for this Example was intended to determine whether the fluorescence vs. temperature analysis presented in Example 20 correlated with ultraviolet (UV) absorbance (260 nm) vs. temperature plots. Additionally, concentration dependency of the traces was also examined in order to determine whether the PNA Molecular Beacons listed in Table 1 (except probe 0.003) existed as a hairpin or as a multimer.

Materials and Methods:

The purified probes were dissolved in the Hyb. Buffer to a concentration which was intended to be approximately 5–7.5 $\mu$M. However it was determined that the PNA Molecular Beacons were too insoluble such that a large proportion of the PNA probe existed in a suspension. The solutions were centrifuged to remove suspended matter and therefore the most concentrated samples examined were estimated to have a concentration of approximately 2.5 $\mu$M or less. The most concentrated stocks were then serially diluted with Hyb. Buffer two times so that for each sample, a total of three concentrations could be examined. All samples were analyzed using a Cary 100 Bio UV-Visible Spectrophotometer (Varian Instruments) equipped with a 6×6 thermostatable multicell block running Win UV Bio application software package. To a 10×10 UV cell (Starna Cells, P/N 21-Q-10) was added a 7.2 mm stir bar and the 2.5 mL of each sample of the dilution series. The stirring accessory was used during all analysis. All samples were thermally denatured and reannealed prior to data collection by having the instrument rapidly ramp to at least 90C. and then holding for 5 minutes before returning to the starting temperature of 20° C. After the premelt, it was preferable to allow the samples to remain at the starting temperature for at least 30 minutes to reach equilibrium before beginning data collection. Data for both dissociation and reannealing was collected and analyzed. The temperature range over which data was collected was 20–90° C. The temperature ramp rate for both dissociation and reannealing was 0.5° C./min. The absorbance (260 nm, averaged over a 2–3 second collection) was plotted vs. the temperature of the multicell block.

Results:

Factors to be considered in analyzing the absorbance vs. temperature plots include whether the transition was sigmoidal, whether and to what extent there was any hysteresis and the percent hyperchromicity (for the purposes of this discussion the percent hyperchromicity will be defined as the approximate percent difference between the absorbance at 20° C. and the absorbance at 90° C.). Summary of the data obtained by analysis of the absorbance vs. temperature plots is presented in Table 8.

Probes 0.001, 0.002, 0.007, 0.008, 0.009, 0.010 and 0.018 exhibited a sigmoidal transition as indicated by "Sig" in Table 8. The sigmoidal transition is characteristic of the melting and reannealing of a duplex or hairpin. Probes. 0.004, 0.005, 0.006, 011A and 0.017 all exhibited a non-sigmoidal transition as indicated by "N. Sig" in Table 8. Curiously, the shape of the non-sigmoidal transition was essentially the same in all cases except for 0.011A. For these probes the increase in absorbance as a function of temperature appeared to be almost linear. The non-sigmoidal shape of these curves suggest that the transition is not the result of the melting and reannealing of a duplex structure. Thus, these probe are not likely to exist as hairpins or multimers.

Not a single probe examined was without a noticeable hysteresis. Though the extent of hysteresis varied widely, the presence of a conspicuous hysteresis indicates that the probes are resistant to returning to their original confirmation as a hairpin, mulitmer or other confirmation. Though this result was generally observed in the fluorescence vs. temperature plots, the absorbance traces were far more reversible upon cooling as compared with the data observed in the fluorescence vs. temperature plots. Therefore, the substantial differences between the fluorescence vs. temperature and absorbance vs. temperature plots are not understood. Moreover, it is unclear why only probes 0.001, 0.002 and 0.007 exhibited a reversible decrease in fluorescence upon cooling whereas other probes did not. However, the data suggests that the longer flexible linkages and longer arm segments promote favorable properties since probes 0.001 and 0.002 both possess 2 flexible linkages and probe 0.007, though is possesses only one flexible linkage, it comprises 5 subunit arm segments.

For comparison, normalized absorbance vs. temperature and fluorescence vs. temperature data for probe 0.001 was overlaid since the plots looked relatively similar. The overlaid data is presented in FIG. 9. With reference to FIG. 9, the absorbance vs. temperature and fluorescence vs. temperature data is fairly superimposible. The absorbance vs. temperature and fluorescence vs. temperature plots for probe 0.002 and 0.007 were likewise very similar thought the data has not yet been overlaid. The good correlation between the absorbance vs. temperature and fluorescence vs. temperature plots suggests that the same transition is being measured in both analyses and it is likely to be a helix to coil transition.

Except for probes 0.010, 0.005 and 0.017, the percent hyperchromicity is less than 10 percent. Generally, the hyperchromic effect for a duplex to random coil transition is greater than 10 percent. The hyperchromicity for the DNA and PNA probes examined in Example 19 were all better than 15 percent. Thus, the lower than expected hyperchromic effect for substantially all probes, except probe, 0.010 which exhibits a 19 percent hyperchromic effect, is not well understood. Nevertheless, the values are not consistent with at melting of a duplex of a hairpin even for probes which exhibited a sigmoidal transition.

Finally, the data obtained by applicants was inconclusive with regard to whether the PNA Molecular Beacons listed in Table 1 exist as a hairpin or multimer because the scatter in the data at the lower concentrations made it impossible to obtain reliable derivative information from which the Tm values are determined. Though the data generated in Example 19 would suggest that probes comprising arm segments of six or less subunits are not likely to form hairpins, the effect of flexible linkers was not fully evaluated in that Example. Thus, it remains unknown whether any of the probes listed in Table 1 exist primarily as hairpins.

In summary, the data presented in this Example 22 is inconclusive as to whether the PNA Molecular Beacons listed in the Table exist primarily as hairpins or mulitmers. It does however show there is good agreement between the absorbance vs. temperature plots and the fluorescence vs. temperature plots for probes 0.001, 0.002 and 0.007. The lack of correlation between absorbance vs. temperature plots and the fluorescence vs. temperature plots for other probes supports the theory that the probes may adopt structures other than hairpins or multimers. This theory is supported by the non-sigmoidal transitions, the substantial hysteresis and the very low percent hyperchromicity for most of the probes.

General Discussion of the Data Presented in Examples 19–22

Though all the probes examined exhibited a detectable increase in fluorescent signal in the presence of a target sequence, the probes which exhibit properties which are most like nucleic acid Molecular Beacons are probes 0.001, 0.002 and 0.007. These probes process very favorable signal to noise ratios, exhibit sigmoidal transitions during melting and also readily reannealed upon cooling whether the analysis was by fluorescence or absorbance. This data indicates that probes of this configuration form duplexes which dissociate upon hybridization or thermal melting to produce an increase in detectable signal though it is not known whether or not these probes exist primarily as hairpins. Whether hairpins or not, the favorable characteristics of these probes correlate with the presence of flexible linkages and arm segments in the range of 3 to 5 subunits in length. Furthermore, the data in Example 19 in combination with the data for probe 0.018, in Examples 20–22, demonstrate that long arm segments of 7 to 9 subunits substantially reduce signal thereby resulting in very poor signal to noise ratios. Consequently, long arm segments are a disfavored configuration for a PNA Molecular Beacon.

Though probes 0.001, 0.002 and 0.007 exhibited the most favorable properties, all the probes listed in Table 1, except for control probes 0.003 and 0.004, are PNA Molecular Beacons because they comprise arm segments and appropriate labeling and also exhibit a detectable change in a property of a label which correlates with the binding of the probe to a target sequence. The nature of the forces which result in fluorescence quenching of the other PNA probes is not well understood, though it is likely that nucleobase-nucleobase, electrostatic and hydrophobic-hydrophobic interactions contribute to fix the probes in a favorable secondary structure until this is altered by hybridization.

Surprisingly, the control probes 0.003 and 0.004, which have no arm forming segments, exhibit a correlation between increased fluorescence intensity and binding of the probe to target sequence. Remarkably these probe exhibit a very good signal to noise ratio in hybridization assays. Thus, it has been demonstrated that PNA oligomers need not comprise regions of complementary nucleobases which are, by design, intended to form a hairpin to thereby exhibit many of the favorable characteristics of a nucleic acid Molecular Beacon. Since PNA oligomers 0.003 and 0.004 cannot form duplexes, this result demonstrates that other types of secondary structures can result in fluorescence quenching until the probe hybridizes to a target sequence.

Equivalents

While this invention has been particularly shown and described with references to preferred embodiments thereof, it will be understood by those of ordinary skill in the art that various changes in form and details may be made therein without departing from the spirit and scope of the invention as defined by the appended claims. Those skilled in the art will be able to ascertain, using no more than routine experimentation, many equivalents to the specific embodiments of the invention described herein. Such equivalents are intended to be encompassed in the scope of the claims.

We claim:

1. A method for in-situ analysis of a target sequence of an organism of interest in a sample, said method comprising:
   a) providing a sample of fixed cells for in-situ analysis;
   b) treating the sample with a polymer of covalently linked subunits, said polymer comprising;
      i) a non-polynucleotide probing nucleobase sequence that is complementary or substantially complementary to a target sequence;
      ii) a first arm segment and a second arm segment that are covalently linked to, or embedded within, the probing nucleobase sequence and wherein at least one of the first or second arm segments is covalently linked to the probing nucleobase sequence through a flexible linkage;
      iii) at least one linked donor moiety and at least one linked acceptor moiety, wherein said donor and acceptor moieties are covalently linked to the polymer at positions that are separated by at least a portion of the probing nucleobase sequence;
   c) detecting, identifying or quantitating the hybridization of the polymer to the target sequence, under suitable in-situ hybridization conditions, wherein the presence, absence or amount of target sequence present in the sample is correlated with a change in detectable signal associated with at least one donor or acceptor moiety of the polymer; and d) detecting, identifying or quantitating the organism of interest in the sample based upon the presence, absence or amount of the hybridization of the polymer to the target sequence that is determined.

2. The method of claim 1, wherein excess polymer is not washed away prior to performing step (c).

3. The method of claim 1, wherein blocker probes are added to improve assay performance.

4. The method of claim 1, wherein the determination of detectable signal is made using a microscope, laser scanning device or flow cytometer.

5. The method of claim 1, wherein the organism of interest is selected from the group consisting of a bacteria or a virus.

6. The method of claim 1, wherein the method is repeatedly performed to determine the effect of antimicrobial agents on the growth of one or more microorganisms.

7. The method of claim 1, wherein the method is selected to determine target sequences that are particular to organisms found in food, beverages, water, pharmaceutical products, personal care products, dairy products or environmental samples.

* * * * *

SEQUENCE LISTING

<160> NUMBER OF SEQ ID NOS: 13

<210> SEQ ID NO 1
<211> LENGTH: 24
<212> TYPE: DNA
<213> ORGANISM: Artificial Sequence
<220> FEATURE:
<221> NAME/KEY: misc_feature
<222> LOCATION: (1)
<223> OTHER INFORMATION: 5' Biotin
<220> FEATURE:
<223> OTHER INFORMATION: Description of Artificial Sequence:SYNTHETIC
      PROBE OR TARGET

<400> SEQUENCE: 1
gtggtagttg gagctggtgg cgta                                          24

<210> SEQ ID NO 2
<211> LENGTH: 24
<212> TYPE: DNA
<213> ORGANISM: Artificial Sequence
<220> FEATURE:
<221> NAME/KEY: misc_feature
<222> LOCATION: (1)
<223> OTHER INFORMATION: 5' Biotin
<220> FEATURE:
<223> OTHER INFORMATION: Description of Artificial Sequence:SYNTHETIC
      PROBE OR TARGET

<400> SEQUENCE: 2
gtggtagttg gagcttgtgg cgta                                          24

<210> SEQ ID NO 3
<211> LENGTH: 18
<212> TYPE: DNA
<213> ORGANISM: Artificial Sequence
<220> FEATURE:
<221> NAME/KEY: misc_feature
<222> LOCATION: (1)
<223> OTHER INFORMATION: 5' Biotin
<220> FEATURE:
<223> OTHER INFORMATION: Description of Artificial Sequence:SYNTHETIC
      PROBE OR TARGET

<400> SEQUENCE: 3
actcctacgg gaggcagc                                                 18

<210> SEQ ID NO 4
<211> LENGTH: 9
<212> TYPE: DNA
<213> ORGANISM: Artificial Sequence
<220> FEATURE:
<221> NAME/KEY: misc_feature
<222> LOCATION: (1)
<223> OTHER INFORMATION: 5'-Fluorescein
<220> FEATURE:
<223> OTHER INFORMATION: Description of Artificial Sequence:SYNTHETIC
      PROBE OR TARGET

<400> SEQUENCE: 4 atatattgg                                                            9

<210> SEQ ID NO 5
<211> LENGTH: 9
<212> TYPE: DNA
<213> ORGANISM: Artificial Sequence
<220> FEATURE:
<223> OTHER INFORMATION: Description of Artificial Sequence:SYNTHETIC -continued

```
       PROBE OR TARGET

<400> SEQUENCE: 5 atatattgg                                                                  9

<210> SEQ ID NO 6
<211> LENGTH: 9
<212> TYPE: DNA
<213> ORGANISM: Artificial Sequence
<220> FEATURE:
<221> NAME/KEY: misc_feature
<222> LOCATION: (9)
<223> OTHER INFORMATION: 3' Dabcyl
<220> FEATURE:
<223> OTHER INFORMATION: Description of Artificial Sequence:SYNTHETIC
      PROBE OR TARGET

<400> SEQUENCE: 6 ccaatatat                                                                  9

<210> SEQ ID NO 7
<211> LENGTH: 9
<212> TYPE: DNA
<213> ORGANISM: Artificial Sequence
<220> FEATURE:
<223> OTHER INFORMATION: Description of Artificial Sequence:SYNTHETIC
      PROBE OR TARGET

<400> SEQUENCE: 7 ccaatatat                                                                  9

<210> SEQ ID NO 8
<211> LENGTH: 18
<212> TYPE: DNA
<213> ORGANISM: Artificial Sequence
<220> FEATURE:
<221> NAME/KEY: misc_feature
<222> LOCATION: (1)
<223> OTHER INFORMATION: 5' Fluorescein
<220> FEATURE:
<221> NAME/KEY: misc_feature
<222> LOCATION: (9)..(10)
<223> OTHER INFORMATION: spacer
<220> FEATURE:
<221> NAME/KEY: misc_feature
<222> LOCATION: (18)
<223> OTHER INFORMATION: 3' Dabcyl
<220> FEATURE:
<223> OTHER INFORMATION: Description of Artificial Sequence:SYNTHETIC
      PROBE OR TARGET

<400> SEQUENCE: 8
atatattggc caatatat                                                       18

<210> SEQ ID NO 9
<211> LENGTH: 18
<212> TYPE: DNA
<213> ORGANISM: Artificial Sequence
<220> FEATURE:
<221> NAME/KEY: misc_feature
<222> LOCATION: (9)
<223> OTHER INFORMATION: spacer
<220> FEATURE:
<223> OTHER INFORMATION: Description of Artificial Sequence:SYNTHETIC
      PROBE OR TARGET

<400> SEQUENCE: 9
atatattggc caatatat                                                       18
```

```
<210> SEQ ID NO 10
<211> LENGTH: 23
<212> TYPE: DNA
<213> ORGANISM: Artificial Sequence
<220> FEATURE:
<221> NAME/KEY: misc_feature
<222> LOCATION: (1)
<223> OTHER INFORMATION: 5' Fluorescein
<220> FEATURE:
<221> NAME/KEY: misc_feature
<222> LOCATION: (23)
<223> OTHER INFORMATION: 3' Dabcyl
<220> FEATURE:
<223> OTHER INFORMATION: Description of Artificial Sequence:SYNTHETIC
      PROBE OR TARGET

<400> SEQUENCE: 10
atatattggc tgatccaata tat                                            23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:SYNTHETIC
      PROBE OR TARGET

<400> SEQUENCE: 11
atatattggc tgatccaata tat                                            23

<210> SEQ ID NO 12
<211> LENGTH: 12
<212> TYPE: DNA
<213> ORGANISM: Artificial Sequence
<220> FEATURE:
<221> NAME/KEY: misc_feature
<222> LOCATION: (1)
<223> OTHER INFORMATION: 5' Biotin
<220> FEATURE:
<223> OTHER INFORMATION: Description of Artificial Sequence:SYNTHETIC
      PROBE OR TARGET

<400> SEQUENCE: 12
tggatcagcc aa                                                        12

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:SYNTHETIC
      PROBE OR TARGET

<400> SEQUENCE: 13
atatattgga tcagccaata tat                                            23
```